United States Patent [19]
Giuseppin et al.

[11] Patent Number: 6,004,776
[45] Date of Patent: *Dec. 21, 1999

[54] PROCESS FOR PREPARING A PROTEIN BY A FUNGUS TRANSFORMED BY MULTICOPY INTEGRATION OF AN EXPRESSION VECTOR

[75] Inventors: Marco F. Giuseppin, Schiedam, Netherlands; Maria T. S. Lopes, Monte da Caparica, Portugal; Roelf J. Planta, Uithoorn, Netherlands; Johannes M. A. Verbakel, Maasland, Netherlands; Cornelis T. Verrips, Maassluis, Netherlands

[73] Assignee: Unilever Patent Holdings, B.V., Rotterdam, Netherlands

[*] Notice: This patent is subject to a terminal disclaimer.

[21] Appl. No.: 08/748,836

[22] Filed: Nov. 15, 1996

Related U.S. Application Data

[62] Continuation of application No. 08/364,010, Dec. 27, 1994, which is a continuation of application No. 07/781,130, filed as application No. PCT/EP90/01138, Jul. 9, 1990, abandoned.

[30] Foreign Application Priority Data

Jul. 7, 1989 [GB] United Kingdom .................. 8915659
Apr. 20, 1990 [EP] European Pat. Off. ............. 90201007

[51] Int. Cl.$^6$ .............................. C12P 21/02; C12N 1/15; C12N 1/16; C12N 15/81
[52] U.S. Cl. ............... 435/69.1; 435/172.1; 435/254.21; 435/320.1
[58] Field of Search ................................ 435/69.1, 172.1, 435/172.3, 320.1, 254.1, 254.11, 254.21, 254.23, 254.3, 254.9, 254.6; 935/33, 34, 37, 47, 48

[56] References Cited

U.S. PATENT DOCUMENTS 4,935,496  6/1990  Kudo et al. ..................... 530/387.3
5,001,230  3/1991  Brown et al. ..................... 536/23.5

FOREIGN PATENT DOCUMENTS

| 0 171 142 | 2/1986 | European Pat. Off. . |
| 0171142 | 2/1986 | European Pat. Off. . |
| 0228009 | 7/1987 | European Pat. Off. . |
| 0318775 | 6/1989 | European Pat. Off. . |
| WO 86/00089 | 1/1986 | WIPO . |
| 8707641 | 12/1987 | WIPO . |

OTHER PUBLICATIONS

Kingsman et al, "Heterologous Gene Expression in *Saccharmyces cerevisiae*", Biotech. Gen. Eng. Rev. 12, 377–406.

Lopes et al, "High–Copy–Number Integration In the Ribosomal . . . ", Helsinki, 1988 (abstract).

Lopes et al, "High–copy–number integration into the ribosomal . . . ", Gene, 79 (1989) 199–206.

*Primary Examiner*—Nancy Degen
*Attorney, Agent, or Firm*—Cushman Darby & Cushman IP Group of Pillsbury Madison & Sutro

[57] ABSTRACT

A process is disclosed for preparing a protein by a eukaryote transformed by multicopy integration of an expression vector into the genome of a yeast, such as Saccharomyces, Hansenula, and Kluyveromyces, or of a mould such as Aspergillus, Rhizopus and Trichoderma, the expression vector containing both an "expressible gene" encoding the protein and a so-called "deficient selection marker needed for the growth of the yeast or mould in a specific medium", such as the LEU2d, TRP1d or URA3d gene, in combination with a ribosomal DNA sequence, resulting in stable high copy integration of 100–300 copies per cell. This multicopy integration results in an increased production of the desired protein, which can be guar α-galactosidase, an oxidase or a hydrolytic enzyme such as a lipase.

3 Claims, 49 Drawing Sheets

Fig.2A

ClaI

```
     ATGGTCAGATCGATGCCTTCCAGGTGTGGGCGGAGGGCGGTGCATGGGCGTTGGCGGTG
1    ------+---------+---------+---------+---------+---------+   60
     TACCAGTCTAGCTACGCAAGGTCCCACCCGCCGCCTCCCGGCACCGTACCCGAACCGCCAC

-39  M  V  R  S  M  R  S  R  V  A  A  R  A  V  A  W  A  L  A  V  -

ATGCCCGCTGGCCGGGGCGGGGGCCGGGTTGACGATGGCCGCGTCGCCCCGGCGTCGGGGCG
61   ------+---------+---------+---------+---------+---------+   120
     TACGGGCGACCGGCCCCGGCCCCCGGCCCAACTGCTACCGGCGCAGCGGGGCCGCAGCCCGC

M  P  L  A  G  A  A  G  L  T  M  A  A  S  P  A  A  V  A  A  -
                                   sig.seq.                -1 ↑ 1

GACACCTACGCGGCGACGCGCTATCCGGTGATCCTCGTCCACGGCCTCGCGGGCACCGAC
121  ------+---------+---------+---------+---------+---------+   180
     CTGTGGATGCGCCGCTGCGCGATAGGCCACTAGGAGCAGGTGCCGGAGCGCCCCTGCCTG

D  T  Y  A  A  T  R  Y  P  V  I  L  V  H  G  L  A  G  T  D  -
     mature lipase AAGTTCGCGAACGTGGTGGACTATTGGTACGGAATCCAGAGCGATCTGCAATCGCATGGC
181  ------+---------+---------+---------+---------+---------+   240
     TTCAAGCGCTTGCACCACCTGATAACCATGCCTTAGGTCTCGCTAGAGACGTTAGCGTACCG

```
        GCGAAGGTGTACGTCGCGAATCTCTCGGGATTCCAGAGCGACGACGGGCCGAACGGCCGC
241     ------------+------------+------------+------------+------------+------------+   300
        CGCTTCCACATGCAGCGCTTAGAGAGCCCTAAGGTCTCGCTGCTGCCCGGCTTGCCGGCG

A   K   V   Y   V   A   N   L   S   G   F   Q   S   D   D   G   P   N   G   R    -
                                         P
                                         v
                                         u
                                         H
                                         I

GGCGAGCAGCTGCTCGCCTACGTGAAGCAGGTGCTCGCGGCCACCGGGGCGACCAAGGTG
301     ------------+------------+------------+------------+------------+------------+   360
        CCGCTCGTCGACGAGCGGATGCACTTCGTCCACGAGCGCCGGTGGCCGCTGGTTCCAC

G   E   Q   L   L   A   Y   V   K   Q   V   L   A   A   T   G   A   T   K   V    -

AACCTGATCGGCCACAGCCAGGGCGGCCTGACCTCGCGGTACGTCGCGGCCGTCGCGCCG
361     ------------+------------+------------+------------+------------+------------+   420
        TTGGACTAGCCGGTGTCGGTCCCGCCGGACTGGAGCGCCATGCAGCGCCGGCAGCGCGGC

N   L   I   G   H   S   Q   G   G   L   T   S   R   Y   V   A   A   V   A   P    -

CAACTGGTGGCCTCGGTGACGACGATCGGCACGCCGCATCGGGCTCCGAGTTCGCCCGAC
421     ------------+------------+------------+------------+------------+------------+   480
        GTTGACCACCGGAGCCACTGCTGCTAGCCGTGCGGCGTAGCCCGAGGCTCAAGCGGGCTG

```
      TTCGTGCAGGACGTGCTGAAGACCGATCCGACCGGGCTCTCGTCGACGGTGATCGCCGCC
481   ------+---------+---------+---------+---------+---------+ 540
      AAGCACGTCCTGCACGACTTCTGGCTAGGCTGGCCCCGAGAGCAGCTGCCACTAGCGGCGG

F  V  Q  D  V  L  K  T  D  P  T  G  L  S  S  T  V  I  A  A  -
                                     S
                                     a
                                     I

TTCGTCAACGTGTTCGGCACGCTCGTCAGCAGCTCGCACAACACCGACCAGGACGCGCTC
541   ------+---------+---------+---------+---------+---------+ 600
      AAGCAGTTGCACAAGCCGTGCGAGCAGTCGTCGAGCGTGTTGTGGCTGGTCCTGCGCGAG

F  V  N  V  F  G  T  L  V  S  S  S  H  N  T  D  Q  D  A  L  -

GCGGCGCTGCGCACGCTCACCACCGCCCAGACCGCCACCTACAACCGGAACTTCCCGAGC
601   ------+---------+---------+---------+---------+---------+ 660
      CGCCGCGACGCGTGCGAGTGGTGGCGGGTCTGGCGGTGGATGTTGGCCTTGAAGGGCTCG

A  A  L  R  T  L  T  T  A  Q  T  A  T  Y  N  R  N  F  P  S  -

GCGGGCCTGGGCGCCCCGGGTTCCTGCCAGACGGGCGCCGACCGAAACCGTCGGCGGC
661   ------+---------+---------+---------+---------+---------+ 720
      CGCCCGGACCCCGGGGCCCAAGCACGTCTGCCCGGCGCTGGCTTTGGCAGCCGCCCG

```
      AGCCAGGACCTGCTCTATTCGTGGGGGGGCACCGCGATCCAGCCCACCTCCACCGTGCTC
721   ------+---------+---------+---------+---------+---------+ 780
      TCGGTCGTGGACGAGATAAGCACCCCCGCGTGGCGCTAGGTCGGGTGGAGGTGGCACGAG
       S  Q  H  L  L  Y  S  W  G  G  T  A  I  Q  P  T  S  T  V  L  -

GGCCTGACCGGGGCGACCGACACCAGCACCGGCACGCTCGACGTCGCGAACGTGACCGAC
781   ------+---------+---------+---------+---------+---------+ 840
      CCGGACTGGCCCCGCTGGCTGTGGTCGTGGCCGTGCGAGCTGCAGCGCTTGCACTGGCTG
       G  V  T  G  A  T  D  T  S  T  G  T  L  D  V  A  N  V  T  D  -

CCGTCCACGCTCGCGCTGCTCGCCACCGGCGCGGTGATGATCAATCGCGCCTCGGGGCAG
841   ------+---------+---------+---------+---------+---------+ 900
      GGCAGGTGCGAGCGCGACGAGCGGTGGCCGCGCCACTACTAGTTAGCGCGGAGCCCCGTC
       P  S  T  L  A  L  L  A  T  G  A  V  M  I  N  R  A  S  G  Q  -
                                        P
                                        s
                                        t
                                        I

AACGACGGGCTCGTCTCCGGCTCGCAGCTCGCTGTTCGGGCAGGTGATCAGCACCAGCTAC
901   ------+---------+---------+---------+---------+---------+ 960
      TTGCTGCCCGAGCAGAGGCCGAGCAGTCGAGCTCGAAGCCCGTCCACTAGTCGTGGTCGATG
       N  D  G  L  V  S  R  C  S  S  L  F  G  Q  V  I  S  T  S  Y  -
```

Fig. 2E

```
                              P
                              v
                              u
                              I
                              I
      CACTGGAACCATCTCGACGAGATCAACCAGCTGCTCGGCGTGCGGGGCGCCAACGCGGAA
 961  ------+---------+---------+---------+---------+---------+  1020
      GTGACCTTGGTAGAGCTGCTCTAGTTGGTCGACGAGCCGCACGCGCCGCGGTTGCGCCTT

H  W  N  H  L  D  E  I  N  Q  L  L  G  V  R  G  A  N  A  E  -

P
                                            s
                                            t
                                            I
      GATCCGGTTCGCGGTGATCCGCACGCACGTGAACCGGCTCAAGCTGCAGGGCGTGTGA
1021  ------+---------+---------+---------+---------+---------  1077
      CTAGGCCAAGCGCCACTAGGCGTGCGTGCACTTGGCCGAGTTCGACGTCCCGCACACT

D  P  V  A  V  I  R  T  H  V  N  R  L  K  L  Q  G  V  *  -
```

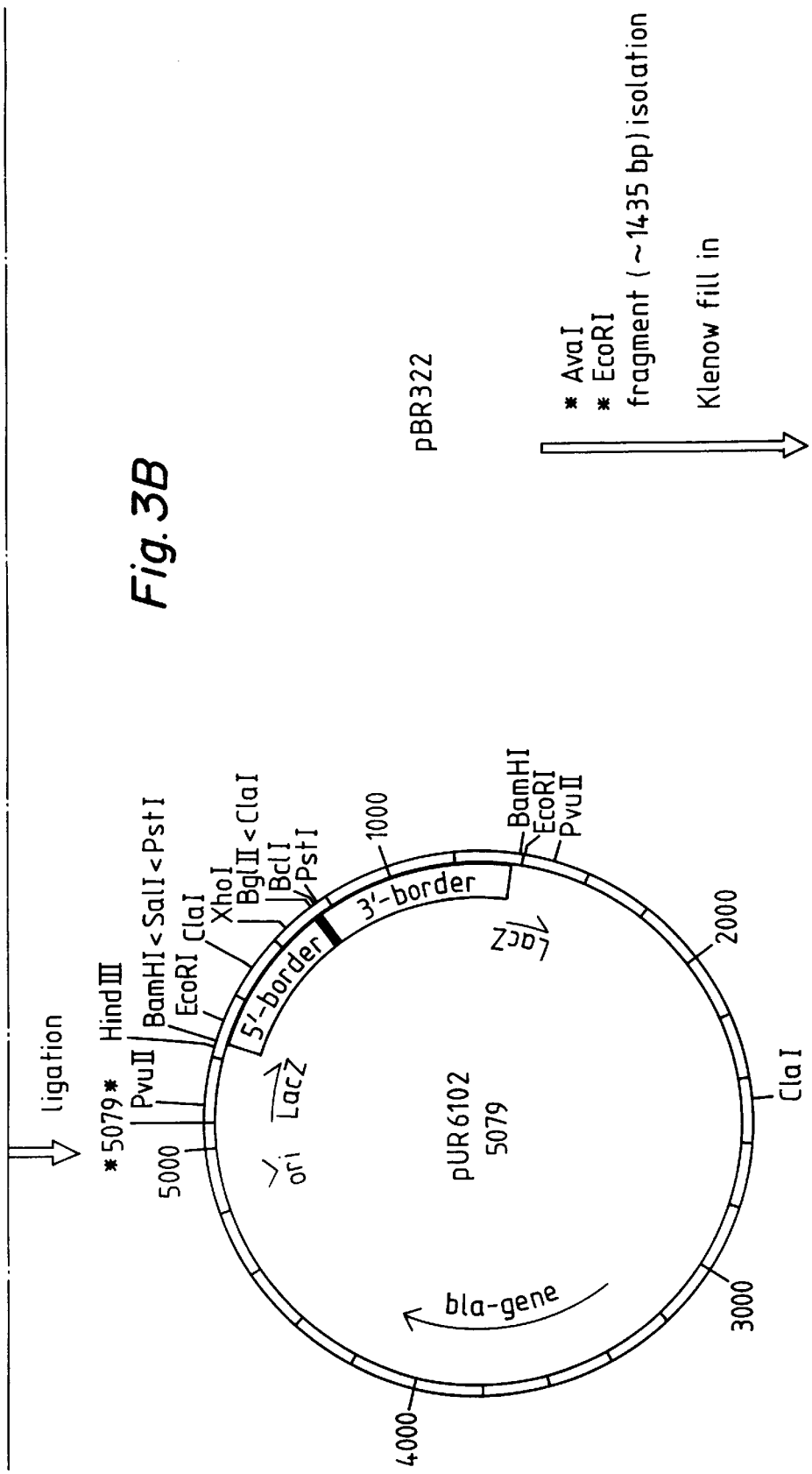

Fig. 5A

```
EcoRI
ClaI
          EcoRI
1 GAATTCATGGTTAGATCGATGCGTAGCCCTGTGTTGCAGCTAGAGCGGTCGCCATGGCATTA 60
  CTTAAGTACCAATCTAGCTACGCATCGGGACACAACGTCGATCTCGCCAGCGTACCCGTAAT

M  V  R  S  M  R  S  R  V  A  A  R  A  V  A  W  A  L  -
                                                           Pst I
                                                           I
61 GCTGTTTATGCCATTAGCTGGAGCAGCAGGATTAACAATGGCTGCGTCTCCTGCAGCGGTC 120
   CGACAATACGGTAATCGACCTCGTCGTCCTAATTGTTACCGACGCAGAGGACGTCGCCAG

A  V  M  P  L  A  G  A  A  G  L  T  M  A  A  S  P  A  A  V  -
                                                  EcoO
```

Fig. 5B

```
                                                     R
                                                     V
    GCTGCTGACACATATGCAGCTACGAGATATCCTGTGATCTTGGTTCACGGTTTGGCAGGA
121 ------------+------------+------------+------------+------------+------------+ 180
    CGACGACTGTGTATACGTCGATGCTCTATAGGACACTAGAACCAAGTGCCAAACCGTCCT

A  A  D  T  Y  A  A  T  R  Y  P  V  I  L  V  H  G  L  A  G  -

ACGGACAAGTTTGCCAATGTCGTTGACTACTGGTATCCAGTCAGATCTTCAATCT
181 ------------+------------+------------+------------+------------+------------+ 240
    TGCCTGTTCAAACGGTTACAGCAACTGATGACCATACCATAGGTCAGTCTAGAAGTTAGA

T  D  K  F  A  N  V  V  D  Y  W  Y  G  I  Q  S  D  L  Q  S  -

CACGGGAGCTAAGGTTTACGTGGCCAATTTGAGCGGATTCCAGTCTGACGATGGCCCAAAC
241 ------------+------------+------------+------------+------------+------------+ 300
    GTGCCCTCGATTCCAAATGCACCGGTTAAACTCGCCTAAGGTCAGACTGCTACCGGGTTTG

```
                    P v u I
                    I
       GGCCGGGGTGAACAGCTGCTTGCCTACGTCAAACAAGTACTTGCAGCTACGGGAGCTACG
301    ----------+---------+---------+---------+---------+---------+  360
       CCGGCCCACTTGTCGACGAACGCATGCAGTTTGTTCATGAACGTCGATGCCCTCGATGC

G   R   G   E   Q   L   L   A   Y   V   K   Q   V   L   A   A   T   G   A   T   -

AAGGTCAACTTGATCGGCCACTCTCAAGGTGGCCTTACATCTAGATACGTTGCTGCCGTG
361    ----------+---------+---------+---------+---------+---------+  420
       TTCCAGTTGAACTAGCCGGTGAGAGTTCCACCGGAATGTAGATCTATGCAACGACGGCAC

K   V   N   L   I   G   H   S   Q   G   G   L   T   S   R   Y   V   A   A   V   -

GCTCCTCAGTTGGTCGCCAGCGTTACTACGATCGGTACGCCTCACAGAGGCTCTGAGTTC
421    ----------+---------+---------+---------+---------+---------+  480
       CGAGGAGTCAACCAGCGGTCGCAATGATGCTAGCCATGCGGAGTGTCTCCGAGACTCAAG

```
       GCTGACTTTGTGCAAGACGTCTTGAAGACTGACCCAACAGGACTTTCGTCGACGGTTATT
481    ------+---------+---------+---------+---------+---------+    540
       CGACTGAAACACGTTCTGCAGAACTTCTGACTGGGTGTCCTGAAAGCAGCTGCCAATAA

A  D  F  V  Q  D  V  L  K  T  D  P  T  G  L  S  S  T  V  I

GCGGCTTTCGTTAACGTTTTCGGCACATTGGTTTCTAGCCTCTCACAATACGGATCAGGAC
541    ------+---------+---------+---------+---------+---------+    600
       CGCCGAAAGCAATTGCAAAAGCCGTGTAACCAAAGATCGGAGAGTGTTATGCCTAGTCCTG

A  A  F  V  N  V  F  G  T  L  V  S  S  H  N  T  D  Q  D

GCCCTTGCTGCAATTGCGCACGCTTACAACGGCTCAGACTGCCACGTATAATAGAAACTTT
601    ------+---------+---------+---------+---------+---------+    660
       CGGGAACGACGACGTTAACGCGTGCGAATGTTGCCGAGTCTGACGGTGCATATTATCTTTGAAA

A  L  A  A  L  R  T  L  T  T  A  Q  T  A  T  Y  N  R  N  F

CCAAGCCCTGGCTTGGGAGCTCCTGGTTCTTGTCAGAGGGGCCAGCTACAGAGACGGTT
661    ------+---------+---------+---------+---------+---------+    720
       GGTTCGGGACCGAACCCTCGAGGACCAAGAACAGTCTGCCCGGTCGATGTCTCTGCCAA

```
      PvuII
721  GGAGGCTCTCAGCACTTGCTTTACAGCTGGGGAGGTACCGCAATTCAACCAACGTCTACT
     ------+---------+---------+---------+---------+---------+  780
     CCTCCGAGAGTCGTGAACGAAATGTCGACCCCTCCATGGCGTTAAGTTGGTTGCAGATGA

G  G  S  Q  H  L  L  Y  S  W  G  G  T  A  I  Q  P  T  S  T

781  GTGTTGGGCCGTTACGGGAGCTACAGACACAAGCACTGGCACGCTTGATGTCGCGAATGTG
     ------+---------+---------+---------+---------+---------+  840
     CACAACCCGGCAATGCCCTCGATGTCTGTGTTCGTGACCGTGCGAACTACAGCGCTTACAC

V  L  G  V  T  G  A  T  D  T  S  T  G  T  L  D  V  A  N  V

841  ACGGACCCCTTCTACGTTGGCTCTTTTGGCTACGGGAGCGGTTATGATCAACCGTGCTTCT
     ------+---------+---------+---------+---------+---------+  900
     TGCCTGGGAAGATGCAACGAGAAAACCGATGCCCTCGCCAATACTAGTTGGCACGAAGA
                                                      XhoI
      T  D  P  S  T  L  A  L  L  A  T  G  A  V  M  I  N  R  A  S
```

Fig. 5F

```
     GGACAGAATGACGGCCTTGTCTCCGAGATGTAGCTCTCTTTGTTCGCCCAGTTATTTCTACG
901  ------------+------------+------------+------------+------------+------------+  960
     CCTGTCTTACTGCCGGAACAGAGGCTCTACATCGAGAAACAAGCGGGTCCAATAAAGATGC

G  Q  N  D  G  L  V  S  R  C  S  S  L  F  G  Q  V  I  S  T  -

TCTTACCACTGGAACCACTTGGATGAAATCAACCAACTTTTGGTGTGAGAGGGCCAAT
961  ------------+------------+------------+------------+------------+------------+  1020
     AGAATGGTGACCTTGGTGAACCTACTTTAGTTGGTTGAAAACCACACTCTCCCGGTTA

S  Y  H  W  N  H  L  D  E  I  N  Q  L  L  G  V  R  G  A  N  -

GCTGAGGACCCTGTTGCCCGTCATTCGTACGCCACGTCAACAGATTGAAACTTCAGGGAGTT
1021 ------------+------------+------------+------------+------------+------------+  1080
     CGACTCCTGGGACAACGGCAGTAAGCATGCCGTGCAGTTGTCTAACTTTGAAGTCCCTCAA

```
                              Bam    Hind
                       Pst I   H I    III
1081 TAATAGCTGCAGTTACTAGGATCCCTCATTACAAGCTT 1117
     ----------+---------+---------+-------
     ATTATCGACGTCAATGATCCTAGGAGTAATGTTCGAA
     *
```

Fig. 5H

```
                                                            P
                                                            s
                                                            t
                                                            I
     GCTGAGGACCCTGTTGCCGTCATTCGTACGCACGTCAACAGATTGAAACTGCAGGGAGTT
1021 ------+---------+---------+---------+---------+---------+ 1080
     CGACTCCTGGGACAACGGCAGTAAGCATGCCGTGCAGTTGTCTAACTTTGACGTCCCTCAA

A  E  D  P  V  A  V  I  R  T  H  V  N  R  L  K  L  Q  G  V  -

H
     i
     n
     d
     I
     I
     I
     TGAAGCTT
1081 -------- 1088
     ACTTCGAA
     *
```

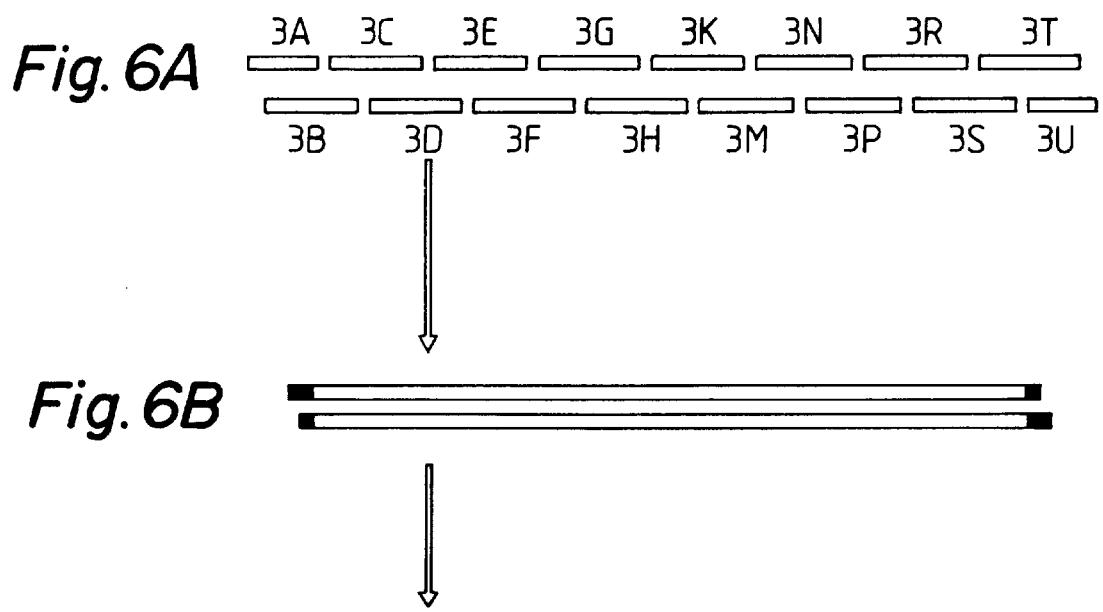

Fig. 6CI pUR 6028 (264 bp)

```
EcoRI      SalI              HpaI
<-  3A(25)      -X-   3C(33)                                -X-
AATTCGTAATGATAGTAAGTCGACGGTTATTGCGGCTTTCGTTAACGTTTTCGGCACAT

GCATTACTATCATTCAGCTGCCAATAACGCCGAAAGCAATTGCAAAAGCCCGTGTA
<-              3B(33)                -X-              3D(33)

HgaI             FspI
                         -X-   3G(36)                       -X-
TGGTTTCTAGCTCTCACAATACGGATCAGGACGCCCTTGCTGCATTGCGCACGCTTACAA
        3E(33)                -X-   3F(36)

SacI
                                   -X-   3N(33)
ACCAAAGATCGAGAGTGTTATGCCTAGTCCTGCGGGAACGACGTAACGCGTGCGAATGTT

-X-   3M(33)
CGGCTCAGACTGCCACGTATAATAGAAACTTTCCAAGCGGCTTGGGAGCTCCTGGTT
        -X-   3K(33)

GCCGAGTCTGACGGTGCATATTATCTTTGAAAGGTTCGCGACCGAACCCTCGAGGACCAA
                                                            -X-
3H(36)                             3M(33)
```

Fig. 6C2

```
                                                        PvuII
              -X-         3R(36)                 -X-
CTTGTCAGACGGGGCCAGCTACAGAGACGGTTGGAGGCTCTCAGCACTTGCTTTACAGCT
GAACAGTCTCTGCCCCGGTCGATGTCTCTGCCAACCTCCGAGAGTCGTGAACGAAATGTCGA
              3P(33)              -X-                    3S(36)
     KpnI          HindIII
     3T(35)       ->
GGGGAGGTACCTTACTATCATTACA
CCCCTCCATGGAATGATAGTAATGTTCGA
  -X-     3U(24)             ->
```

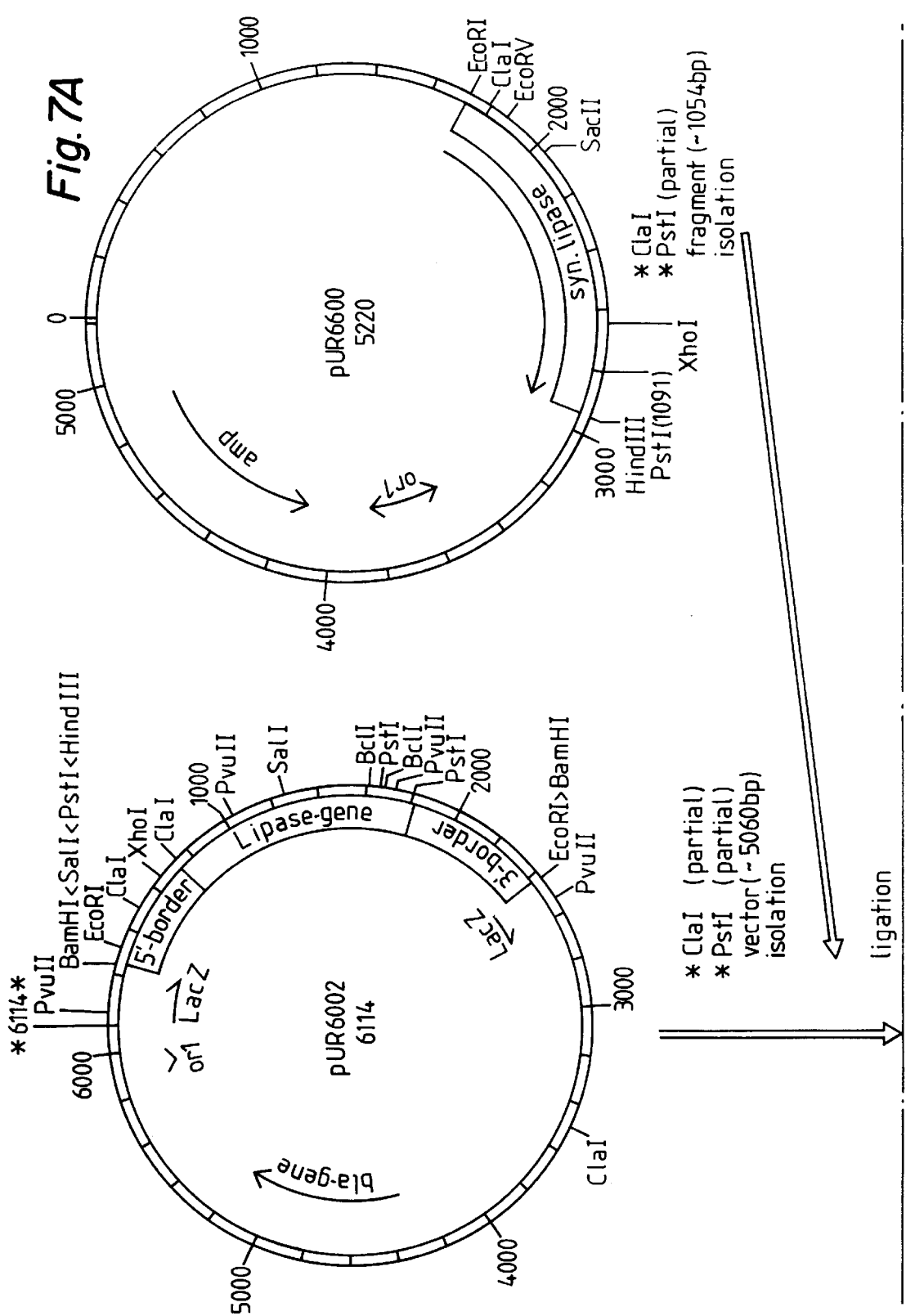

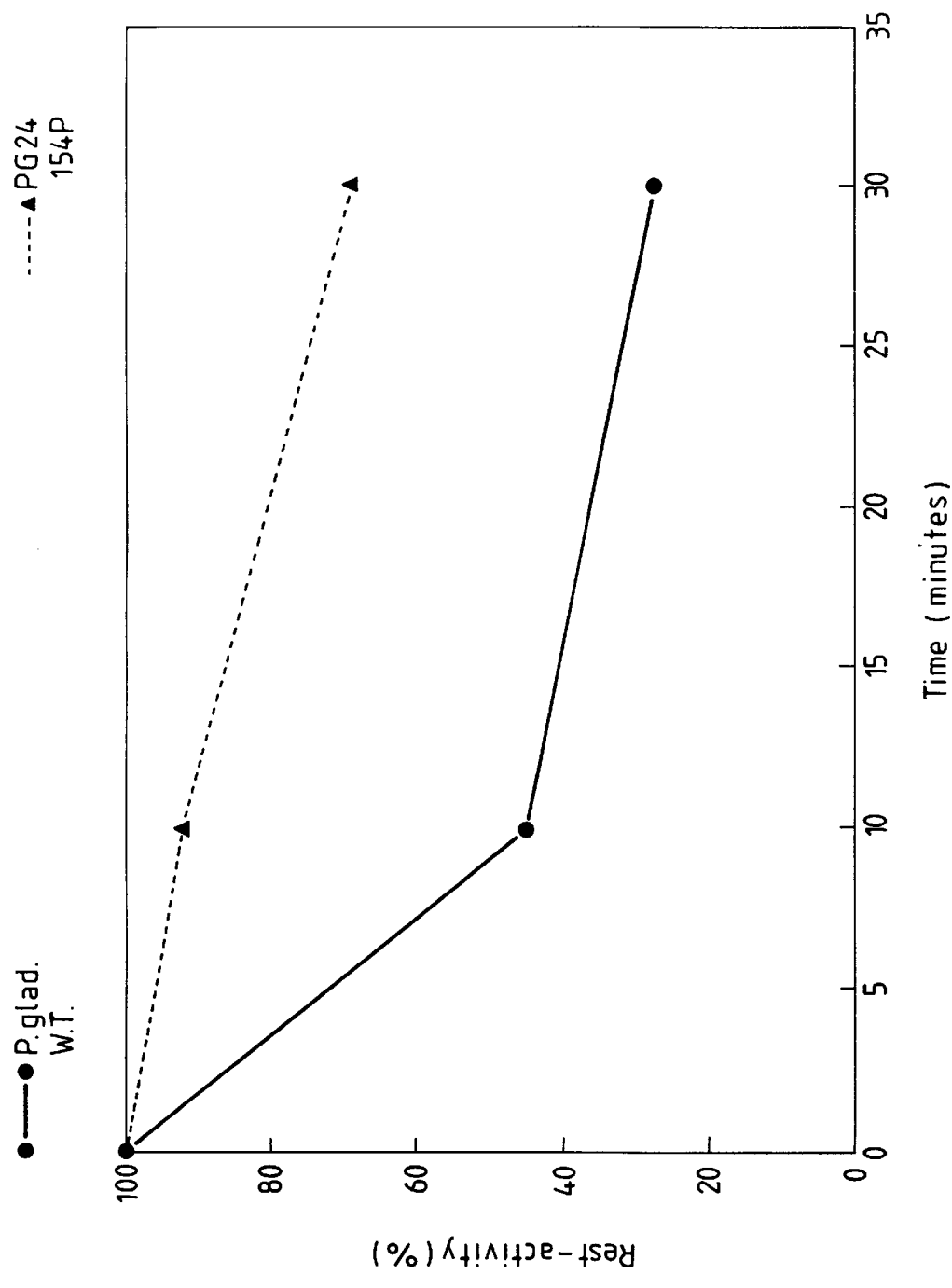

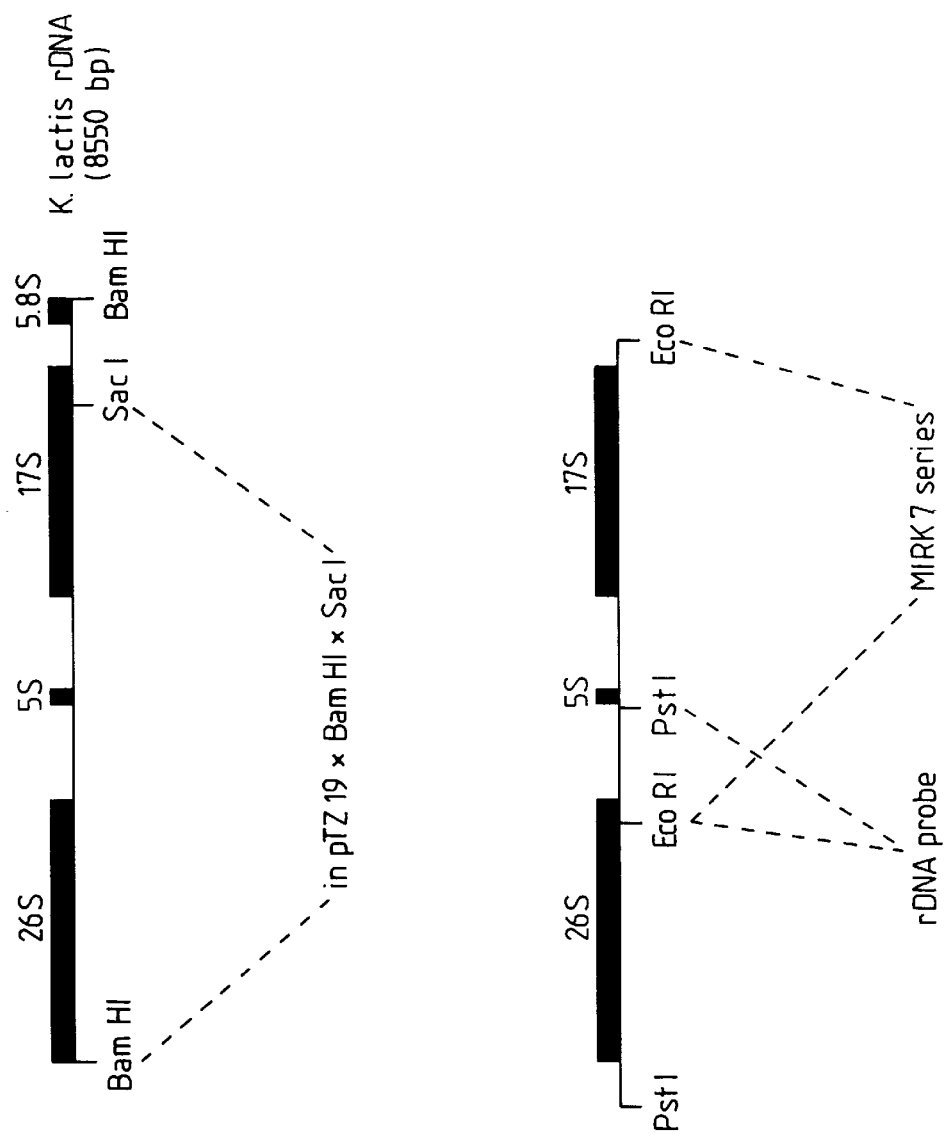

PROCESS FOR PREPARING A PROTEIN BY A FUNGUS TRANSFORMED BY MULTICOPY INTEGRATION OF AN EXPRESSION VECTOR

This is a continuation of application Ser. No. 08/364,010 filed Dec. 27, 1994, pending; which is a continuation of application Ser. No. 07/781,130 filed Jan. 7, 1992, now abandoned; which is filed under 35 U.S.C. 371 as a national stage application of PCT/EP90/01138 filed Jul. 9, 1990.

In a major aspect, the invention relates to a process for preparing a, homologous or heterologous, protein by a yeast, transformed by multicopy integration of an expression vector into the genome of the yeast, said expression vector containing both an "expressible gene" encoding said protein and a so-called "deficient selection marker needed for the growth of the yeast in a specific medium".

Although most experiments have been carried out with yeasts, it is envisaged that the invention is also applicable to moulds. Therefore in this specification in addition of either yeast or mould the term "fungus", or its plural form "fungi", will be used which covers both yeasts and moulds.

In this specification the expression "expressible gene" means a structural gene encoding a protein, either homologous or heterologous to the host organism, in combination with DNA sequences for proper transcription and translation of the structural gene, and optionally with secretion signal DNA sequences, which DNA sequences should be functional in the host eukaryote.

In this specification the expression "deficient selection marker needed for the growth of the yeast or mould in a specific medium" is used for a marker gene containing a promoter and a structural gene encoding a polypeptide or protein, said polypeptide or protein either being needed for the production of an ingredient, such as amino acids, vitamins and nucleotides, which ingredient is essential for the growth of the yeast or mould; in this specification such ingredient is also called "essential nutrient", or being needed for the protection of the cell against toxic compounds, such as antibiotics or $Cu^{2+}$ ions, present in the medium, provided that the deficient selection marker results either in sub-optimal de novo synthesis of said polypeptide or protein, which in turn results in a sub-optimal production of the essential ingredient or in sub-optimal protection against said the toxic compound, respectively, or in de novo synthesis of a modification of said polypeptide or protein having a sub-optimal efficiency in the production of said essential ingredient or in sub-optimal protection against said toxic compound, respectively.

Thus the word "deficient" is used to indicate both the sub-optimal synthesis of the polypeptide or protein, and the production of a polypeptide or protein having sub-optimal efficiency in the actions for the cell as mentioned above.

Examples of such marker genes include auxotrophic markers such as the LEU2, the TRP1 and the URA3 genes, antibiotic resistance genes such as the G418 resistance gene and the chloramphenicol resistance gene, and the gene encoding the enzyme catalase which can protect the cell against $H_2O_2$.

BACKGROUND OF THE MULTICOPY INTEGRATION ASPECT OF THE INVENTION

An example of a so-called "deficient selection marker needed for the growth of the yeast" is the LEU2d gene described by Kingsman c.s. (reference 1), who described the development of a multicopy integrative vector which was dispersed throughout the genome using the transposable Ty element Ty1-15 (reference 2). The element was engineered to contain two selectable markers, TRP1 (reference 3) and LEU2 from pMA3a, and the PGK expression signals from pMA91 (reference 4) with an IFN-$\alpha_2$ coding sequence (reference 5). A single copy of the engineered Ty was integrated into the genome using a linear fragment to stimulate recombination across the ends of the element and thereby replacing an endogenous element. Transformants were selected for the TRP1 marker. Few transformants were obtained by selecting for LEU2 as insufficient enzyme was produced by a single copy of this gene. The transformant was then grown in decreasing concentrations of leucine to select for an increase in the copy number of the LEU2 gene, presumably by spread of the Ty element throughout the genome by gene conversion and transposition (reference 6). A strain was constructed which produced $8 \times 10^5$ molecules of IFN per cell; this being intermediate between yields from single copy ARS/CEN vectors ($10^5$ molecules/cell) and from multicopy vectors such as pMA91 ($6 \times 10^6$ molecules/cell).

For a practical stable production system with a transformed yeast the use of Ty elements has certain disadvantages.

For example, Ty elements are homologous to retroviral sequences, which are more or less suspect materials for production of a protein suitable for products for human consumption or in the preparation thereof. Thus it is preferable to find solutions whereby these more or less suspect materials are not used.

Another disadvantage is their property of being transposable elements. This has the consequence that an appreciable risk exists that the resulting strain is not genetically stable, because the transposable TY elements integrated in the chromosome of the yeast can transpose and integrate at other sites of the genome which has negative implications for the production process and can give problems in obtaining clearance from responsible companies and the authorities.

In view of their retroviral properties Ty elements may result in virus-like particles. This is highly undesirable for practical production processes, because instability of genetically modified organisms should be avoided.

Ty elements only occur in the yeast Saccharomyces cerevisiae. Therefore it is doubtful, whether they can be used for other yeasts or even moulds. It is unknown whether transposable elements occurring in other organisms can be used in a similar way. But even if they could, they have the same disadvantages as indicated above.

The copy number obtained with Ty integration is about 20–30 with a single maximum of about 40 copies per cell. A higher number of 100–300 copies per cell would be highly advantageous for commercial production systems, as higher copy numbers, in general, will result in higher expression levels.

Therefore a need exists for other systems by which multicopy integration of heterologous genes in fungi such as yeast and moulds can be achieved.

SUMMARY OF THE MULTICOPY INTEGRATION ASPECT OF THE INVENTION

It has now been found that stable multicopy integration in *S. cerevisiae* can be obtained by use of an expression vector containing both an expressible heterologous gene and a "deficient selection marker needed for the growth of the yeast" as above defined and additionally a ribosomal DNA sequence, of which the ribosomal DNA sequence enables stable multicopy integration of said expression vector in the ribosomal DNA locus of the yeast genome. Surprisingly it appeared to be possible with such a system to obtain multicopy integration of over 200 copies per cell, which were stable over more than 70 generations in both batch and continuous cultures.

It has surprisingly been found that not only the known LEU2d system but also other "deficient markers" can be used, in particular a TRP1d or URA3d gene.

It has further been found that this technique can also be applied to other yeasts, in particular of the genera Hansenula and Kluyveromyces.

Thus the principle of using an expression vector containing a "deficient marker" combined with a ribosomal DNA sequence for obtaining multicopy integration in a yeast as disclosed above appears to have a more general application, for example for other yeasts like Pichia or moulds e.g. belonging to the genera Aspergillus, Rhizopus or Trichoderma, in particular if the multicopy integration vectors contain ribosomal DNA originating from the host organism. Thus this principle is applicable for fungi in general.

The multicopy integration aspect of the present invention provides a process for preparing a heterologous protein, e.g. a lipase, by a eukaryote transformed by multicopy integration of an expression vector into the genome of the eukaryote, said expression vector containing both an expressible gene encoding said heterologous protein and a so-called "deficient selection marker needed for the growth of the eukaryote", in which process said expression vector contains ribosomal DNA sequences enabling multicopy integration of said expression vector in the ribosomal DNA locus of the eukaryote genome.

It has further been found that an expression vector as herein before described can be stably maintained at a high copy number, when a fungus transformed according to the invention is grown in a so-called "complete" or non-selective medium, which contains all the ingredients necessary for growth of the fungus. Normally one would expect that de novo synthesis is not required due to the presence of the essential ingredient in the medium, which would result in decreasing the proportion of multicopy-integrated yeast cells in the total yeast population and thus would lead to a decreased production of the desired polypeptide or protein. Surprisingly, despite a situation in which de novo synthesis is not required, the multicopy integration is stably maintained and the polypeptide or protein was produced in relatively large quantities.

Although the invention is not limited by any explanation, it is believed that the effects observed are based on the following theory. For unknown reasons it seems that in such a system the uptake of the essential ingredient is limited. Therefore, de novo synthesis is still needed when the fungus is grown at a growth-rate above a certain minimum value. This will result in a selection advantage for those cells which have a high copy number of the "deficient marker". Possibly the active uptake of the essential ingredient, e.g. leucine is negatively influenced by the presence of other components in the medium, such as peptides and valine.

Thus, in general, the process can be described as a process in which said transformed fungus is grown in a medium containing said essential ingredient at a concentration below a certain limit whereby the uptake of said ingredient is rate-limiting, so that de novo synthesis of said ingredient is required for a growth-rate above a certain minimum value.

An example of a complete medium is an industrially applied growth medium such as molasses, whey, yeast extract and combinations thereof.

Another embodiment of this invention is the fermentative production of one of the various forms of enzymes described above or related hosts. Such a fermentation can either be a normal batch fermentation, a fed-batch fermentation or a continuous fermentation. The selection of which process has to be used depends on the host strain and the preferred down stream process. According to this embodiment it is preferred that the enzyme is secreted by the microorganism into the fermentation broth, whereafter the enzyme can be recovered from the broth by first removal of the cells either by filtration or by centrifugation.

In a further aspect, the invention relates to enzymes to recombinant DNA techniques applicable for example for their modification and production.

In particular embodiments this aspect of the invention relates to the production of modified enzymes or modified enzymes, especially modified lipases. Thus this aspect as described below provides inter alia techniques for production of lipase, e.g. lipases of the genus Pseudomonas, e.g. lipase from *P. glumae* (alias *P. gladioli*) and further provides genetically modified forms of such lipases.

SPECIFIC EMBODIMENTS OF THE MULTICOPY ASPECT OF THE INVENTION

More specifically the invention provides a process for preparing a, homologous or heterologous, protein by a eukaryote transformed by multicopy integration of an expression vector into the genome of a host eukaryote, said expression vector containing both an "expressible gene" as herein before defined encoding said homologous or heterologous protein and a so-called "deficient selection marker needed for the growth of the yeast or mould in a specific medium" as herein before defined, wherein said expression vector contains ribosomal DNA sequences enabling multicopy integration of said expression vector in the ribosomal DNA locus of the eukaryote genome. Preferably said deficient selection marker is a LEU2d gene, a TRP1d gene, or a URA3d gene. The eukaryote can be a fungus such as a yeast, preferably one of the genera Saccharomyces, Kluyveromyces or Hansenula, or a mould, preferably one of the genera Aspergillus, Rhizopus and Trichoderma. In a preferred process said transformed eukaryote is grown in a medium containing an ingredient, which is essential for the growth of the eukaryote, at a concentration whereby the uptake of said ingredient is rate-limiting, so that de novo synthesis of said ingredient is required for a growth-rate above a certain minimum value which value depends on the host organism and the process conditions. Preferably such medium is a so-called "complete" or non-selective medium, which contains all the ingredients necessary for growth of the eukaryote, for example an industrially applied growth medium, such as molasses, whey, yeast extract and mixtures thereof.

In order to obtain sufficient production of a selected protein in the process according to the invention it is preferred that the transformed eukaryote contains the gene or genes required for expression of said protein in a multimeric form in one of its chromosomes in, or directly linked to, a locus coding for a ribosomal RNA while at the same locus also multimeric copies of a deficient gene encoding a protein required in the biochemical pathway for the synthesis of said "essential nutrient" are present. Examples of such expressible gene are those encoding an enzyme, preferably a hydrolytic enzyme, in particular a lipase, or a genetically modified form of such enzyme. Particularly preferred lipases that can be produced with a process according to the present invention are lipases that cross-react with antisera raised against a lipase from *Chromobacter viscosum* var *lipolyticum* NRRL B-3673, or with antisera raised against lipase from Alcaligenes PL-679, ATCC 31371 or FERM-P 3783, or with antisera raised against a lipase from *Pseudomonas fluorescens* IAM 1057, and modified forms of such cross-reacting lipase. A specially preferred lipase is encoded by a gene having the nucleotide sequence given in FIG. 2 or any nucleotide sequence encoding the same amino acid sequence as specified by that nucleotide sequence or encoding modified forms of this amino acid sequence resulting in a lipase with a better overall performance in detergents systems than the original lipase. The transformed eukaryote used in a process according to the invention is preferably a eukaryote being deficient for the synthesis of an "essential nutrient" as herein before defined and whereby the deficient selection marker can contribute to complementation of the synthesis of the "essential nutrient". The deficiency of the parent strain can be achieved by replacement of a gene coding for an enzyme effective in the biosynthetic pathway of producing said essential nutrient. It is particularly advantageous if the enzyme, for which the parent strain is deficient, catalyses a reaction in a part of the biosynthetic pathway that is not branched until the essential nutrient is formed. Examples of essential nutrients are amino acids, nucleotide or vitamins, in particular one of the amino acids leucine, tryptophan or uracil.

Another embodiment of the invention is a process as described above, in which the expression vector contains (i) a ds ribosomal DNA or part thereof e.g. a ds DNA sequence that codes for a ribosomal RNA, and (ii) a DNA sequence containing in the 5'→3' direction in the following order:

(ii)(a) a powerful promoter operable in the host organism, (ii)(b) optionally a signal sequence facilitating the secretion of said protein from the host eukaryote, (ii)(c) a structural gene encoding the protein, (ii)(d) an efficient terminator operable in the host eukaryote, in addition to the sequences normally present in a vector.

The ribosomal DNA can be ribosomal DNA's occurring in moulds, in particular moulds of the genera Aspergillus, Rhizopus and Trichoderma, or those occurring in yeasts, in particular yeasts of the genera Saccharomyces, Kluyveromyces, Hansenula and Pichia.

Experiments have shown that the best results are obtained when the vector has approximately the same length as one ribosomal DNA unit of the host organism. For example, if the ribosomal unit in the chromosomal DNA is about 9 kb, vectors of about 14 kb or 5 kb were not stably maintained, but vectors of about 8–10 kb were stably maintained.

The promoter controlling the expressible gene is preferably (i) the Gal7 promoter, the GAPDH promoter, or the PGK promoter, if the host belongs to the genus Saccharomyces, (ii) the inulinase promoter, the PGK promoter or the LAC4 promoter, if the host belongs to the genus Kluyveromyces, (iii) the DHAS promoter or MOX promoter, if the host belongs to the genus Hansenula, (iv) the glucoamylase promoter, glucose-oxidase promoter or the GAPDH promoter, if the host belongs to a mould of the genus Aspergillus, or (v) the cellulase promoter or the GAPDH promoter, if the host belongs to moulds of the genera Rhizopus and Trichoderma.

If the structural gene encodes an oxidase, the host cell preferably belongs to the genera Hansenula or Pichia or Aspergillus.

Another preferred embodiment relates to a process in which the expressible structural gene encodes the light or heavy chain of an immuno-globulin or preferably both genes, or part of the light or heavy chain of an immunoglobulin, preferably that part coding for what normally is called FAB fragment, or that part thereof that codes for the variable regions. Related to this embodiment is the use of a gene or genes modified by genetic engineering resulting in modified immunoglobulins or immunoglobulins with catalytic activity (Abzymes).

A preferred expression vector additionally contains a deficient gene coding for an enzyme that has been disrupted or deleted from the chromosome of the host cell, more preferably one encoding an enzyme effective in the biosynthetic pathway of producing an essential nutrient, such as an amino acid like leucine, tryptophan or uracil, a nucleotide or a vitamin. A process according to the invention can be carried out as a normal batch fermentation, a fed-batch fermentation, or a continuous fermentation. It is preferred that the medium contains the essential nutrient in such a concentration that at least 20, but preferably at least 50, copies of the deficient gene are maintained in the chromosome, said deficient gene encoding an enzyme involved in the biosynthesis of that essential nutrient. Good yields of the protein to be produced by the transformed eukaryote can be obtained when the growth rate of the host is between 20 and 100%, preferably between 80 and 100%, of the maximum growth rate of a similar host not deficient for said essential nutrient under the same fermentation conditions.

BACKGROUND OF THE LIPASE ASPECT OF THE INVENTION

Lipases and proteases are both known as ingredients of detergent and cleaning compositions. Proteases are widely used.

Examples of known lipase-containing detergent compositions are provided by EPA 0 205 208 and EPA 0 206 390 (Unilever) which relates to a class of lipases defined on basis of their immunological relationship and their superior cleaning effects in textile washing. The preferred class of lipases contains lipases from a.o. *P. fluorescens, P. gladioli* and Chromobacter species.

EPA 0 214 761 (NOVO) and EPA 0 258 068 (NOVO), each give detailed description of lipases from certain microorganisms, and also certain uses of detergent additives and detergent compositions for the enzymes described.

EPA 0 214 761 gives detailed description of lipases derived from organisms of the specimen *P. cepacia,* and certain uses therefor. EPA 0 258 068 gives detailed description of lipases derived from organisms of the genus Thermomyces (previous name Humicola) and certain uses therefor.

A difficulty with the simultaneous incorporation of both lipases and proteases into detergent compositions is that the protease tends to attack the lipase.

Measures have been proposed to mitigate this disadvantage.

One such attempt is represented by EPA 0 271 154 (Unilever) wherein certain selected proteases with isoelectric points less than 10 are shown to combine advantageously with lipases.

Another attempt is described in WO 89/04361 (NOVO), which concerns detergent compositions containing a lipase from Pseudomonas species and a protease from Fusarium or proteases of subtilisin type which has been mutated in its amino acid sequence at positions 166, 169, or 222 in certain ways. It was reported that there was some reduction in the degree of attack upon the lipase by the particular proteases described.

THE LIPASE ASPECT OF THE INVENTION

The invention in one of its aspects provides lipases produced by recombinant DNA techniques, which carry at least one mutation of their amino acid sequences, conferring improved stability against attack by protease. For example, the invention provides lipases showing immunological cross-reactivity with antisera raised against lipase from *Chromobacter viscosum* var. *lipolyticum* NRRL B-3673 or against lipase from *Pseudomonas fluorescens* IAM 1057 and produced by an artificially modified microorganism containing a gene made by recombinant DNA techniques which carries at least one mutation affecting the amino acid sequence of the lipase thereby to confer upon the lipase improved stability against attack by protease.

The artificially modified microorganisms include *Escherichia coli, Pseudomonas aeruginosa, P. putida* and *P. glumae* in which the original gene for the lipase has been deleted, Bacillus subtilis and various varieties of the genus Aspergillus, Rhizopus and Trichoderma, *Saccharomyces cerevisiae* and related species, *Hansenula polymorpha,* Pichia and related species, Kluyveromyces marxianus and related species. As these host cells reflect a broad range of different micro-organisms other microorganisms not described in detail in the examples can be used as well as host cells.

The modified lipase can bring advantage in both activity and stability when used as part of a detergent or cleaning composition.

In such lipase, the mutation can for example be selected from (a) introduction (e.g. by insertion or substitution) of one or more proline residues at a location otherwise vulnerable to proteolytic attack;

(b) an increase of the net positive charge of the lipase molecule (e.g. by insertion of positively-charged amino acid residues or by substitution of neutral or negatively-charged amino acid residues);

(c) introduction (e.g. by insertion or substitution) of a combination of amino acid residues of the lipase capable of becoming glycosylated in the selected host cell, thereby improving the stability of the glycosylated lipase against proteolytic attack.

Also provided by the invention is a method for the production of a modified microorganism capable of producing an enzyme by recombinant DNA techniques, characterized in that the gene coding for the enzyme that is introduced into the microorganism is fused at its 5'-end to a (modified) pre-sequence.

In particular embodiments of the invention, the gene of bacterial origin is introduced with an artificial presequence into eukaryotic organisms.

Accordingly, in certain aspects the invention provides artificially modified microorganisms containing a gene coding for an enzyme and able to produce that enzyme derived originally from one of the organisms mentioned above or a modified form of such enzyme by use of recombinant DNA techniques and fermentative processes for enzyme production based on such artificially modified microorganisms.

The fermentation processes in themselves apart from the special nature of the microorganisms can be based on known fermentation techniques and commonly used fermentation and down stream processing equipment.

According to a further aspect of the present invention it is found that modified (mutant) lipases from Pseudomonas or another of the preferred class of lipases, with amino acid sequence modification(s) chosen to increase the stability of the enzyme to protease digestion are of value in detergent and cleaning compositions, especially for example in combination with proteases, e.g. proteases of the subtilisin type.

A suitable and presently preferred example of such a mutation is embodied in a mutant lipase from *Pseudomonas glumae* with a His 154 Pro mutation, which is believed to replace a site vulnerable to protease digestion in one of the loops of the tertiary structure of the lipase with a less vulnerable site.

According to a further aspect of the present invention it is found that modified (mutant) lipases from Pseudomonas or another of the preferred class of lipases with amino acid sequence modification(s) chosen to increase the net positive charge of the lipase and its pI, are of value in detergent and cleaning compositions, especially for example in combination with proteases, e.g. proteases of the subtilisin type.

Suitable mutations include for example the deletion of negatively charged residues (e.g. aspartate or glutamate) or their substitution by neutral residues (e.g. serine, glycine and proline) or by the substitution of neutral or negative residues by positively-charged amino acid residues (e.g. arginine or lysine) or the insertion of positively-charged residues.

Suitable examples of such mutations increasing the net positive charge and pI include D157R, D55A and I110K. Suitable examples of the introduction (e.g. by insertion or substitution) of a combination of amino acid residues capable of becoming glycosylated in the selected host and thereby improving its stability against proteolytic attack are given by mutations D157T and insertion of G between N155 and T156.

To avoid over-glycosylation or to remove glycosylation on less desirable positions the potential glycosylation sites of the original lipase can be removed.

Within the preferred class of lipases the lipase produced by *Pseudomonas glumae* (formerly and more usually called *Pseudomonas gladioli*) is a preferred basis for the processes and products of this invention. Neither the amino acid sequence nor the nucleotide sequence-of the gene coding for the preferred lipase was previously known. The present inventors have isolated the gene coding for the preferred lipase of this bacterium as will be illustrated below.

The invention also provides genetic derived material from the introduction of this gene into cloning vectors, and the use of these to transform new host cells and to express the lipase gene in these new host cells.

Usable heterologous new host cells include for example *Escherichia coli, Pseudomonas aeruginosa, P. putida.* Also *P. glumae* in which the original lipase gene has been deleted is a suitable host. The preferred host systems for large scale production are *Bacillus subtilis, Saccharomyces cerevisiae* and related species, Kluyveromyces marxianus and related species, *Hansenula polymorpha,* Pichia and related species and members of the genera Aspergillus, Rhizopus and Trichoderma. Also suitable hosts for large scale production are Gram (−) bacteria specially selected and/or modified for efficient secretion of (mutant) lipases. As these host cells reflect a broad range of different microorganisms other microorganisms not described in detail in the examples can be used as well as host cells.

Another embodiment of the invention relates to vectors able to direct the expression of the nucleotide sequence encoding a gene coding for an enzyme as described above in one of the preferred hosts preferably comprise:

(a) ds DNA coding for mature enzyme or pre-enzyme directly down stream of a (for the selected host preferred) secretion signal; in cases where the part of the gene that should be translated does not start with the codon ATG, an ATG should be placed in front. The translated part of the gene should always end with an appropriate stop codon;

(b) an expression regulon (suitable for the selected host organism) situated upstream of the plus strand of the ds DNA of (a);

(c) a terminator sequence (suitable for the selected host organism) situated down stream of the plus strand of the ds DNA of (b);

(d) nucleotide sequences which facilitates integration, preferably multicopy integration, of the ds DNA of (a–c) into the genome of the selected host which host is deficient for an essential nutrient. The nucleotide sequence that facilitates multicopy integration is ds ribosomal DNA or at least part of this sequence. Moreover a ds DNA sequence containing the deficient gene coding for the enzyme that is absent in the host cell has to be present on the integration vector, and (e) optionally a ds DNA sequence encoding proteins involved in temporary inactivation or unfolding and/or in the maturation and/or secretion of one of the precursor forms of the enzyme in the host selected.

The invention will be illustrated by the following examples.

Example 1 Isolation and characterization of the gene encoding (pre)-lipase of *P. glumae*.

Example 2 Construction of the lipase negative *P. glumae* strains PG2 and PG3.

Example 3 Construction of a synthetic gene encoding *P. glumae* (pre)-lipase.

Example 4 Introduction of the (wild type) synthetic lipase gene in the lipase negative *P. glumae* PG3.

Example 5 Production of mutant lipase genes and their introduction in PG3.

Example 6 Expression of the synthetic lipase genes in *Saccharomyces cerevisiae* using autonomously replicating smids.

Example 7 Expression of synthetic lipase genes in *Saccharomyces cerevisiae* using multicopy integration.

Example 8 Production of guar α-galactosidase in *Saccharomyces cerevisiae* using multicopy integration.

Example 9 Multicopy integration in *Saccharomyces cerevisiae* using other deficient selection markers.

Example 10 Stability of the multicopy integrant in continuous cultures.

Example 11 Parameters affecting the stability of multicopy integrant SU50B

Example 12 Expression of the synthetic lipase genes in *Hansenula polymorpha*.

Example 13 Production of guar α-galactosidase in *Hansenula polymorpha* using multicopy integration.

Example 14 Multicopy integration in Kluyveromyces.

Examples 1–6 and 12 relate to the isolation, cloning and expression of lipase genes in the yeasts *Saccharomyces cerevisiae* and *Hansenula polymorpha* using plasmid vectors.

Example 7 relates to the expression of a lipase gene in the yeast *Saccharomyces cerevisiae* after multicopy integration of an expression vector according to the invention.

Examples 9–11 relate to other aspects of the multicopy integration.

Examples 8 and 13 relate to the expression of guar α-galactosidase in the yeasts *Saccharomyces cerevisiae* and *Hansenula polymorpha*.

Example 14 shows that multicopy integration can be achieved in a Kluyveromyces yeast.

EXAMPLE 1

ISOLATION AND CHARACTERIZATION OF THE GENE ENCODING (PRE)-LIPASE OF *P. glumae*

Isolation of *P. glumae* chromosomal DNA

Cells of a 15 ml overnight culture in LB medium were collected by centrifugation (Sorvall HB4 rotor, 10,000 rpm for 10 min). The cell pellet was stored at −20° C. overnight.

After thawing the cells were re-suspended in 10 ml SSC (0.15M NaCl, 0.015M Na-citrate) containing 2 mg/ml lysozyme. After incubation for 30 min at 37° C., 0.5 ml of 10% SDS was added, followed by an incubation at 70° C. for 10 min. After cooling to 45° C., 1 ml proteinase K (2 mg/ml Tris-HCl pH 7.0, pre-incubated for 30 min at 45° C.) was added and the mixture was incubated at 45° C. for another 30 min. Next, 3.2 ml 5M $NaClO_4$ was added, followed by two extractions with 15 ml $CHCl_3$/iso-$C_5H_{11}OH$ (24:1), each of which was followed by a centrifugation step (Sorvall HS4, 5,000 rpm/10 min). The DNA was precipitated from the supernatant by adding 10 ml ethanol. After a wash in 75% ethanol the DNA pellet was re-suspended in 2 ml $H_2O$.

Preparation of a gene bank

A DNA preparation of *P. glumae* was partially digested with the restriction enzyme Sau3A, as described by Maniatis (7). The cosmid vector c2RB (8) was digested to completion with SmaI and BamHI, both enzymes having one recognition site in the cosmid. Excess vector fragments were ligated, using T4 DNA ligase (in 50 mM Tris-HCl pH 7.5, 10 mM dithiothreitol (DTT), 10 mM MgCl2 and 0.5 mM rATP), with DNA fragments from *P. glumae*. The recombinant DNA thus obtained was packaged in phage particles as described by Hohn (9). The complete phage particles obtained this way were used to transform *E. coli* 1046 met, gal, lac, hsdR, phx, supE, hsdM, recA) by transfection.

5 ml fresh LB medium containing 0.4% maltose, was inoculated with 0.5 ml of a overnight culture of *E. coli* 1046 and incubated for 6 h. at 37° C. under continuous shaking. Before infection with phage particles, $MgCl_2$ and $CaCl_2$ were added to a final concentration of 10 mM. In a typical experiment 50 μl phage particles were mixed with 50 μl of cells and the mixture was incubated at 37° C. for 15 min; 100 μl LB medium was added and incubation at 37° C. continued for 30 min. The cells were plated directly an LB-agar plates containing 75 μg/ml ampicillin (Brocacef). After overnight growth at 37° C. ca. 300 colonies were obtained.

Oligonucleotide synthesis

As probes for the lipase encoding DNA fragment, we used oligonucleotides based on the sequences of the 24 N-terminal amino acids (see below), determined by Edman degradation, using an Applied Biosystems Gas Phase Protein Sequencer.

Based on the established amino acid sequence, all the possible nucleotide sequences encoding the amino acid sequence were derived. Deoxy-oligonucleotides containing all or part of the possible nucleotide sequences (so called mixed-probes) were synthesized on a DNA synthesizer (Applied Biosystems 380 A) using the Phosphoamidit technique (10). Oligonucleotides were purified on 16% or 20% polyacrylamide gels (7).

Radio-labeled oligonucleotide probes

Typically, 0.1–0.3 µg of the purified oligonucleotide was labelled by incubation for 30 minutes at 37° C. in 50 mM Tris-HCl pH 7.5, 10 mM MgCl$_2$, 0.1 mM EDTA, 10 mM DTT, 70 µCi gamma-$^{32}$P-ATP (3000 Ci/mmol, Amersham) and 10 units T4 polynucleotide kinase (Amersham) in a final volume of 15 µl. The reaction was terminated with 10 µl 0.5M EDTA pH 8.0 and passed through a Sephadex G25 column of 2.5 ml (disposable syringe) equilibrated with TE buffer (10 mM Tris-HCl pH 8.0 and 1 mM EDTA). Fractions of 250 µl were collected, from which the first two radioactive fractions, usually fractions 4 and 5, were pooled and used for hybridization.

Screening of the gene bank

From several packaging and transfection experiments, performed as described above, a total of ca 1000 separate colonies were obtained. These colonies were transferred to ELISA plates (Greiner, F-form) containing 150 µl LB-medium (100 µg ampicillin/ml)/well. After overnight growth at 37° C. duplicates were made using a home-made template, consisting of 68 pins, arranged to fit in the microtiter wells. To the wells of the masterplates 50 µl 50% glycerol was added, and after careful mixing with the aid of the template, these plates were stored at –80° C.

The duplicates were used to transfer the gene bank to nitro-cellulose filters (Millipore, type HATF, 0.45 µm, φ14 cm). To this end the cellulose filters were prewetted by laying them on LB-agar plates with 100 µg/ml ampicillin. After transfer of the bacteria with the aid of the template, colonies were grown overnight at 37° C.

The colonies on the filters were lysed by placing them on a stack of Whattman 3 MM paper, saturated with 0.5M NaOH, 1.5M NaCl for 15 min. After removal of excess liquid by placing the filters on dry paper, they were neutralised by placing them on a stack of 3 MM paper, saturated with 1M Tris-HCl pH 7.0, 1.5 mM NaCl for 2–3 min. Finally the filters were dunked into 10×SSC (1.5M NaCl, 0.15M Na-citrate) for 30 sec, air dried and baked at 80° C. under vacuum for 2 hours. Prior to (pre)hybridization the filters are washed extensively in 3×SSC, 0.1% SDS at 65° C. for 16–24 h with several changes of buffer. The washing was stopped when the colonies were no longer visible.

Pre-hybridization of the filters was performed in 5×SSC, 5×Denhardts (10×Denhardts=0.2% ficoll, 0.2% polyvinylpyrrolidone, 0.2% bovine serum albumin), 0.1% SDS, 50 mM sodium phosphate pH 7.5, 1% glycine, 100 µg/ml calf-thymus DNA (sheared and heat denatured), 500 µg/ml tRNA and 50% de-ionized formamide for 2 hours at 37° C.

Hybridization with a radio-active labelled (see above) mixed probe (vis02, 32 nucleotides) was performed in 5×SSC, 1×Denhardts, 0.1% SDS, 20 mM sodium phosphate pH 7.5, 100 µg/ml calf-thymus DNA, 500 µg/ml tRNA and 50% deionized formamide, for 16 h. at 39° C. After the hybridization, the filters are washed: 3×15 min with 6×SSC at room temperature, 1×15 min 2×SSC, 0.1% SDS and subsequently at a room temperature dependent on the properties of the oligonucleotide probe. For vis02 washing was extended for 15 min at 37° C. in preheated 0.1 SSC 0.1% SDS.

Upon screening the gene bank as described above, several cosmid clones were isolated. Clone 5G3 (hereinafter called pUR6000) was chosen for further investigations.

Sequencing of the lipase gene

DNA fragments resulting from digestion of pUR6000 with BamHI were ligated in plasmid pEMBL9 (11) which was also cleaved with BamHI and the obtained recombinant DNA was used to transform E. coli JM101 (12), with the CaCl$_2$ procedure and plated on LB-agar plates supplemented with X-gal and IPTG (7).

68 white colonies were transferred to microtiter plates and subjected to the same screening procedure as described for the cosmid bank. Several positive clones could be isolated. A representative plasmid isolated of one of these colonies is depicted in FIG. 1 and is referred to as pUR6002. Upon digesting this plasmid with EcoRI, two fragments were found on gel, ~4.1 kb and ~2.1 kb in length, respectively. Another plasmid, pUR6001, contained the BamHI fragment in the opposite orientation. After digestion with EcoRI, this plasmid resulted in fragments with a length of ~6.1 kb and ~70 bp, respectively.

In essentially the same way pUR6006 was constructed. In this case pUR6000 was digested with EcoRI after which the fragments were ligated in the EcoRI site of plasmid pLAFRI (13). After screening the transformants, a positive clone was selected, containing a EcoRI fragment of ~6 kb, designated pUR6006 (FIG. 1). The purified DNA of pUR6001 and pUR6002 was used for the establishment of the nucleotide sequence by the Sanger dideoxy chain termination procedure (14) with the modifications as described by Biggin et al. (15), using alpha-$^{35}$S-dATP (2000 Ci/mmol) and Klenow enzyme (Amersham), ddNTP's (Pharmacia-PL Biochemicals) and dNTP's (Boehringer). We also used the Sequenase kit (United States Biochemical Corporation), with substitution of the dGTP for 7-deaza-dGTP. The sequencing reaction products were separated on a denaturing polyacrylamide gel with a buffer gradient as described by Biggin et al. (15).

The complete nucleotide sequence (1074 bp) of the P. glumae lipase (hereafter also called: glumae lipase) gene is given in FIG. 2.

The nucleotide sequence contains an open reading frame encoding 358 amino acid residues followed by a stop codon.

The deduced amino acid sequence is shown in the IUPAC one-letter notation below the nucleotide sequence in FIG. 2.

The NH$_2$-terminal amino acid sequence of the lipase enzyme as purified from the P. glumae culture broth has been identified as AlaAspThrTyrAlaAlaThrArgTyrProValIleLeuValHisGlyLeuAlaGlyThrAspLys (=ADTYAATRYPVILVHGLAGTDK). This amino acid sequence is encoded by nucleotides 118–183 (FIG. 2). Firstly, from these findings it can be concluded that the mature lipase enzyme is composed of 319 amino acid residues, and has a calculated molecular weight of 33,092 dalton. Secondly, the enzyme is synthesized as a precursor, with a 39 amino acid residue N-terminal extension (numbered –39 to –1 in FIG. 2).

From the scientific literature it is well known that most excreted proteins are produced intracellular as precursor enzymes (16). Most commonly these enzymes have a N-terminal elongation, the so-called leader peptide or signal sequence. This peptide is involved in the initial interaction with the bacterial membrane.

General features of the signal sequence as it is found in gram negative bacteria are:

1. an amino-terminal region containing (on average) 2 positively charged amino acid residues;
2. a hydrophobic sequence of 12 to 15 residues;
3. a cleavage site region, ending with serine, alanine or glycine
4. the total length is approximately 23 amino acids.

Surprisingly, the lipase signal sequence comprises 39 amino acids, which is rather long. Furthermore, it contains four positively charged amino acids at the N-terminus.

For gram negative bacteria, this seems to be an exceptional type of signal sequence. related lipases As mentioned earlier, the *P. glumae* lipase belongs to a group of immunologically related lipases. From this it can be expected that these enzymes, although produced by different organisms, contain stretches of highly conserved amino acids sequences.

As a consequence there has to be certain degree of homology in the DNA-sequence.

Having the *P. glumae* lipase gene at our disposal, it is easy to isolate related lipase genes from other organisms.

This can be done in essentially the same way as described above.

From the organism of interest a gene bank (for example in a cosmid or phage Lambda) is made. This genome bank can be screened using (parts of) the ~2.2 kb BamHI fragment (described above) as a probe. Colonies giving a positive signal, can be isolated and characterized in more detail.

EXAMPLE 2

CONSTRUCTION OF THE LIPASE NEGATIVE *P. glumae* STRAINS PG2 AND PG3

The construction of PG2, from which the lipase gene has been deleted; and PG3, in which the lipase gene has been replaced with a tetracycline resistance (Tc-res) gene, comprises three main steps.

A—construction of pUR6106 and pUR6107 (in *E. coli*), starting from pUR6001 (see example 1)

pUR6001 contains a BamHI fragment from the *P. glumae* chromosome of ~2.2 kb. The lipase gene (1074 base pairs) situated on this fragment, has a 5'- and a 3'-flanking sequence of ~480 and ~660 base pairs, respectively.
Subsequent construction steps were:

a. partial digestion of pUR6001 (isolated from *E. coli* KA816 dam-3, dcm-6, thr, leu, thi, LacY, galK2, galT22, ara-14, tonA31, tsx-78, supE44) (also named GM418 [17]) with ClaI, to obtain linearized plasmids b. phenol extraction and ethanol precipitation (7) of the DNA, followed by digested with PstI c. isolation of a 4.5 kb plasmid DNA fragment (having ClaI and a PstI sticky ends), and a PstI fragment of ~670 bp from agarose gel after gel electrophoresis followed by electro-elution in dialysis bags (7)

d. the obtained plasmid DNA fragment with a ClaI and a PstI sticky end was ligated with a synthetic linker fragment (shown below), with a ClaI and a PstI sticky end.

ClaI CGATGAGATCTTGATCACTGCA PstI
      TACTCTAGAACTAGTC

This synthetic fragment contains a recognition site for the restriction enzymes BclI and BglII. After transformation of the ligation mixture to *E. coli* SA101 (is JM101 with recA, hdsR), selection on LB-Ap (100 μg ampicillin/ml) agar plates, and screening of the plasmids from the obtained transformants by restriction enzyme analysis, a correct plasmid was selected for the next construction step. Upon digesting this correct plasmid with BamHI and HindIII a vector fragment of ~4 kb and an insert fragment of ~500 bp were found.

e. the plasmid construct obtained as described in d. was digested with PstI, and ligated together with the ~670 bp PstI fragment isolated as described in c.

f. transformation of the ligation mixture to *E. coli* SA101, selection on LB-Ap (100 μg ampicillin/ml) agar plates, and screening of the plasmids from the obtained transformants. Since the PstI fragment can have two different orientations this had to be analysed by means of restriction enzyme analysis. In the construct we were looking for, the orientation should be thus that digestion with BamHI results in a vector fragment of ~4 kb and an insert-fragment of ~1.2 kb.

A representative of the correct plasmids is depicted in FIG. 3 and was called pUR6102.

g. pUR6102 was digested to completion with BglII h. pBR322 (18) was digested to completion with AvaI and EcoRI, after which the DNA fragments were separated by agarose gel electrophoresis. A fragment of ~1435 basepairs, containing the tetracycline resistance gene was isolated from the gel by electro-elution i. upon filling in the sticky ends (in a buffer containing 7 mM tris-HCl pH 7.5, 0.1 mM EDTA, 5 mM β-mercaptoethanol, 7 mM MgCl$_2$, 0.05 mM dNTPs and 0.1 φμl Klenow polymerase) of the DNA fragment containing the Tc-res gene and the linearized pUR6102 they were ligated.

j. transformation of *E. coli* SA101 with the ligation mixture, selection on LB-Tc (25 μg tetracycline/ml) agar plates, and screening of the plasmids from the obtained transformants by restriction enzyme analysis.

The construction route of pUR6102 and pUR6103 is depicted in FIG. 3.

k. pUR6102 was digested with BamHI and pUR6103 was partially digested with BamHI; the obtained fragments were separated by agarose gel electrophoresis and the desired fragments (~1145 bp and ~2550 bp resp.) were isolated out of the gel by electro-elution.

l. pRZ102 (19) was digested to completion with BamHI and ligated to the BamHI fragments obtained in step k.

m. transformation of the ligation mixtures to *E. coli* S17-1 (20), selection on LB-km,Tc (25 μ/ml each) and screening of the plasmids from the obtained transformants, by restriction enzyme analysis. The resulting plasmids were called pUR6106 and pUR6107 (FIG. 4), respectively.

B—Deletion of the lipase gene of the *P. glumae* chromosome a. Introduction of pUR6106 in *P. glumae* via biparental conjugation with *E. coli* S17-1(pUR6106) (which is the notation for *E. coli* S17-1 containing plasmid pUR6106).

A *P. glumae* colony was transferred from a MME plate (0.2 g/l MgSO$_4$-7H$_2$O, 2 g/l Citrate-H$_2$O, 10 g/l K$_2$HPO$_4$, 3.5 g/l NaNH$_4$HPO$_4$.4H$_2$O, 0.5% glucose and 1.5% agar) to 20 ml Luria Broth (LB) culture medium and grown overnight at 30° C. *E. coli* S17-1(pUR6106) was grown overnight in 3 ml LB medium, 25 μg/ml Km, at 37° C.

The next day the *P. glumae* culture was diluted 1:1 and grown for 4 to 5 hours at 30° C. until OD660 is 2.0–2.5. *E. coli* S17-1 (pUR6106) was diluted 1:50 and grown for 4 to 5 hours at 37° C. until OD660 is 1.5 –2.0

For the conjugation 50 OD units (1 unit=1 ml with OD=1) (20 to 25 ml) *P. glumae* cells and 2.5 OD units (1.2–1.6 ml) *E. coli* S17-1 (pUR6106) were mixed and spun down for 10 min at 5,000 rpm (HS4-rotor). The cell pellet was divided over 3 LB plates and incubated overnight at 30° C.

Subsequently the cell material was removed from the plate and re-suspended in 3 ml 0.9% NaCl solution and pelleted by centrifugation (10 min, RT, HB4-rotor, 4 krpm).

The cell pellet was re-suspended in 1.8 ml 0.9% NaCl solution and divided over 3 plates MME, 0.5% glucose, 1.5% agar, 50 μg/ml kanamycin (Km) and grown at 30° C.

Since pUR6106 does not replicate in *P. glumae*, Km resistant trans-conjugants can only be obtained by integration. In these strains the plasmid pUR6106 is integrated into the bacterial chromosome by a single recombination event at the 5'- or 3'-flanking region. Due to the fact that these strains still contain a functional lipase gene, their phenotype is lipase positive.

b. Two such strains (PG-RZ21 and PG-RZ25) were selected for further experiments.

To delete the plasmid and the functional lipase gene out of the chromosomal DNA, a second recombination event should take place. This can be achieved by growing said strains for several days on LB-medium without Km (without selective pressure), plate the cells on BYPO-plates (10 g/l trypticase peptone, 3 g/l yeast extract, 5 g/l beef extract, 5 g/l NaCl, 7 g/l $KH_2PO_4$, 50 ml/l olive oil emulsion and 1.5% agar) in a density which assures separate colonies, and screen for lipase negative colonies. Upon plating these lipase negative colonies on selective plates (MME-KM 50 μg/ml), they should not grow. A strain obtained in this way could be called PG-2.

C—Replacement of the lipase gene of the P. glumae chromosome by the Tc-res gene a. Introduction of pUR6107 in P. glumae via conjugation with E. coli S17-1 (pUR6107) as described in B. Selection of trans-conjugants was performed at 30° C. on MME-medium containing 50 μg/ml Tc.

b. Trans-conjugants obtained in this way were duplicated to BYPO-plates containing 50 μg/ml Tc and to MME-plates containing 100 μg/ml Km. Several transconjugants exhibited a Km sensitivity (no growth on MME Km-100 plates) and lipase negative (no clearing zone on BYPO-plates) phenotype. Due to a double cross over (at the 5'- and at the 3'-flanking region) the lipase gene was replaced by the Tc resistance gene.

One representative strain was selected for further investigation and was called PG-3.

EXAMPLE 3

CONSTRUCTION OF A SYNTHETIC GENE ENCODING P. glumae (PRE)-LIPASE

Based on the nucleotide sequence of the P. glumae (pre)-lipase gene a new gene was designed, containing several silent mutations. Due to these mutations the amino acid sequence of the enzyme was not changed. It was however possible to lower the GC-content, which facilitates enzyme engineering and enabled us to use the synthetic gene in a variety of heterologous host systems. An other point, facilitating enzyme engineering, was the possibility to introduce restriction enzyme recognition sites at convenient positions in the gene.

The sequence of the new gene is given in FIG. 5(A).

The new gene was divided in restriction fragments of approximately 200 nucleotides, so-called cassettes. An example of such a cassette is depicted in FIG. 6.

Each cassette was elongated at the 5' and 3' end to create an EcoRI and HindIII site respectively.

The coding strands of these cassettes were divided in oligo-nucleotides (oligos) with an average length of 33 bases. The same was done for the non coding strands, in such a way that the oligos overlapped for ~50% with these of the coding strand.

The oligos were synthesized as described in example 1.

Before assembling the fragments, the 5' ends of the synthetic oligos had to be phosphorylated in order to facilitate ligation. Phosphorylation was performed as follows:

Equimolar amounts (50 pmol) of the oligos were pooled and kinated in 40 μl reaction buffer with 8 Units polynucleotide kinase for 30–45 minutes at 37° C. The reaction was stopped by heating for 5 minutes at 70° C. and ethanol precipitation.

Annealing was done by dissolving the pellet in 30 μl of a buffer containing: 7 mmol/l Tris-HCl pH 7.5, 10 mmol/l 2-mercapto-ethanol, 5 mmol/l ATP were added.

Subsequently the mixture was placed in a water bath at 65° C. for 5 minutes, followed by cooling to 30° C. over a period of 1 hour. $MgCl_2$ was added to a final concentration of 10 mmol/l. T4 DNA-Ligase (2.5 Units) was added and the mixture was placed at 37° C. for 30 minutes or o/n at 16° C. After this the reaction mixture was heated for 10 minutes at 70° C.

After ethanol precipitation the pellet was dissolved in digestion buffer and cut with EcoRI and HindIII.

The mixture was separated on a 2% agarose gel and the fragment with a length corresponding to the correctly assembled cassette was isolated by electro-elution.

The fragments were ligated in pEMBL9 (digested with EcoRI/HindIII) as described in example 1, and they were checked for correctness by sequence analysis. In subsequent cloning steps the various cassettes were put together in the proper order, which resulted in pUR6038. This is a pEMBL9 derivative containing the complete synthetic lipase gene.

To be able to make the constructions as described in example 4, a second version of the synthetic gene was made, by replacing fragment 5. In this way construct pUR6600 was made, having the 3' PstI site at position 1069 instead of position 1091 (See FIG. 5B).

EXAMPLE 4

INTRODUCTION OF THE (WILD TYPE) SYNTHETIC LIPASE GENE IN THE LIPASE NEGATIVE P. GLUMAE PG3

In order to test whether the synthetic lipase gene is functional in P. glumae, the gene was introduced in strain PG3.

To simplify fermentation procedures, it was decided to stably integrate this gene in the PG3 chromosome, rather than introducing on a plasmid.

For this reason the synthetic lipase gene had to be equipped with the 5' and 3' border sequences of the original P. glumae lipase gene.

This was achieved in the following way (see FIG. 7):

a. From pUR6002 (ex E. coli KA816) a vector with ClaI and PstI sticky ends was prepared in the same way as described in example 2.
b. pUR6600 (ex *E. coli* KA816) was digested to completion with ClaI and partial with PstI. After separating the fragments by agarose gel electrophoresis a fragment of ~1050 bp was isolated.
c. The fragment thus obtained, was ligated in the pUR6002 derived vector and used to transform *E. coli* SA101. In this way construct pUR6603 was obtained.
d. pUR6603 was digested to completion with BamHI. After separating the fragments by agarose gel electrophoresis a fragment of ~2.2 kb was isolated. This fragment contains the synthetic lipase gene with the 5' and 3' flanking regions, of the wild type *P. gladioli* lipase gene.
e. pRZ102 was also digested to completion with BamHI.
f. The 2.2 kb fragment obtained in d. was ligated in pRZ102 as described in example 2.
g. The resulting construct, pUR6131 was transferred to *E. coli* S17-1.

Integration of this construct in the chromosome of PG3 was accomplished in the same way as described for pUR6106 in example 2 section B-a.

From the obtained Km-resistant trans-conjugants, several were transferred to BYPO plates. They all appeared to have the lipase positive phenotype, since clearing zones occurred around the colonies. A typical representative was called PGL26.

Obviously the same route can be followed to integrate construct (pUR6131) in a lipase negative P. glumae PG2 (see example 2B-b) strain.

From the examples 2 and 4 it might be clear that the P. glumae strain PG1 (and derivatives thereof, e.g. PG2 and PG3; or derivatives of PG1 obtained via classical mutagenesis having an improved lipase production) can be manipulated easily by deleting or introducing (homologous or heterologous) DNA fragments in the bacterial chromosome.

By using these techniques it is possible to construct a strain optimized for the production of lipase. In this respect one could think of:

replacing the original lipase promotor, by a stronger (inducible) promotor, introduction of more than one copy of the lipase gene (eventually, encoding different lipase mutants), replacing the original promoter, or introduction of more copies of genes encoding functions involved in the production and excretion of the lipase enzyme (eg. chaperon proteins, "helper proteins" involved in the export of the lipase enzyme), deletion of the gene encoding extracellular protease (A Tn5 mutant of PG1 (PGT89) which does not produce a clearing zone or skimmilk plates has been deposited), manipulating the rhamnolipid production.

EXAMPLE 5

PRODUCTION OF MUTANT LIPASE GENES AND THEIR INTRODUCTION IN PG3

To improve the lipase, it is necessary to have the possibility to introduce well-defined changes in the amino acid sequence of the protein.

A preferred method to achieve this is via the replacement of a gene fragment of the synthetic gene encoding wild type lipase or of the wild type P. glumae lipase gene, with a corresponding chemically synthesized fragment containing the desired mutation. In the case of the synthetic wild type lipase gene, a cassette (or fragment thereof) can be replaced with a corresponding cassette (or fragment thereof) containing the desired mutation.

The cassette, comprising the codon(s) for the amino acid(s) of interest, was assembled once more (as described in Example 3). This time however, the oligos of the coding and the non-coding DNA strands, comprising the codon(s) of interest, were replaced by oligomers with the desired mutation. The new oligos were synthesised as described in Example 1.

The thus obtained mutant cassette, or a fragment thereof was introduced at the corresponding position in the synthetic wild type lipase gene of constructs like pUR6038 or pUR6603.

To introduce a synthetic mutant lipase gene in PG2 or PG3, the route as described in Example 4 has to be followed, starting at step d.

A typical example of the production of a mutant gene is described below. In this case the His at position 154 of the wild type lipase gene has been replaced by a Pro. To accomplish this, two new oligomers were synthesized. The codon encoding amino acid 154 of the mature lipase is changed to CCT.

These oligomers were used to assemble fragment 3(H154P), as described in example 3. After cloning the fragment in pEMBL9, the DNA sequences was determined as described in example 1. The thus obtained construct was called UR6071.

Plasmid pUR6071 was digested to completion with FspI and SalI. Upon separation of the obtained DNA fragments via gel electrophoresis (as described in example 2), a fragment of ~90 bp was isolated out of agarose gel. pUR6002 was partially digested with FspI and partially with SalI. After gel electrophoresis a vector of ~6000 nucleotides was isolated out of the agarose gel in example 2.

The isolated ~90 bp fragment was ligated in the pUR6002 vector to obtain pUR6077A.

The BamHI fragment (~2200 bp) of pUR6077A was ligated in pRZ102 as described in examples 3 and 4. In this way pUR6127 was obtained.

Introduction of this construct into the chromosome of PG3 was accomplished as described in example 4. A resulting lipase producing P. glumae trans-conjugant, was called PGL24.

The modified lipase produced by this strain proved to be significantly more stable than the parent lipase in an actual detergents system (FIG. 8).

In essentially the same way several other mutant lipase genes have been made. In some cases this resulted in a altered net charge of the encoded protein (eq. D157R (+2), D55A (+1), I110K (+1), R61P (−1), T109D (−1) R8D (−2)). In other cases amino acids have been introduced or deleted (eg. PGL40 in which 152S-154H has been replaced by AlaLeuSerGlyHisPro=ALSGHP).

Furthermore potential glycosylation sites have been removed (eq. N48S and/or N238S) and/or introduced (eg. D157T and insertion of G between N155 and T156).

EXAMPLE 6

EXPRESSION OF THE SYNTHETIC LIPASE GENES IN Saccharomyces cerevisiae USING AUTONOMOUSLY REPLICATING PLASMIDS To illustrate the production of P. glumae lipase by eukaryotic micro-organisms, vectors suited for expression of P. glumae lipase in the yeast S. cerevisiae using the GAL7 promoter (21) were constructed. The P. glumae lipase is produced by the yeast S. cerevisiae using two different expression systems. An expression system based on autonomously replicating plasmids with the lipase expression cassette and an expression system based on multicopy integration of the lipase expression cassette in the host genome.

The plasmid pUR2730 (21) was used as the basis for the lipase expression plasmids. The plasmid pUR2730 consists of the GAL7 promoter, S. cerevisiae invertase signal sequence, α-galactosidase gene (the α-galactosidase expression cassette), 2 μm sequences for replication in S. cerevisie, the LEU2d gene for selection in S. cerevisiae and pBR322 sequences for replication and selection in E. coli.

The plasmid pUR6038 was used as the source for the lipase gene.

The following S. cerevisiae expression plasmids were constructed, encoding:

1. mature lipase preceded by the invertase signal sequence (pUR6801), 2. mature lipase preceded by a KEX2 cleavage site, a glycosylation site and the invertase signal sequence (pUR6802).

In order to obtain the above mentioned constructs, the routes followed were (FIG. 9; the used restriction recognition sites are marked with an asterisk):

ad 1 and 2.

a. The plasmid pUR2730 was digested with SacI and HindIII and the vector fragment was isolated.
b. The plasmid pUR6038 was digested with EcoRV and HindIII and the fragment with the lipase gene was isolated.
c. Synthetic SacI-EcoRV DNA fragments were synthesized and constructed as described in example 3, consisting of the following sequences:

In the case of pUR6801:

```
5'    CATCACACAAACAAACAAAACAAAATGATGCTTTTGCAAGCCTTCCTTTTCCTT-  I.
3' TCGAGTAGTGTGTTTGTTTGTTTTGTTTTACTACGAAAACGTTCGGAAGGAAAAGGAA-

-TTGGCTGGTTTTGCAGCCAAAATATCTGCCGCGGACACATATGCAGCTACGAGAT    3'
  -AACCGACCAAAACGTCGGTTTTATAGACGGCGCCTGTGTATACGTCGATGCTCTA    5'
```

This fragment gives a correct junction of the GAL7 promoter and the lipase gene with in between the sequence encoding the invertase signal sequence.

In the case of pUR6802:

```
5'     CATCACACAAACAAACAAAACAAAATGATGCTTTTGCAAGCCTTCCTTTTCCT-  II.
3'  TCGAGTAGTGTGTTTGTTTGTTTTGTTTTACTACGAAAACGTTCGGAAGGAAAAGGA-

-TTTGGCTGGTTTTGCAGCCAAAATATCTGCCTCCGGTACTAACGAAACTTCTGATAA-
   -AAACCGACCAAAACGTCGGTTTTATAGACGGAGGCCATGATTGCTTTGAAGACTATT-

-GAGATGAAGCGAAGCTGCTGACACATATGCAGCTACGAGAT          3'
   -CTCTCTTCGACTTCGACGACTGTGTATACGTCGATGCTCTA          5'
```

This fragment gives a correct junction of the GAL7 promoter and the lipase gene with in between the sequences encoding a KEX2 cleavage site, a glycosylation site and the invertase signal sequence.

d. The SacI-HindIII vector fragment, one of the SacI-EcoRV synthetic fragments (I) and the EcoRV-HindIII DNA fragment with the lipase gene were ligated. For the construction of pUR6801 this is shown in FIG. 9. (pUR6802 is constructed in the same way, using synthetic fragment II)
e. The ligation mixture was transformed to E. coli. From single colonies, after cultivation, the plasmid DNA was isolated and the correct plasmids, as judged by restriction enzyme analysis, were selected and isolated in large amounts.
f. The plasmids pUR6801 and pUR6802 were transformed to S. cerevisiae strain SU10 (21) using the spheroplast procedure (22) using selection on the presence of the LEU2d gene product.
g. The transformants were grown overnight in defined medium (0.68% Yeast Nitrogen Base w/o amino acids, 2% glucose, histidine and uracil), diluted 1:10 in induction medium (1% yeast extract, 2% bactopeptone, 5% galactose) and grown for 40 hours.
h. The cells were isolated by centrifugation and cell extracts were prepared (23).
i. The cell extracts were analysed by SDS-gel-electrophoresis (7) and blotted on nitrocellulose.
j. The nitrocellulose blots were incubated with lipase antibodies and subsequently with I125 labelled protein A followed by fluorography (FIG. 10).

As shown in FIG. 10, SU10 cells containing the plasmid pUR6801 produce lipase enzyme with the correct molecular weight as compared to lipase from P. glumae. In addition to the correct protein also not processed and glycosylated lipase protein can also be seen. The P. glumae lipase produced by S. cerevisiae is enzymatically active.

EXAMPLE 7

PRODUCTION OF P. glumae LIPASE BY S. cerevisiae USING MULTICOPY INTEGRATION

The multi-copy integration vector was derived from the plasmid pARES6 (24) by replacing the 335 bp yeast RNA polymerase I promoter element with the 4.5 BglII B fragment of S. cerevisiae rDNA (25). Also the 2 μm origin of replication was removed and the BglII-HindIII DNA fragment comprising chloroplast DNA from S. oligorhiza was replaced by a polylinker DNA sequence. This resulted in plasmid pUR2790 from which a detailed picture is shown in FIG. 11.

The essential sequences for multicopy integration in the yeast genome of pUR2790 are: 1. rDNA sequences for multicopy integration in the yeast genome, 2. the S. cerevisiae LEU2d gene (26); this is the LEU2 gene with a deficient promoter.

Amongst others, the following multicopy integration expression plasmids were constructed, encoding:
1. mature lipase preceded by the invertase signal sequence (pUR6803),
2. mature lipase preceded by a KEX2 cleavage site, a glycosylation site and the invertase signal sequence (pUR6804).

In order to obtain the above mentioned constructs, the routes followed were (FIG. 12; the used restriction recognition sites are marked with an asterisk):

ad 1 and 2.

a. The plasmid pUR2790 was partially digested with HindIII. The linear plasmid was isolated d digested to completion with BglII and the HindIII-BglII vector fragment was isolated by agarose gel-electrophoresis and electro-elution.
b. The plasmid pUR6801 was digested partially with BglII and to completion with HindIII and the BglII-HindIII DNA fragment with the lipase gene was isolated (pUR6804 is constructed in the same way using plasmid pUR6802 instead of pUR6801).
c. The BglII-HindIII vector fragment of pUR2790 and the BglII-HindIII fragment with the lipase gene were ligated (FIG. 12), resulting in plasmid pUR6803.
d. The ligation mixture was transformed to E. coli. From single colonies, after cultivation, the plasmid DNA was isolated and the correct plasmids, pUR6803 and pUR6804, as judged by restriction enzyme analysis were selected and isolated in large ounts.

e. The plasmids pUR6803 and pUR6804 were transformed to S. cerevisiae strain YT6-2-1 L (26)=SU50 with the spheroplast procedure (22) using selecting for the presence of the LEU2d gene product. The host strain SU50 is deficient for the essential nutrient leucine (LEU2), which means that strain SU50 is not capable of producing leucine. Thus it can only grow when the growth medium contains sufficient amounts of leucine.

The deficient promoter of the LEU2 gene present in vectors pUR6803 and pUR6804 is essential for multicopy integration of the plasmid vectors in the yeast genome. The multicopy integration occurs at the rDNA locus of the yeast genome due to homologous recombination of the rDNA sequences of the plasmids and the rDNA sequences of the yeast genome.

f. The integrants were grown overnight in defined medium (0.68% Yeast Nitrogen Base w/o amino acids, 2% glucose, histidine and uracil), diluted 1:10 in induction medium (1% yeast extract, 2% bactopeptone, 5% galactose) and grown for 40 hours.

g. The cells were isolated by centrifugation and cell extracts were prepared (23).

h. The cell extracts were analysed by SDS-gel-electrophoresis (7) and blotted to nitrocellulose filters.

i. The nitrocellulose blots were incubated with lipase antibodies and subsequently with I125 labelled protein A followed by fluorography (FIG. 13).

As shown in FIG. 13, integrants of SU50 with the plasmid pUR6803 produce lipase enzyme with the correct molecular weight as compared to lipase from P. glumae. In addition to the correct protein, not processed and glycosylated lipase protein can also be seen. The P. glumae lipase produced by S. cerevisiae is enzymatically active.

In this way yeast strains have been obtained carrying multiple integrated copies (up to 100 copies per haploid genome) of either the plasmid pUR6803 or pUR6804 (including the lipase expression cassette) for the production of active P. glumae lipase. This multicopy integration system is stable even under non-selective conditions.

EXAMPLE 8

PRODUCTION OF GUAR α-GALACTOSIDASE IN Saccharomyces cerevisiae USING MULTICOPY INTEGRATION In this example the expression of a heterologous protein, α-galactosidase from guar (Cyamopsis tetragonoloba) in Saccharomyces cerevisiae, using multicopy integration, is described. The gene encoding guar α-galactosidase was fused to homologous expression signals as is described by Overbeeke (21) resulting in the expression vector pUR2730. The α-galactosidase expression cassette of pUR2730 consists of the S. cerevisiae GAL7 promoter, the S. cerevisiae invertase signal sequence and the α-galactosidase gene encoding mature α-galactosidase. The multicopy integration vector used is pUR2770, which is identical to pMIRY2.1 (27). The α-galactosidase expression cassette was isolated and inserted in the multicopy integration vector pUR2770 resulting in pUR2774. This multicopy integration vector contains the α-galactosidase expression vector, S. cerevisiae ribosomal DNA sequences and the S. cerevisiae deficient LEU2 gene (LEU2d) as a selection marker. The multicopy integration vector was transformed to S. cerevisiae and multicopy integrants were obtained. The multicopy integrants were mitotically stable and the multicopy integrants expressed and secreted the plant protein α-galactosidase. This example clearly demonstrates that it is possible to obtain multicopy integration in the genome of S. cerevisiae and that the multicopy integrants can be used for the production of proteins. All DNA manipulations were carried out as described in Maniatis (7).

1. Construction of multicopy integration vector PUR2774

The multicopy integration vector pUR2770 was partially digested with HindIII and the linearized vector fragment was isolated. The linear vector fragment was digested to completion with BamHI and the resulting 8 kb vector fragment was isolated. The α-galactosidase expression cassette was isolated from pUR2730 by digestion with HindIII and BglII and isolation of the 1.9 kb DNA fragment. The α-galactosidase expression cassette was ligated in the isolated vector fragment of pUR2770 resulting in the multicopy integration vector pUR2774 (see also FIG. 14). The ligation mixture was transformed to E. coli. From single colonies, after cultivation, the plasmid DNA was isolated and the correct plasmids, as judged by restriction enzyme analysis, were selected and isolated in large amounts. The multicopy integration vector pUR2774, linearized with SmaI was transformed to the S. cerevisiae strain YT6-2-1 L (26) using the spheroplast method (22) by selecting for the presence of the LEU2d gene product.

2. Analysis of the integration pattern of the multicopy integrants

The ribosomal DNA of S. cerevisiae is present in ±150 identical copies of the rDNA unit, comprising the genes that specify the 17S, 5.8S and 26S rRNA components of the ribosomes of S. cerevisiae These rDNA units are tandemly repeated in a large gene cluster on chromosome XII of S. cerevisiae. The complete sequence of the rDNA unit is known, the rDNA unit is 9.0 kB large and contains two BglII sites (28, 29, 30). When chromosomal DNA isolated from S. cerevisiae is digested with BglII, the rDNA gene cluster gives rise to two fragments, with a length of 4.5 kb. This gene organization is schematically represented in FIG. 15A. The 4.5 kb band corresponding to the ribosomal DNA fragments is detectable in the restriction pattern on an ethidium-bromide stained agarose gel, because of the large number of ribosomal DNA units present in a haploid genome. The plasmid pUR2774 has a length of 9.8 kb and contains one single BglII restriction enzyme recognition site. If plasmid pUR2774 is tandemly integrated in a high copy-number, digestion of the chromosomal DNA with BglII will give rise to a 9.8 kb DNA fragment. With an ethidium-bromide stained agarose gel a comparison can be made between the intensity of the 4.5 kb DNA band, corresponding to ±150 copies of the ribosomal DNA unit, and the 9.8 kb DNA band, derived from the integrated plasmid. This gene cluster organization is shown in FIG. 15B. This comparison will give a reasonable estimation of the number of integrated pUR2774 plasmids. pUR2774 was linearized and transformed to the yeast strain YT6-2-1 L (SU50) which is LEU2$^-$. Transformants were streaked on MM(defined)-medium without leucine for an extra check for the LEU2$^+$ phenotype. To examine whether integration of the multi-copy vector pUR2774 actually occurred, chromosomal DNA was isolated from independent integrants SU50A, SU50B, SU50C and SU50D. The total DNA was digested with BglII and analyzed by gel-electrophoresis. An example of such a ethidium-bromide stained gel is shown in FIG. 16. As expected, in the restriction patterns of integrants SU50B and SU50C, two main bands can be distinguished at 4.5 and 9.8 kb. The parent strain gives to a single band only of 4.5 kb; the rDNA unit. So, we can conclude that in addition to the multiple ribosomal DNA units, these integrants surprisingly also contain multiple integrated copies of the 9.8 kb plasmid pUR2774. Different multicopy integrants were found to contain different copy-numbers of the plasmid pUR2774 varying from 10 to 100. To confirm the presence of the α-galactosidase gene, hybridization with radio-labelled probe was performed. The probe for the α-galactosidase gene was isolated from pUR2731, a pUR2730 derivative, by digestion with PvuII and HindIII and isolation of the 1.4 kb fragment containing the α-galactosidase gene. To identify the rDNA sequences a probe was prepared by digestion of pUR2770 with SmaI and HindIII, followed by isolation and labelling of the 2.0 kb fragment. Upon hybridisation with the α-galactosidase probe (see FIG. 17) it was found that the 9.8 kb band as detected in the ethidium bromide stained gel indeed corresponds to the α-galactosidase gene since this single band was present in the autoradiographs, while in the lane containing digested total DNA from the YT6-2-1 L parent strain no hybridisation signals were detected. Since we could detect the 9.8 kb band no extensive re-arrangements and/or deletions can have occurred in the integration process. Hybridisation with the rDNA probe resulted in signals corresponding to a 4.5 kb band and a 9.8 kb band, from which it follows that indeed the 4.5 kb band contains the expected ribosomal DNA sequences. As proven with the α-galactosidase probe the 9.8 kb band results from the multicopy integration of pUR2774. This 9.8 kb DNA band also gives a positive signal with the rDNA probe, because pUR2774 also contains ribosomal DNA sequences. From the results shown in FIG. 18, assuming that the 4.5 kb ribosomal DNA band represents 150 copies of the rDNA, the 9.8 kB band containing pUR2774 can be estimated to contain 50–100 copies. Thus, by transformation of the multi-copy integration plasmid pUR2774, it is indeed possible to direct 50–100 copies per cell of the α-galactosidase expression cassette to the genome of S. cerevisiae.

3. Production of α-galactosidase by multicopy integrants

Multicopy integrants SU50A, SU50B, SU50C and SU50D chosen for having high copy numbers of the integrated plasmid were examined for α-galactosidase activity by growing them on 0.67% Yeast Nitrogen Base w/o amino acids, 2% glucose overnight, followed by induction of the GAL7 promoter by a 1:10 dilution in 1% Yeast Extract, 2% Bacto-peptone, 2% galactose (YPGal). The α-galactosidase activity in the supernatants of the cultures was determined by means of an enzyme activity test, as described by Overbeeke et al. (21), at 24 and 48 hours after start of the induction. The results are shown in the following table:

| Integrant | 24 hours induction | | 48 hours induction | |
| --- | --- | --- | --- | --- |
| | OD660 | α-gal mg/l | OD660 | α-gal mg/l |
| SU50A 2%gal | 9 | 58 | 8 | 82 |
| SU50B 2%gal | 15 | 101 | 13 | 235 |
| SU50C 2%gal | 6 | 45 | 4 | 101 |
| SU50D 2%gal | 14 | 41 | 10 | 54 |

The results shown in the table clearly demonstrate that it is possible to obtain high levels of expression of a foreign gene using a multicopy integrant. Moreover, SU50B (235 mg/l) gives rise to a higher level of α-galactosidase production as compared to a expression system with extrachromosomal plasmids (see pUR2730 in reference 21). In spite of the fact that all four multicopy integrants had been elected for having a high copy-number of integrated α-galactosidase expression cassettes, their expression levels vary from 54 to 235 mg/l.

4. Genetic stability of the SU50B multicopy integrant.

To test whether integration of multiple copies α-galactosidase expression plasmids in the S. cerevisiae genome is genetically stable the complete test procedure was repeated under non-selective conditions. Integrant SU50B was streaked on an YPD-agar plate and a pre-culture was inoculated and grown overnight in YPD at 30° C. Subsequently, the pre-culture was diluted 1:10, in YPGal. Samples were taken, optical density measured at 660 nm and the α-galactosidase content of the culture-broth was determined by the enzyme activity assay. Surprisingly, the expression level of α-galactosidase was stable during the whole experiment. This experiment shows that indeed the multiple integrated expression plasmids are maintained very stable under non-selective conditions for many generations. Another important finding was that the multi-copy integrants were stable for months on non-selective YPD-agar-plates kept at 4° C. When the pre-culture of the SU50B integrant is diluted 1:1000 in YP with 2% galactose, grown at 30° C. to an identical OD 660 nm, the α-galactosidase expression is 250 mg/l. In this experiment the pre-culture of the multicopy integrant SU50B is diluted to a larger extend in YPGal, and the cells in the induced culture have to make more divisions before the same biomass and related to this the α-galactosidase production is achieved as with a 1:10 dilution. Thus, we can conclude that the stability of the α-galactosidase production and therefor the genetic stability of the multicopy integrants is very good compared to the stability of extrachromosomal plasmids under non-selective conditions.

We have also found that for multicopy integration and genetic stability of the multicopy integrants the length of the multicopy integration vector is an important parameter. The use of multicopy integration vectors with a length of about 12 kb have a tendency to result in a lower copy number of integrated vectors in the genome and also a decreased genetic stability although still very reasonable. The use of relatively small multicopy integration vectors (±3 kb) results in a high copy number of integrated vectors but with a decreased genetic stability. These results show that the optimal length for a multicopy integration vector, resulting in high copy number of integrated vectors and good genetic stability, is approximately the length of a single ribosomal DNA unit; for S. cerevisiae about 9 kb.

This example clearly demonstrates the feasibility of the use of multicopy integration in S. cerevisiae for the production of proteins. The high genetic stability of the multicopy integrant confer an important advantage as compared to the extrachromosomal plasmid-system where cells have to be grown under selective pressure. The multicopy integrants appeared to be very stable on YPD-agar plates as well as during growth in YPD- and YPGal culture medium for many generations. Considering the high level of expression of the α-galactosidase enzyme and the good mitotic stability of the integrated α-galactosidase expression cassettes, this integrant-system is a realistic option for large-scale production of the α-galactosidase enzyme or any other protein.

EXAMPLE 9

MULTICOPY INTEGRATION IN SACCHAROMYCES CEREVISIAE USING OTHER DEFICIENT SELECTION MARKERS

We have found that for multicopy integration in yeast there are two prerequisites for the multicopy integration vector; the multicopy integration vector should contain ribosomal DNA sequences and a selection marker with a specific degree of deficiency. In the previous examples multicopy integration is obtained using a multicopy integration vector with ribosomal DNA sequences and the defective LEU2 gene (LEU2d) as a selection marker. In this example the use of other (than LEU2d) defective selection markers in order to obtain multicopy integration in yeast is described. In this example multicopy integration vectors are used with either a deficient TRP1 or a deficient URA3 instead of the LEU2d gene. The expression of both these genes was severely curtailed by removal of a significant part of their 5' flanking regions. Using these multicopy integration vectors, multicopy integrants were obtained in which approximately 200 copies of the vector integrated. This example clearly demonstrates that multicopy integration can also be effected by other deficient selection markers. All standard DNA manipulations were carried out as described in Maniatis (7).

1. Construction and analysis of pMIRY plasmids containing a deficient TRP1 gene as selection marker.

In order to test the possibility that multicopy integration into the genome can be obtained using different types of selection pressure during transformation, series of pMIRY2.1-analogous plasmids (pMIRY2.1 is identical to pUR2770) were constructed, containing deficient alleles of two genes commonly used as selection markers: the TRP1 and URA3 genes of S. cerevisiae. The TRP1 gene encodes the enzyme N-(5'-phosphoribosyl-1)-anthranilate (PRA) isomerase, which catalyzes the third step in the biosynthesis of tryptophan (31). Transcription of the TRP1 gene is initiated at multiple sites which are organized into two clusters (FIG. 19), one at about position −200 relative to the ATG start codon and the other just upstream of this codon (32). Each of the two clusters is preceded by putative TATA elements as well as (dA:dT)-rich regions that could act as promoter elements (3). When the upstream region of the TRP1 gene is deleted up to the EcoRI site at position −102 (TΔ1), the first cluster of transcription start sites is removed and the expression level of the gene drops to only 20% to 25% of the value of its wild-type counterpart (31). This particular deficient TRP1 allele is currently used as selection marker in several yeast vectors. We hypothesize that this degree of deficiency was not high enough and therefore the deletion in the 5'-flanking sequence was extended to either position −30 (TΔ2) or −6 (TΔ3) upstream of the ATG codon. The TΔ2 gene still contains part of the downstream cluster of transcription initiation sites. In the TΔ3 deletion mutant both clusters as well as all poly dA:dT stretches and putative TATA elements are deleted. These two mutant TRP1 genes as well as the original TΔ1 gene were used in construction of the pMIRY6-T series of plasmids. Construction of this series was carried out as follows (FIG. 20): first, the 766 bp AccI-PstI (FIG. 19) fragment, containing the TRP1 coding region plus 30 bp of 5'-flanking sequence, was cloned between the SmaI and PstI sites of pUC19, resulting in plasmid pUC19-TΔ2 (the AccI site was made blunt by filling in the 3'-end using T4 polymerase). Subsequently, the 3.5 kb SphI fragment from a pUC18 subclone containing the BglII-B rDNA fragment (27) was inserted into the SphI site of the pUC19-TΔ2 polylinker giving plasmid pMIRY6-TΔ2. Plasmids pMIRY6-TΔ1 and pMIRY6-TΔ3 are derivatives of pMIRY6-TΔ2. To obtain pMIRY6-TΔ1, the 867 bp EcoRI-BglII TRP1 fragment was first cloned between the EcoRI and the BamHI sites of pUC19, giving plasmid pUC19-TΔ1. In the next step the 1.2 kb ScaI-EcoRV fragment of pMIRY6-TΔ2 which contains a portion of the pUC19 sequence as well as part of the TRP1 gene (FIG. 20), was replaced by the 1.3 kb ScaI-EcoRV fragment from pUC19-TΔ1 restoring the length of the 5' flanking sequence of the TRP1 gene to 102 bp. pMIRY6-TΔ3 was constructed in a similar way. First, the 405 bp AluI fragment from the TRP1 gene was cloned into the SmaI site of pUC19, giving pUC19-TΔ3. Subsequently, the 1.2 kb ScaI-EcoRV fragment of pMIRY6-TΔ2 was replaced by the 1.2 kb ScaI-EcoRV fragment from pUC19-TΔ3, to give pMIRY6-TΔ3.

Plasmids, pMIRY6-TΔ1, pMIRY6-TΔ2 and pMIRY6-TΔ3 were transformed into yeast after linearization with HpaI within the rDNA sequence, in order to target integration to the rDNA locus. In FIG. 21 a gel electrophoretic analysis of total DNA is shown from two independently isolated transformants of each type after digestion with EcoRV in the case of pMIRY6-TΔ1 and SacI in the cases of pMIRY6-TΔ2 and pMIRY6-TΔ3. In the case of the pMIRY6-TΔ2 (lanes 3 and 4) and pMIRY6-TΔ3 (lanes 5 and 6) transformants, the rDNA band and the plasmid bands are of comparable intensity. Thus, the copy number of each of the two plasmids is as high as the number of rDNA units per haploid genome, which is approximately 150 (33). The copy number of the pMIRY6-TΔ2 and -TΔ3 plasmids is of the same order. In contrast, transformation with pMIRY6-TΔ1 did not result in high-copy-number transformants. As shown in FIG. 21 (lanes 1 and 2), no 6.9 kb band corresponding to the linearized pMIRY6-TΔ1 plasmid is visible upon SacI digestion of the total DNA from pMIRY-TΔ1 transformed cells. The results described above clearly demonstrate that multicopy integration into the yeast rDNA locus does not absolutely require the presence of the LEU2d gene selection marker in the vector. Instead, deficient TRP1 alleles can be used, provided their expression falls below a critical level.

2. Construction and analysis of a pMIRY plasmid with a deficient URA3 gene as selection marker.

Next to the LEU2 and the TRP1 genes, the URA3 gene is one of the most widely used selection markers in yeast vectors (34). The URA3 gene encodes orotidine-5'-phosphate carboxylase (OMP decarboxylase). The expression of this gene is controlled at the level of transcription by the PPR1 gene product which acts as a positive regulator (35). Deletion analysis suggests that the sequence essential for PPR1 induction of URA3 is located in a 97 bp long region located just upstream of the ATG translation start codon (36). In order to obtain a promoter of the URA3 gene with the desired degree of deficiency we have deleted most of this region, using a PstI site located 16 bp upstream of the ATG start codon. To that end a BglII linker was inserted in the SmaI site of pFL1 (36B) located in the 3' flanking region of the URA3 gene at position +880 relative to the ATG translational start signal, yielding pFL1-BglII. The 0.9 kb PstI-BglII fragment, comprising the URA3 coding region together with its flanking 3' region abutted by the BglII site and only 16 bp of its 5' flanking region abutted by the PstI site, was cloned between the PstI and BamHI sites of pUC19, yielding pUC19-U (FIG. 22). The 2.8 kb SacI-StuI rDNA fragment containing part of the BglII-B rDNA fragment, was isolated from pUC-BR and inserted between the SmaI and SacI sites in pUC19-UΔ, giving plasmid pMIRY7-UΔ. Copy number analysis of two independently isolated pMIRY7-UΔ transformants is shown in FIG. 23. The plasmid band and the rDNA band have similar intensities which means that the plasmid is integrated in about 200 copies per cell, a result similar to that obtained with plasmids pMIRY6-TΔ2 and pMIRY6-TΔ3. This example clearly demonstrates that multicopy integration into the yeast ribosomal DNA locus is also effected using genes other than LEU2d as selection marker. Indeed, it seems likely that any gene involved in the biosynthesis of a essential nutrient can support this process, when employed as selection marker in a pMIRY plasmid, provided that it is expressed but its expression is below a critical level.

This means that surprisingly we have found that besides the ribosomal DNA sequence a deficient, but essential gene must be present on the multicopy integration vector in order to obtain multicopy integration, in a *S. cerevisiae* strain deficient for that essential gene, of this multicopy integration vector and that the obtained multicopy integrants can be stable for many generations. So the principle of multicopy integration can be extended to all *S. cerevisiae* auxotrophic strains thus permitting a choice from a range of host strains for the expression of any particular gene. Such a choice is an important factor in the optimization of heterologous gene expression in yeast. In particular Trp auxotrophy is an attractive marker for use in an industrial process since even poorly defined media can easily be depleted of tryptophan by heat-sterilization.

EXAMPLE 10

STABILITY OF THE MULTICOPY INTEGRANT SU50 IN CONTINUOUS CULTURES

The multicopy integrant is cultivated in a continuous culture (chemostat) with a working volume of 800 ml at a dilution rate of $0.1\ h^{-1}$ (a mean residence time of 10 hours). The integrant SU50B is a transformant of strain *Saccharomyces cerevisiae* CBS 235.90 with the multicopy integration vector pUR2774 (see example 8). The pH was controlled at 5.0 using 10% $NH_4OH$. Foaming was suppressed using a silicon oil based antifoam (Rhodorsil 426 R Rhone-Poulenc) The feed composition used was A. A steady state was maintained for 120 hours with a stable expression of 360 mg/l α-galactosidase at a biomass dry weight concentration of 11.06 g/l. Similar conditions were stable in other experiments for more than 500 hours. The residual glucose concentration was below the detection limit of 0.05 g/l. The residual galactose concentration was 4.2±0.1 g/l. The inlet contained 170 mg/l leucine derived from the yeast extract and DHW. This resulted in a steady state leucine concentration of 2.0±0.4 mg/l as determined with a amino acid analyzer. After a period of time, 50 mg/l leucine was added to the feed A. Surprisingly the residual leucine concentration in the culture dropped to 0.7±0.2 mg/l. This was accompanied by a considerable decrease of α-galactosidase activity within 80 hours to 144 mg/l (FIG. 24). In FIG. 25 the determination of the copy number during various stages of the experiments is shown. Samples were taken, chromosomal DNA isolated, digested with BglII and subsequently southern blotting was performed using the ribosomal DNA probe as described in example 8. SU50B 1 is a positive control grown in a shake flask. Clearly can be seen that the copy number of integrated vectors, by comparing the smaller hybridizing DNA fragment (chromosomal rDNA units: ±150 copies) with the larger hybridizing DNA fragment (the integrated vector), is about 100. This is the same for SU50B 2, a southern blot of a sample taken before the adding of the leucine. For SU50B 3, a sample taken after the adding of leucine and the drop in α-galactosidase expression the copy number has decreased to about 10. This experiment shows that the decrease in α-galactosidase expression is accompanied by a decrease in copy number of the α-galactosidase gene. The leucine uptake of the culture is higher after addition of leucine.

The experiments described above show quite surprisingly that the genetic stability of the integrated plasmids is due to the fact that the intracellular production of leucine is required for growth, in spite of the presence of an appreciable amount of extracellular leucine. Due to the inefficiency of the LEU2d promoter, production of sufficient amounts of leucine is only possible when a large number of LEU2d genes is present on the chromosome.

Such a large number of integrated genes can be stably maintained when the integration site is in, or directly linked to the ribosomal DNA locus and under proper growth rate conditions and medium composition.

| Media | composition g/l | | | |
|---|---|---|---|---|
| Compound | A | B | C | D |
| NH4Cl |  | 7.6 | 7.6 | 7.6 |
| KH2PO4 | 2.8 | 4.0 |  | 4.0 |
| MgSO4.7aq | 0.6 | 0.6 |  | 0.6 |
| trace metals | 10 | 10 |  |  |
| yeast extract (Difco)## | 5 |  | 10 |  |
| peptone | 0.0 | 0.0 | 20 |  |
| DHW (UF) | 125 | 0.0 |  |  |
| glucose | 5.5 | 20 |  | 20 |
| galactose |  | 10 | 20 | 10 |
| histidine | 0.05 | 0.2 |  | 0.2 |
| vitamin solution | 2 | 1 |  | 1 |
| leucine (added) |  |  |  | 0.05 |
| pH | 5.0 | 5.0 | 5.0 | 5.0 |

DHW: de-proteinized hydrolysed whey ex DMV Netherlands.
UF: ultra filtrated molecular weight cutoff 10 kD.
: yeast extract contains 8–9% w/w leucine.

EXAMPLE 11

PARAMETERS AFFECTING THE STABILITY OF MULTICOPY INTEGRANT SU50B

Strain SU50B (as described in example 10) was cultivated in shake flasks in media C and D. This gives an example of two extreme media ranging from a complex, rich medium to a minimal medium. Medium C (YPGAL) contains 524 mg/l leucine. Surprisingly, the integrant was stable in YPGAL media for many sub-cultivations (see example 8). In medium D and other minimal media with leucine the expression decreased rapidly. The residual concentration of leucine (derived from the yeast extract and peptone) in the medium C decreased from 524 mg/l to 393 mg/l. The leucine concentration in medium D reduced from 50 to about 20 mg/l. The growth rate of the strain in minimal media is about $0.1\ h^{-1}$ while the growth rate on medium C is $0.27\ h^{-1}$. Addition of yeast extract increases the growth rate up to $0.27\ h^{-1}$ combined with an improved stability of the α-galactosidase production. The complex media not only increase the growth rate, but also increase the α-galactosidase concentration in the culture.

These experiments clearly show that the multicopy integrant was stable at high growth rates in the presence of leucine. Based on this finding an efficient fermentation process can be developed meaning a substantial amount of protein per culture volume per hour can be obtained.

EXAMPLE 12

EXPRESSION OF THE SYNTHETIC LIPASE GENES IN *Hansenula polymorpha*

The synthetic lipase genes were integrated in the *H. polymorpha* genome using the following procedure (FIG. 26; in each figure of this example the used restriction enzyme recognition sites are marked with an asterisk;

restriction recognition sites between brackets are removed due to the cloning procedure):

a. Plasmid pUR6038 (FIG. 27) was digested to completion with the restriction enzymes EcoRI and EcoRV. After separation of the fragments by agarose gel electrophoresis the vector fragment was isolated as described in Example 2.

b. Several different synthetic cassettes were assembled as described in Example 3. These cassettes encoded a number of amino acids necessary for a correct joining of the invertase signal sequence with different length of the-premature lipase gene. This was done to establish the most optimal construct with respect to expression, processing and export of the lipase enzyme. Furthermore, these cassettes had EcoRI and EcoRV ends. Typical examples are given in FIG. 26.

c. The assembled cassettes were ligated in the vector prepared under a.

d. The plasmids thus obtained (pUR6850, 6851 and 6852 FIG. 28) were partially digested with the restriction enzyme XhoI and the linearized plasmid was isolated.

e. Plasmid pUR3501 (21, FIG. 29) was partially digested with XhoI. After agarose gel electrophoresis a DNA fragment of approximately 1500 bp was isolated, containing the H. polymorpha methanol oxidase (MOX) promoter followed by the first amino acids of the S. cerevisiae invertase signal sequence XhoI DNA fragment from position 0 to 1500 from pUR3501).

f. The 1.5 kb fragment from e. was ligated in the vector fragments as prepared in d resulting in plasmids UR6860, 6861, 6862 FIG. 30.

g. The ligation mixture was transformed to E. coli. From single colonies, after cultivation, the plasmid DNA was isolated and the correct plasmids, as judged by restriction enzyme analysis, were selected and isolated in large mounts.

h. The correct plasmids obtained in step g. (eg. pUR6860, 6861, 6862 FIG. 30) were digested to completion with BamHI, after which the sticky ends were filled in with Klenow polymerase (example 2). As the next step the linear plasmids were digested with EcoRI, and the filled in BamHI-EcoRI DNA fragments comprising the MOX promoter, invertase signal sequence and synthetic lipase gene with a length of approximately 2.5 kb were isolated out of agarose gel.

i. Plasmid pUR3511 (the H. polymorpha methanol oxidase (MOX) terminator cloned in the BamHI, HincII restriction sites of pEMBL9, FIG. 31) was digested with SmaI and EcoRI, after which the vector was isolated out of an agarose gel.

j. The pUR3511 vector and the 2.5 kb fragments, obtained in h., were ligated and cloned in E. coli. In the constructs obtained, the lipase gene is followed by the MOX transcription terminator. Typical examples of these constructs are pUR6870, 6871 and 6872 (FIG. 32).

k. These plasmids were digested with EcoRI and HindIII, after which the fragments of approximately 3 kb. were isolated from an agarose gel. The sticky ends were filled in with Klenow polymerase.

l. Plasmid pUR3513; this is plasmid YEp13 (37) from which the 2 μm sequences have been deleted by removal of a SalI fragment (FIG. 33) was digested with PvuII.

m. The linear plasmid pUR3513 and the fragments obtained in k. were ligated to obtain the final constructs among which pUR6880, 6881 and 6882 (FIG. 34).

Introduction of the expression cassettes in the H. polymorpha genome.

Transformation of plasmid DNA to the Hansenula polymorpha strain A16 using selection for LEU$^+$ phenotype can be performed as described by (21, 38, 39).

Analysis of the integrants can be performed using the Southern blot procedure (7).

EXAMPLE 13

PRODUCTION OF GUAR α-GALACTOSIDASE IN Hansenula polymorpha USING MULTICOPY INTEGRATION In this example the expression of a heterologous protein, α-galactosidase from guar Cyamopsis tetragonoloba), using multicopy integration in Hansenula polymorpha, is described. The gene encoding α-galactosidase was fused to homologous expression signals as is described in Overbeeke (21) resulting in the expression vector pUR3510. The α-galactosidase expression cassette of pUR3510 consists of the H. polymorpha methanol oxidase promoter, the S. cerevisiae invertase signal sequence, the α-galactosidase gene (encoding mature α-galactosidase) and the H. polymorpha methanol oxidase terminator. This expression cassette was isolated and inserted in the multicopy integration vector pUR2790 resulting in pUR3540. The multicopy integration vector pUR3540 was transformed to H. polymorpha and surprisingly multicopy integrants were obtained. The obtained multicopy integrants expressed and secreted the plant protein α-galactosidase. This example clearly demonstrates that it is possible to obtain multicopy integrants in H. polymorpha and these multicopy integrants can be used for the production of proteins. Also it appeared that multicopy integrants in H. polymorpha were obtained using S. cerevisiae ribosomal DNA sequences and a S. cerevisiae deficient selection marker. All DNA manipulations were carried out using standard techniques as described in Maniatis (7).

The plasmid pUR3510 (21) was digested with HindIII and BamHI and the DNA fragment containing the α-galactosidase expression cassette was isolated. The multicopy integration vector pUR2790 is derived from pUR2740 by replacing the BglII-HindIII 500 bp fragment containing S. oligorhiza DNA and a 100 bp S. cerevisiae ribosomal DNA by a BglII-HindIII polylinker sequence containing multiple cloning sites. The multicopy integration vector pUR2790 was partially digested with HindIII and digested to completion with BglII and subsequently the vector fragment was isolated. The BglII-HindIII vector fragment and the HindIII-BamHI fragment, containing the α-galactosidase expression cassette, were ligated resulting in the multicopy integration vector pUR3540 (see also FIG. 35; all used restriction recognition sites are marked with an asterisk). The ligation mixture was transformed to E. coli. From single colonies, after cultivation, the plasmid DNA was isolated and the correct plasmids, as judged by restriction enzyme analysis, were selected and isolated in large amounts.

The multicopy integration vector pUR3540 was linearized with SmaI and the linearized vector pUR3540 was transformed to H. polymorpha A16 (LEU2$^-$) using the procedure described by Roggenkamp et al (39). The LEU2$^+$ colonies, being the multicopy integrants, were isolated and used for further experiments. The multicopy integrant and the parent strain A16 as a control were grown under nonselective conditions (1% Yeast Extract, 2% Bacto-peptone, 2% glucose for 40 hours at 37° C.) and chromosomal DNA was isolated as described by Janowicz et al. (40). The total DNA was digested with HindIII and the digested chromosomal DNA was analyzed by Southern hybridization (7). An XhoI 878 bp fragment, containing a part of the methanol oxidase promoter [position −1313 to position −435, Ledeboer (41)], was labelled with $^{32}P$ and used as a probe. The result of this hybridization experiment is shown in FIG. 36, (lane 2 parent strain and lane 1 multicopy integrant). In lane 2, the parent strain, a DNA fragment of approximately 14 kb can be seen to hybridize with the methanol oxidase promoter probe, corresponding to a DNA fragment containing the entire methanol oxidase gene which is present in a single copy in the genome. In lane 1, the multicopy integrant, an additional hybridization signal was obtained,corresponding to a DNA fragment of approximately 8 kb. This fragment is part of the integrated vector pUR3540 being the HindIII fragment containing amongst others the α-galactosidase expression cassette and the methanol oxidase promoter. By comparison of the intensities of the hybridization signals in lane 2 it can be estimated that over 20 copies of the multicopy integration vector are integrated in the *H. polymorpha* genome. The multicopy integrant was analyzed for α-galactosidase expression as described by Overbeeke (21). Upon induction with methanol α-galactosidase was detected in the medium using the enzyme activity assay.

This example clearly demonstrates that multicopy integration can be achieved in *H. polymorpha* and thus the multicopy integration system can be used for the production of (e.g. heterologous) proteins in *H. polymorpha*. This example also demonstrates that it is possible to obtain multicopy integration of an expression vector in the genome of a yeast (e.g. *H. polymorpha*) using the two prerequisites, ribosomal DNA sequences and a deficient selection marker. Such a selection marker can be homologous or originating from another host (e.g. *S. cerevisiae*) as long as the expression level of the deficient gene is below a critical level.

EXAMPLE 14

MULTICOPY INTEGRATION IN KLUYVEROMYCES

In this example a procedure is described to obtain multicopy integration of a plasmid vector in the genome of *Kluyveromyces marxianus* var. *lactis*. Multicopy integration vectors were constructed containing ribosomal DNA sequences originating from *S. cerevisiae* and deficient selection markers origination from the multicopy integration vectors (pMIRY6-TΔ1, pMIRY6-TΔ2 and pMIRY6-TΔ3). The multicopy integration vectors were transformed to a TRP⁻ *K. marxianus* strain surprisingly resulting in transformants having multiple copies of the vector integrated in the genome of the Kluyveromyces strain. Also this example clearly demonstrates that multicopy integration can be obtained in yeasts using either homologous or heterologous deficient selection markers.

From the multicopy integration vectors pMIRY6-TΔ1, pMIRY6-TΔ2 and pMIRY6-TΔ3 (see example 9) the *S. cerevisiae* ribosomal DNA was removed by digestion with SphI, isolation of the vector fragment followed by ligation of the vector fragment. In the resulting vector a 4400 bp EcoRI *K. marxianus* ribosomal DNA fragment (42, FIG. 37) was cloned in the EcoRI site resulting in the multicopy integration vectors pMIRK7ΔT1, pMIRK7ΔT2 and pMIRK7ΔT3 (FIG. 38). The multicopy integration vectors, after linearization with SacI, were transformed to the *K. marxianus* strain MSK 110 (a, URA-A, TRP1:URA3), (43) using the LiAc procedure (44). Transformants were selected for TRP⁺ phenotype. The obtained integrants were grown under non-selective conditions (0.67% Yeast Nitrogen Base with amino acids, 2% glucose, 30° C.), for 6–7, 30–35 and 60–70 generations. This was performed by growing the integrants to OD 550 nm of 2 to 3, dilution in fresh non-selective medium to OD 550 nm of 0.1 and followed by growth to OD 550 nm of 2 to 3. This cycle was repeated several times. From these integrants total DNA was isolated (45), digested with PstI and separated on a 0.8% agarose gel, followed by Southern analysis using the EcoRI-PstI fragment of the *K. lactis* ribosomal DNA (FIG. 37) as a probe. In FIG. 39 the result obtained with the integrant of pMIRK7ΔT1 are shown. In lane 5 the hybridisation of the rDNA probe with the digested chromosomal DNA of the host strain is shown, the rDNA probe hybridizes with the ±150 repeated copies of the rDNA unit. In lane 1 the pMIRK7ΔT1 integrant is shown. The hybridisation with rDNA copies, as for the parent strain, can be seen but in addition the repeated integrated copies of the multicopy integration vector. As a control the hybridisation result of the linearized multicopy integration vector with the rDNA probe (lane 6) is shown. The relative intensity of the hybridization signal can be used to estimate the copy number of integrated vector. The hybridisation signal with the rDNA units corresponds ±150 copies. Comparison of the intensity of hybridisation signal of the integrated copies of the vector with the intensity of the hybridization signal with the rDNA units the copy number can estimated to be at least 50. This result shows that surprisingly multicopy integration can also be obtained in the yeast genus Kluyveromyces. In lane 2, 3 and 4 the integration pattern is shown after non-selective growth of the multicopy integrant, also used in lane 1, for 6–7, 30–35 and 60–70 generations respectively. It can clearly be seen that the relative intensity of the hybridisation signals with the integrated vector does not decrease. This surprising finding proves that the multicopy integration is completely Stable even after prolonged growth under non-selective conditions. Similar results were obtained using the multicopy integrants of pMIRK7ΔT2 and pMIRK7ΔT3.

This example clearly demonstrates that it is possible to obtain multicopy integration in Kluyveromyces using a multicopy integration vector with the two prerequisites ribosomal DNA sequences and a deficient selection marker, in this example even a heterologous selection marker. The multicopy integrants are stable for at least 60 generation under non-selective conditions. By analogy with the examples 8 and 13, production of a protein in Kluyveromyces using multicopy integrants can be obtained by insertion of an expression cassette, with a gene coding for a protein of commercial interest, in the multicopy integration vector and transformation of the resulting vector including the expression cassette. These multicopy integrants can be used for the production of the protein of commercial interest. Because of the unique properties of the multicopy integration system, high copy number and high genetic stability, these multicopy integration transformants can be used in any known fermentation production process for the production of a, commercially interesting, protein.

REFERENCES

1. Kingsman, S. M. et al., (1985), Biotech. Gen. Eng. Rev., 12, 377–416.
2. Kingsman, A. J. et al., (1981), J. Mol. Biol., 145, 619–632.
3. Tschumper, G. and Carbon, J., (1980), Gene, 10, 157–166.
4. Dobson, M. J. et al., (1982), Nucleic Acids Research, 10, 2625–2637.
5. Tuite, M. F., (1982), EMBO, 1, 603–608.
6. Roeder, G. C. and Fink, G. R., (1983), Mobile Genetic Elements (ed J. A. Shapiro), Academic Press, 300–328.
7. Maniatis, T. et al. Molecular cloning. A Laboratory Manual. Cold Spring Harbor Laboratory (1982), ISBN 8-87969-136-0.

8. Bates, P. F. and Swift, R. A., (1983), Gene, 26, 137–146.
9. Hohn, B., (1979), Methods in Enzymology, Academic press, New York, 68, 299–309.
10. Barone, A. D. et al., (1984), Nucleic Acids Research, 12, 4051–4061.
11. Dente, L. et al., (1983), Nucleic Acids Research, 11, 1645–1655.
12. Messing, J., (1983), Methods in Enzymology, 101 Academic press, New York.
13. Friedman et al., (1982), Gene, 18, 289–296.
14. Sanger, F. et al., (1977), Proc. Natl. Acad. Sci. U.S.A., 74, 5463–5467.
15. Biggin, M. D. et al., (1983), Proc. Natl. Acad. Sci. U.S.A., 80, 3963–3965.
16. von Heijne, G., and Abrahmsen, L., (1989), FEBS Letters, 244, 439–446.
17. Marinus, M. G. et al., (1973), Mol. Gen. Genet. 127, 47–55.
18. Bolivar, F. et al., (1977), Gene, 2, 95–113.
19. Jorgensen, R. A. et al., (1979), Mol. Gen. Genet. 177, 65–72.
20. Simon, R. et al., (1983), Biotechnology, 1, 784–791.
21. Overbeeke, N. et al., PCT International Patent Application WO 87/07461.
22. Beggs, J. D., (1978), Nature, 275, 104–109.
23. Verbakel et al., (1987), Gene, 61, 207–215.
24. Kempers-Veenstra, A. E. et al., (1984), EMBO J., 3, 1377–1482.
25. Szostak, J. W. et al., (1979), Plasmid, 2, 536–554.
26. Erhart, E. and Hollenberg, C. P., (1981), Curr. Genet., 3, 83–89.
27. Lopes, T. S., (1990), PhD thesis, Vrije Universiteit Amsterdam, Netherlands
28. Kaback, D. B. and Davidson, N., (1980), J. Mol. Biol., 138, 747.
29. Walmsley, R. M. et al., (1984), Mol. Gen. Genet., 195, 260.
30. Petes, T. D., (1979), Proc. Natl. Acad. Sci. U.S.A., 76, 410–414.
31. Braus G. et al., (1988), Mol. Gen. Genet., 212, 495–504.
32. Kim, S. et al., (1986), Mol. Cell. Biol., 6, 4251–4528.
33. Long, E. O. and Dawid, I. B., (1980), Ann. Rev. Biochem., 49, 727–764.
34. West, R. W. Jr., In "Vectors: a survey of molecular cloning vectors and their uses". Rodrigues, R. L. and Denhart, D. T. (Eds), Butterworth, (1988), 387–404.
35. Yarger, J. G. et al., (1986), Mol. Cell. Biol., 4, 1095–1101.
36. Rose, M. and Botstein, D., (1983), J. Mol. Biol., 170, 883–904.
36B. Chevalier, M. R. et al., (1980), Gene, 11, 11–19.
37. Broach, J. et al., (1979), Gene, 8, 121–133.
38. Gleeson et al., (1986), Journal of General Microbiology, 132, 3459–3465.
39. Roggenkamp et al., (1986), Mol. Gen. Genet., (1986), 202, 302–308.
40. Janowicz, Z. A. et al., (1985), Nucleic Acids Res., 13, 3043–3062.
41. Ledeboer, A. M. et al., (1985) Nucleic Acids Res., 13, 3063–3082.
42. Verbeet, M., PhD Thesis Initiation of transcription of the yeast ribosomal RNA operon, (1983), Vrije Universiteit Amsterdam.
43. Stark, M. J. R. and Milner, J. S., (1989), Yeast, 5, 35–50.
44. Carter, B. L. A., (1988), Agric. Biol. Chem., 50, 1503–1512.
45. Pedersen, M. G., (1983), Carlsberg Res. Commun., 48, 485–503.
46. Mead, D. A., (1986), Protein engineering, 1, 74–76.

BRIEF DESCRIPTION OF THE FIGURES

In the figures of the different plasmids the order of length is given.

FIGS. 2A–2B The complete nucleotide sequence of the *P. glumae* lipase gene; for details see text.

FIG. 3A–3C schematic drawing of the construction pUR6103; for details see text.

FIGS. 5A–5G The complete nucleotide sequence of the synthetic lipase gene in pUR6038.

FIG. 5G The nucleotide sequence of the 3' flanking region of the synthetic lipase gene in pUR6600.

FIGS. 6A, 6B, 6C1, 6C2 An example of the construction of a cassette in the synthetic lipase gene.

FIG. 7A–7B schematic drawing of the construction of plasmid pUR6131; for details see text.

FIG. 8 An example of the improved resistance of a mutant lipase in a detergent system.

SU50B 1: SU50B grown in shake flask.

SU50B 2: SU50B at the start of the continuous culture.

SU50B 3: SU50B after the addition of leucine.

Figure 1:
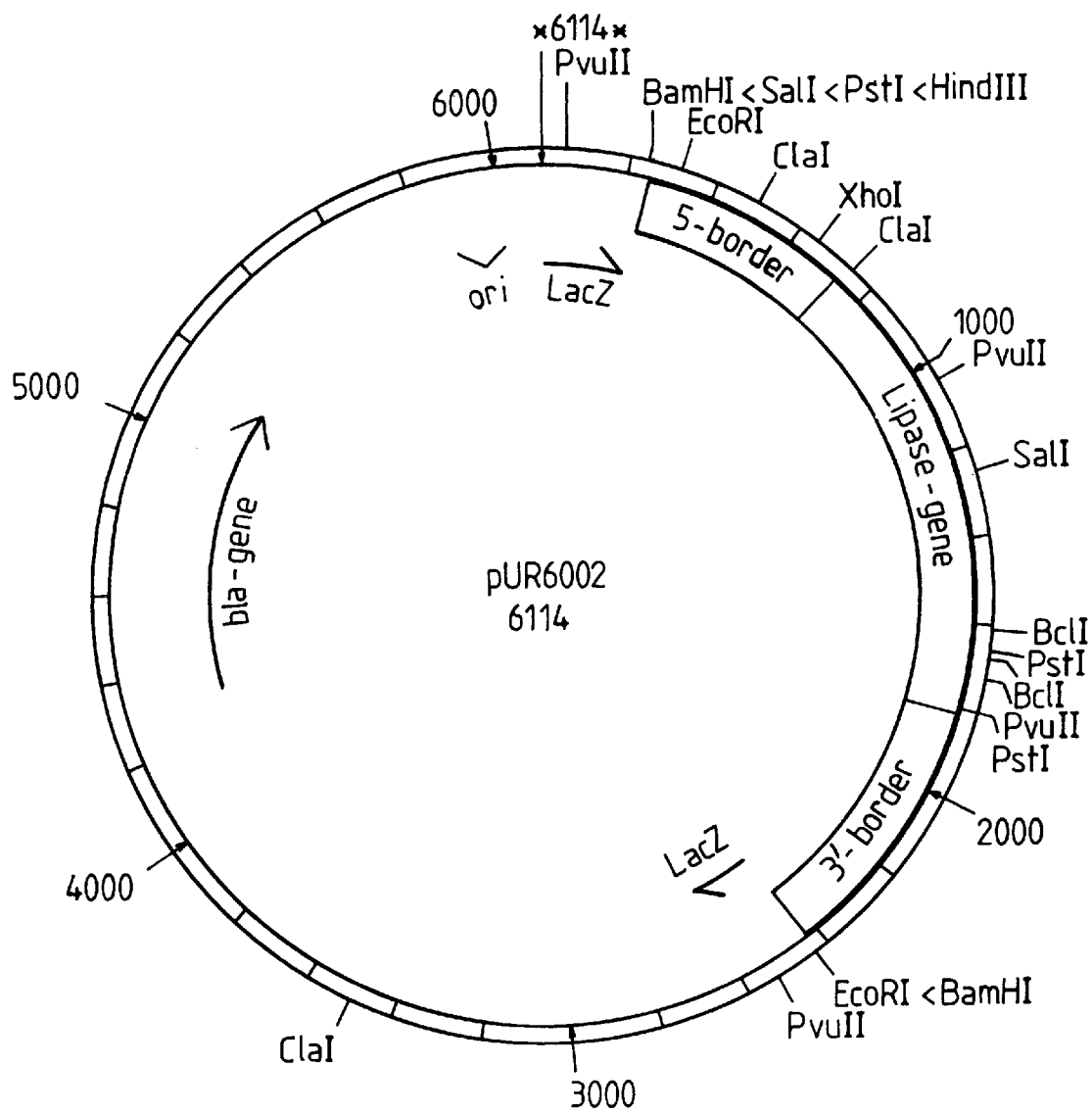
FIG. 1 A schematic drawing of the plasmid pUR6002 comprising the *P. glumae* lipase gene.
Figure 3A:
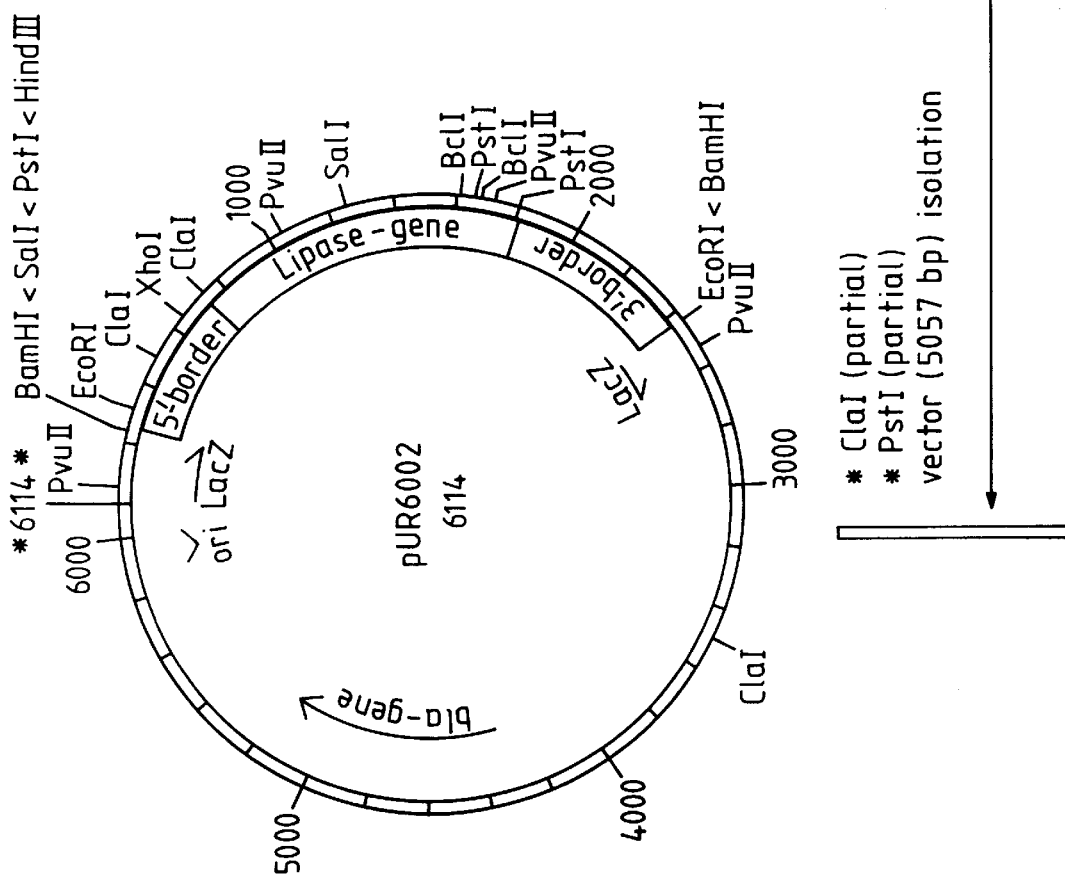
Figure 3C:
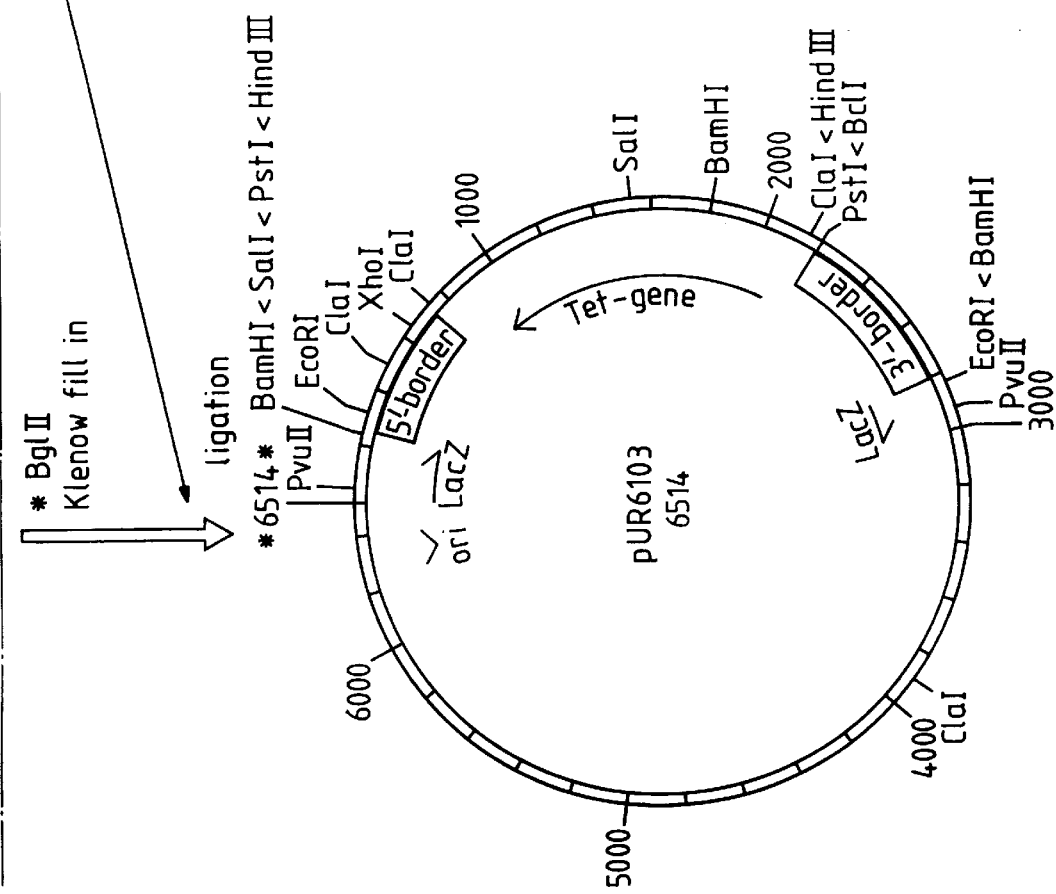
Figure 4A:
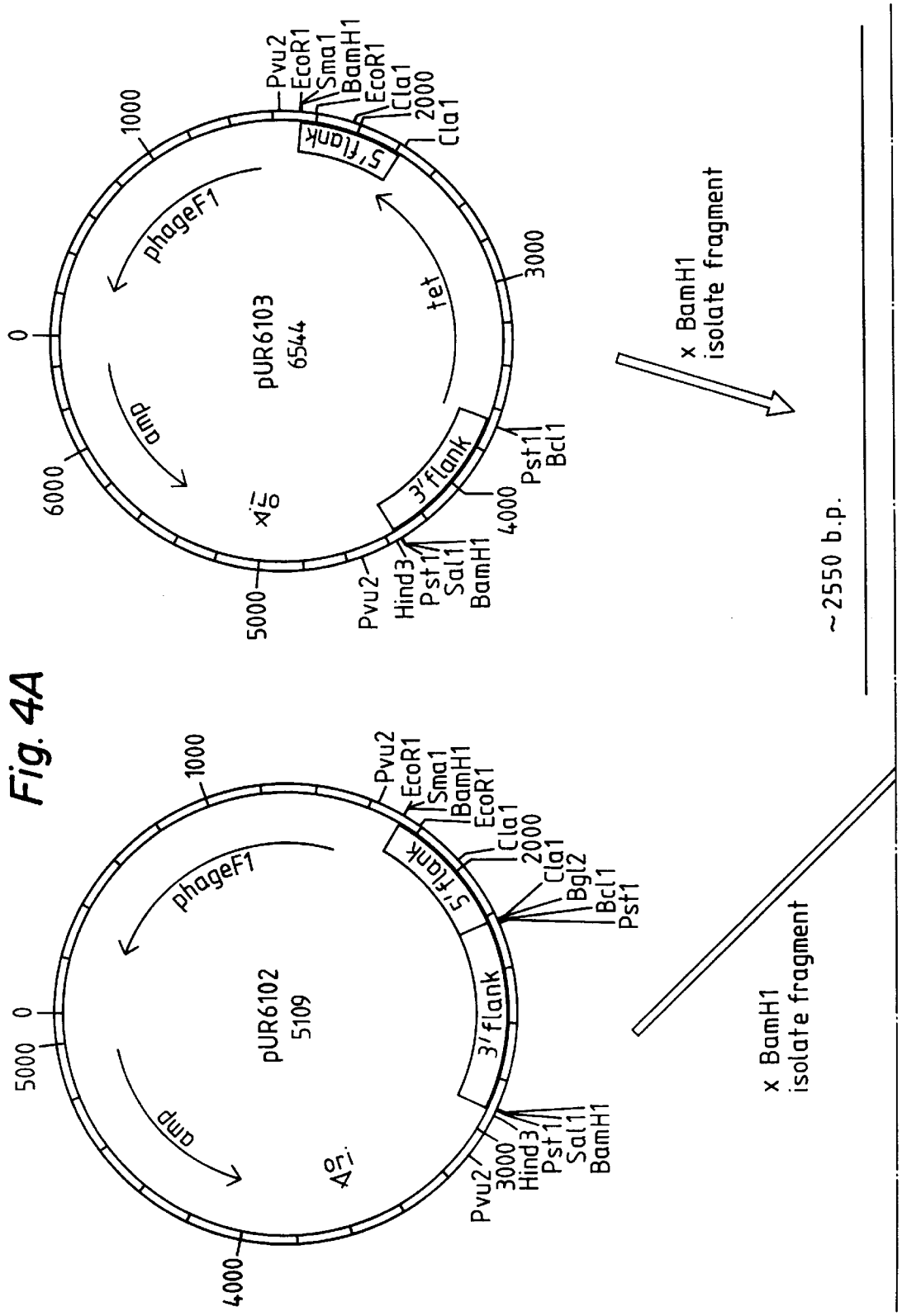
FIG. 4A–4B schematic drawing of the construction of the plasmids pUR6107 and pUR6108; for details see text.
Figure 4B:
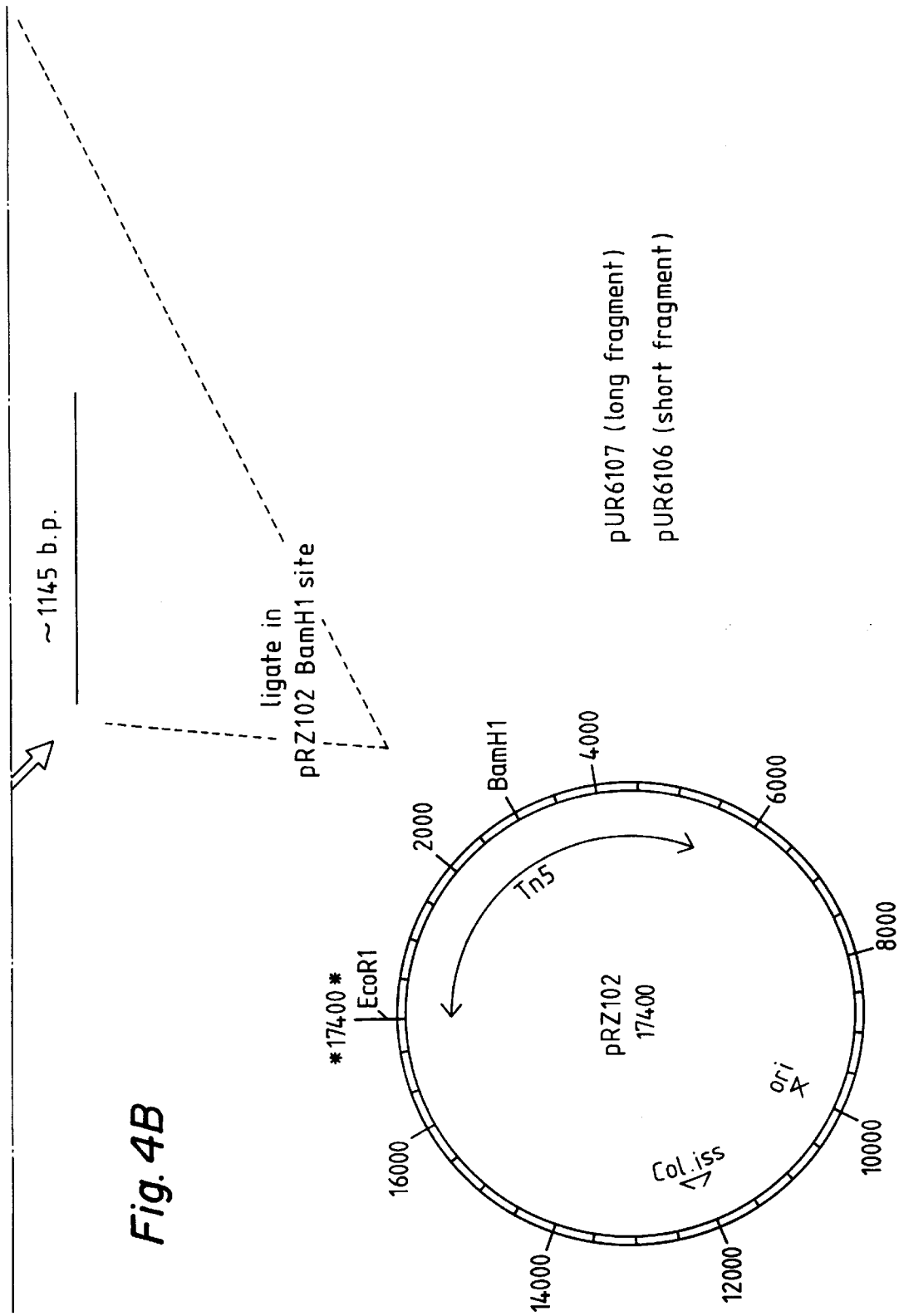
Figure 7B:
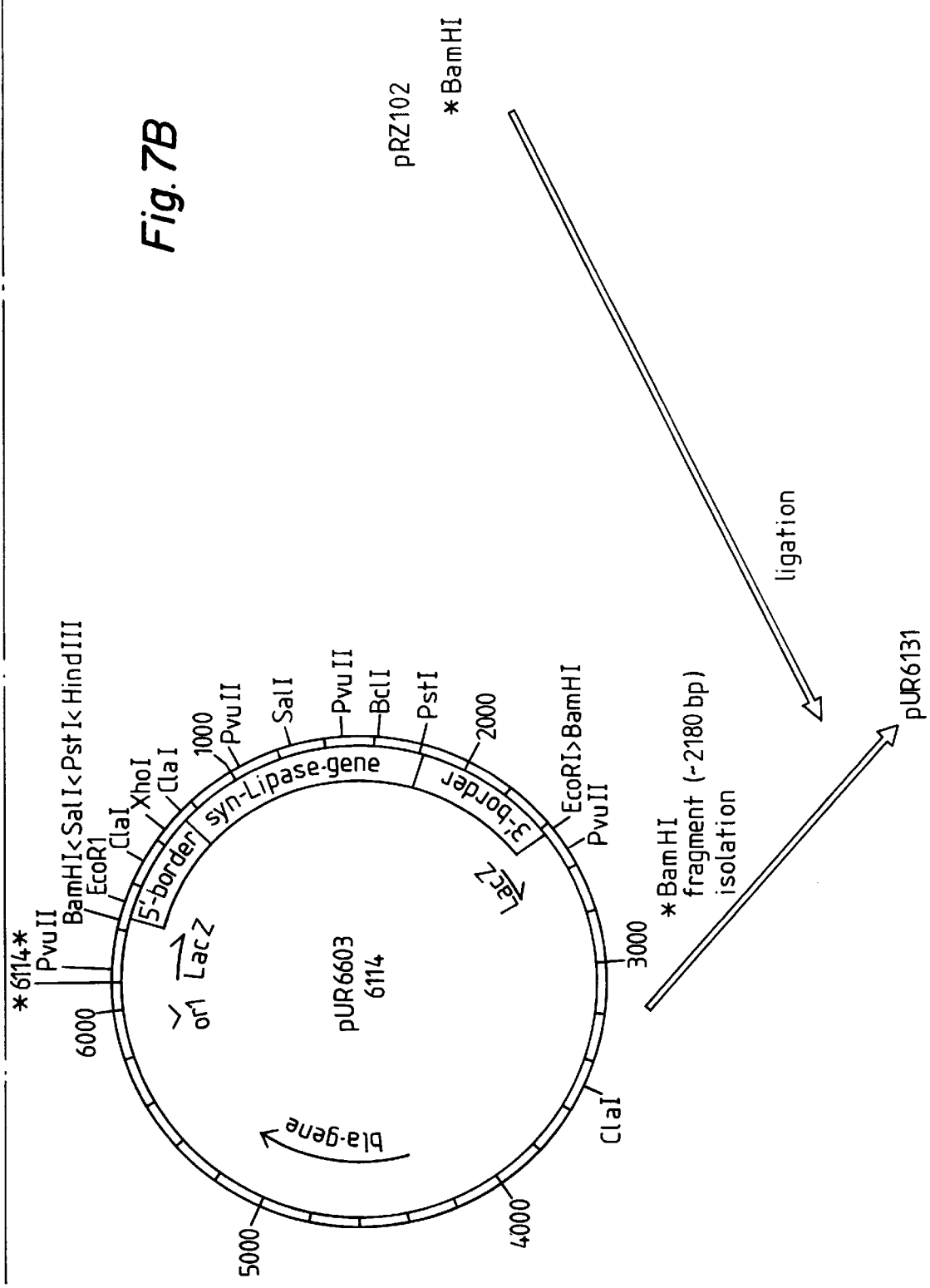
Figure 9A:
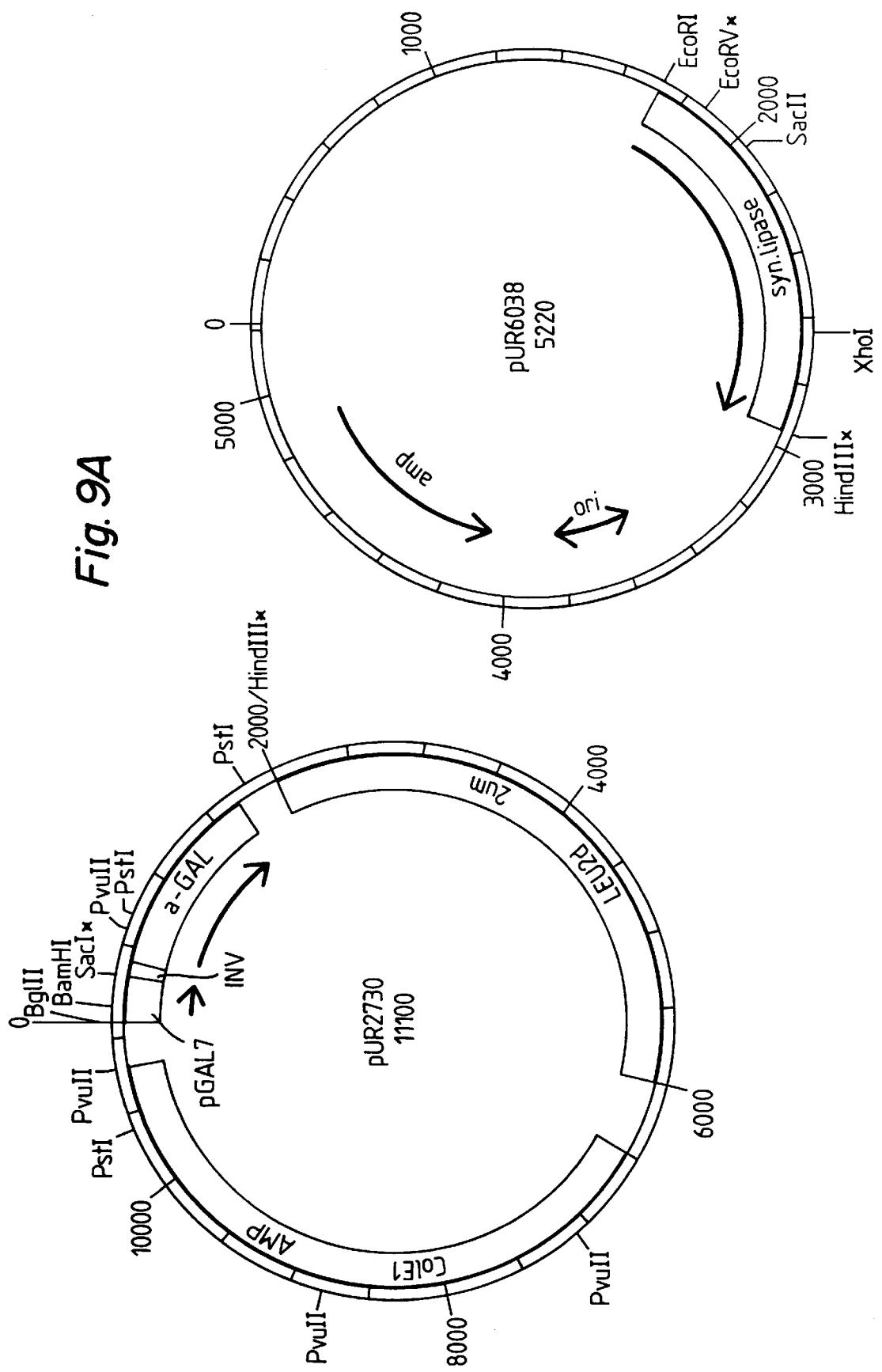
FIG. 9A–9B schematic drawing of the construction of the plasmid pUR6801. Plasmid pUR6801 is a *S. cerevisiae/E. coli* shuttle vector comprising the synthetic lipase gene with yeast expression- and secretion sequences.
Figure 9B:
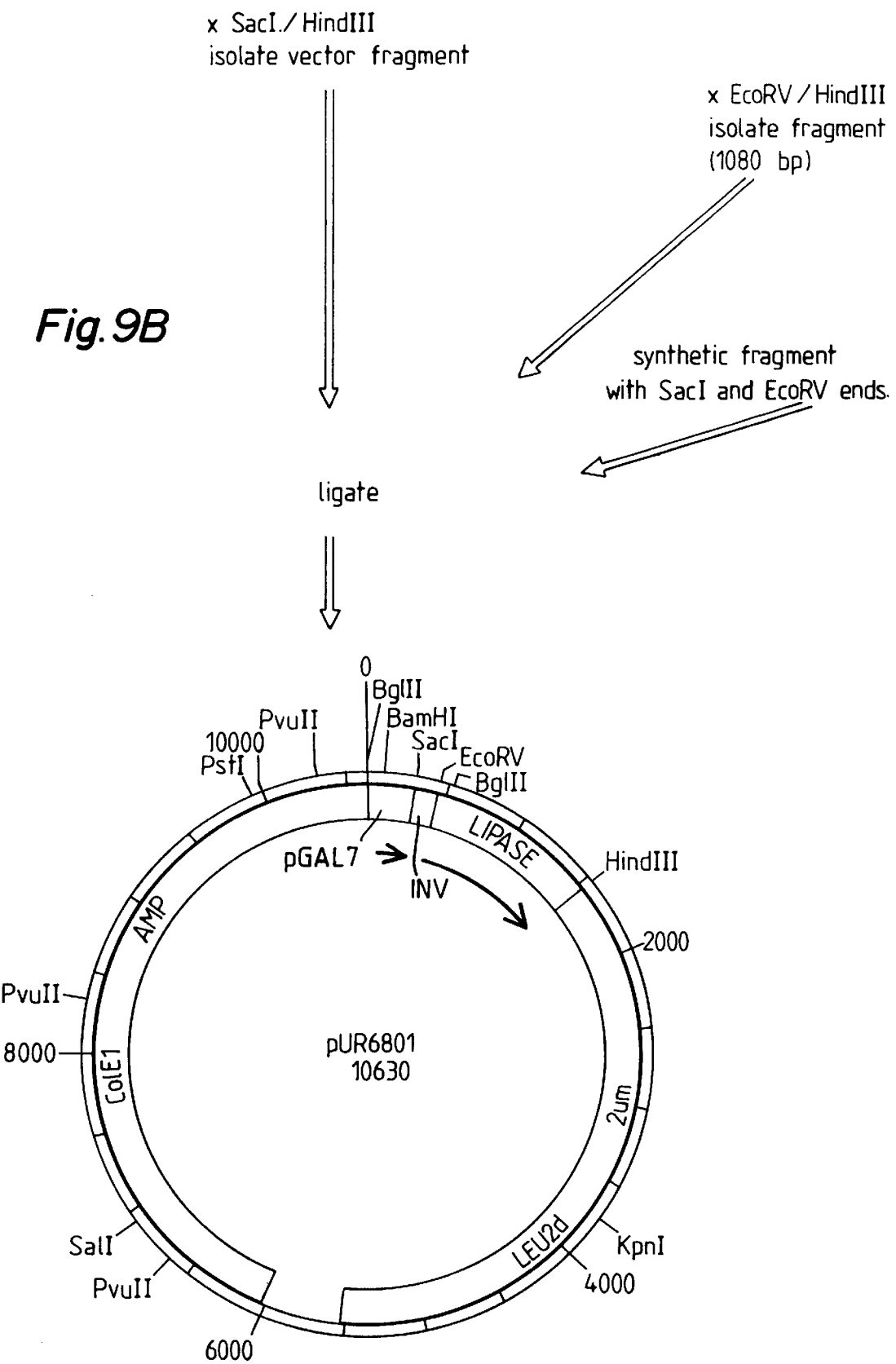
Figure 10:
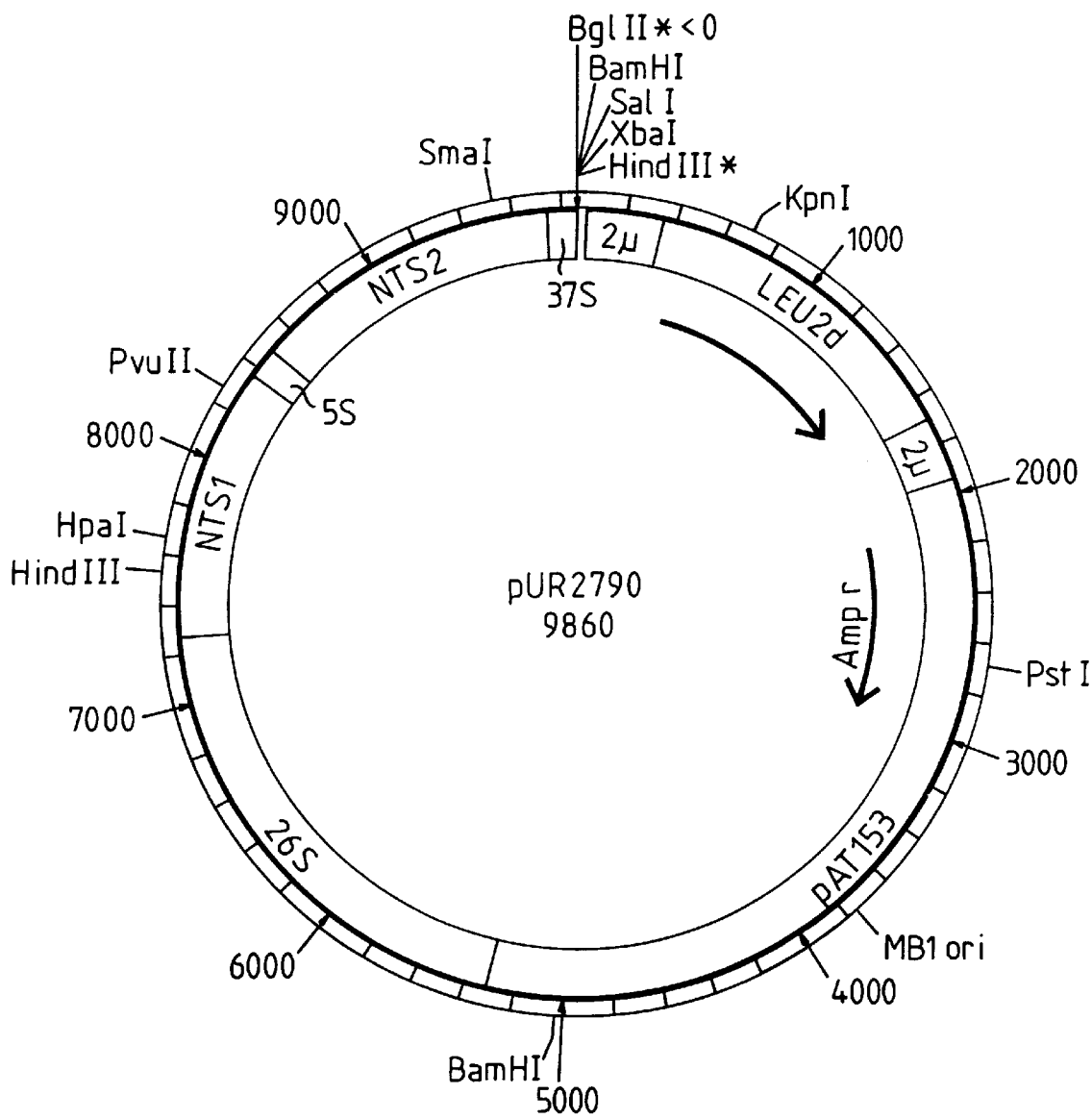
FIG. 10 A schematic drawing of the multicopy integration vector pUR2790.
Figure 11A:
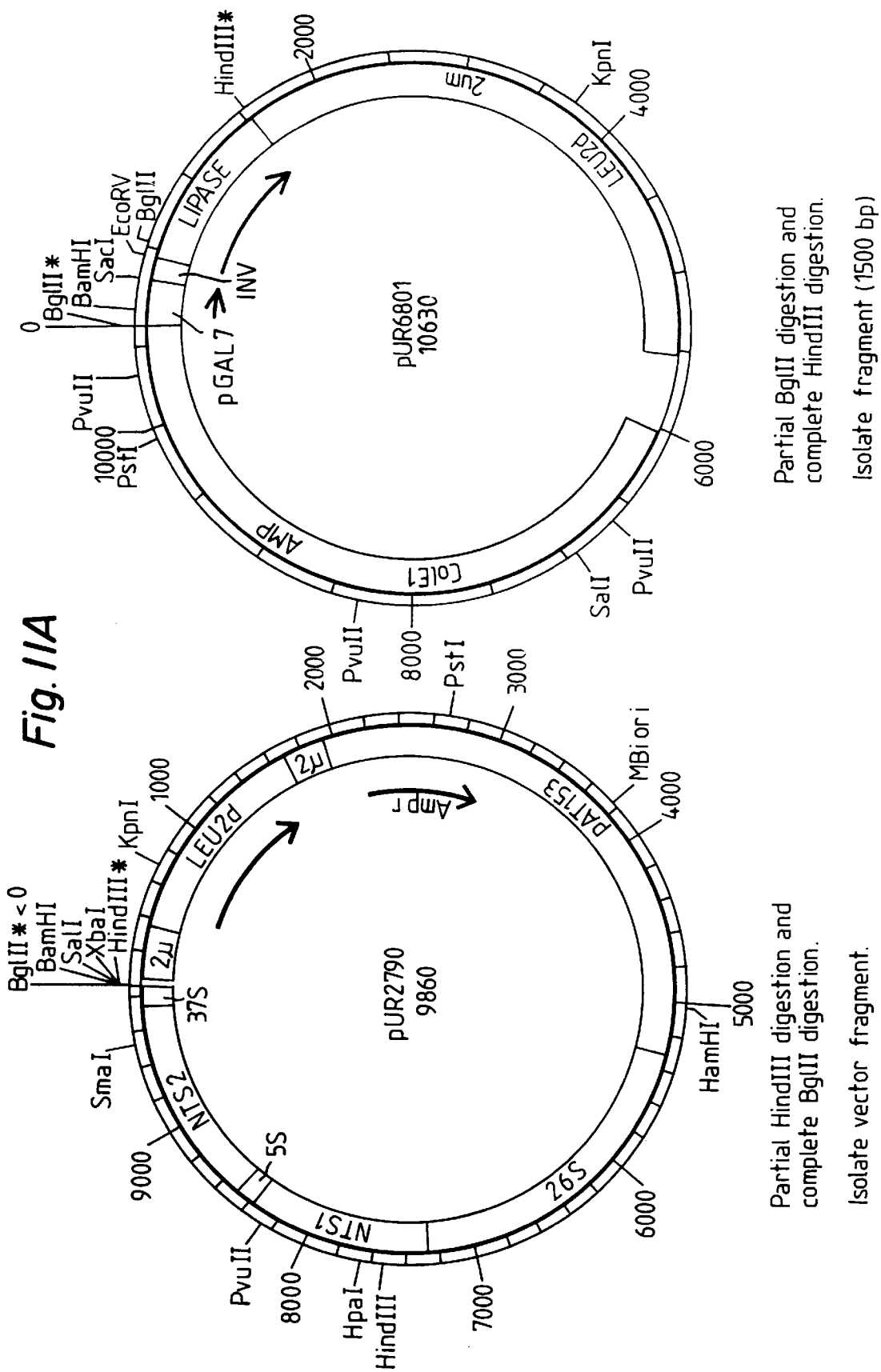
FIG. 11A–11B A schematic drawing of the construction of pUR6803. Plasmid pUR6803 is a multicopy integration vector comprising the lipase expression cassette.
Figure 11B:
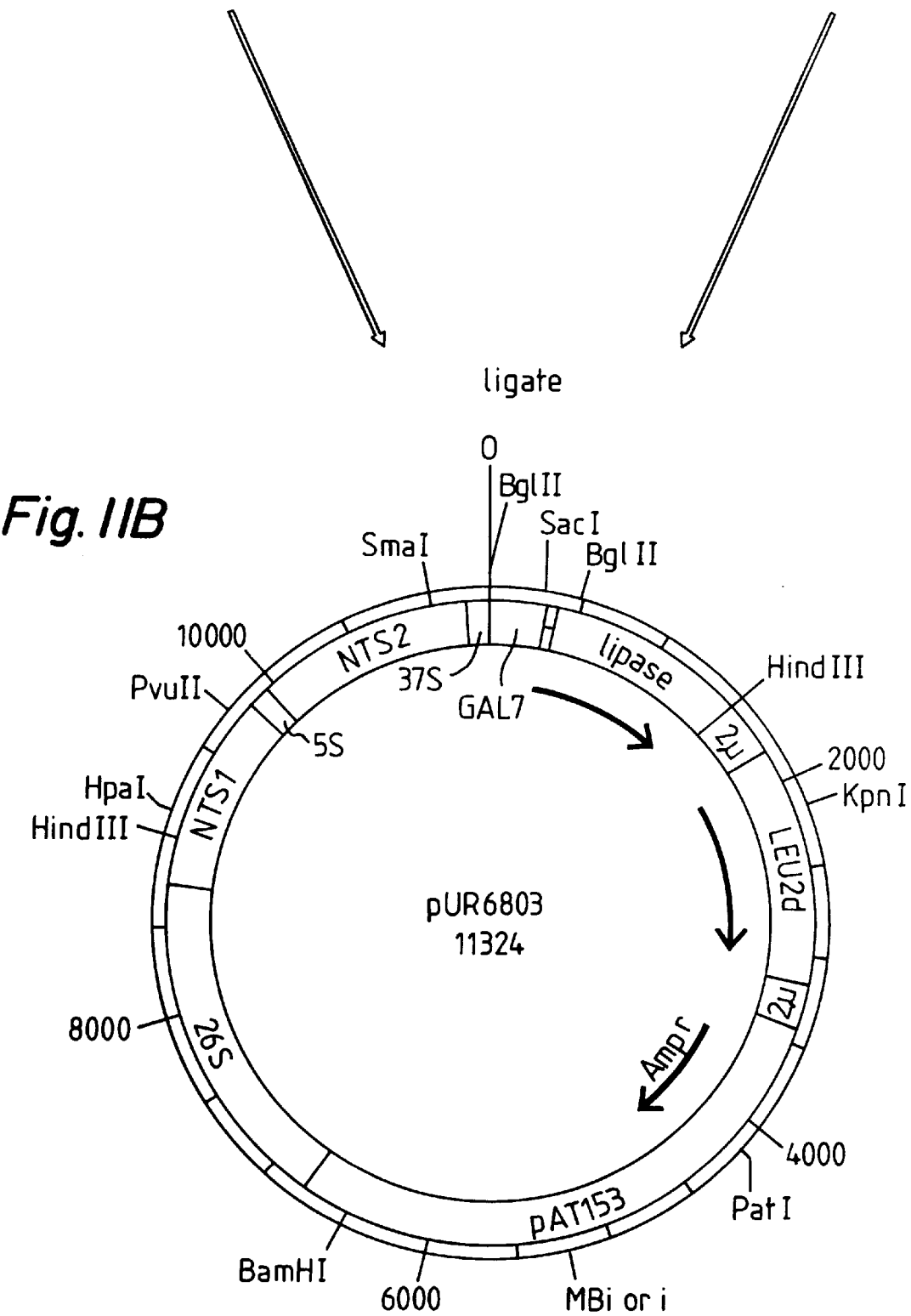
Figure 12A:
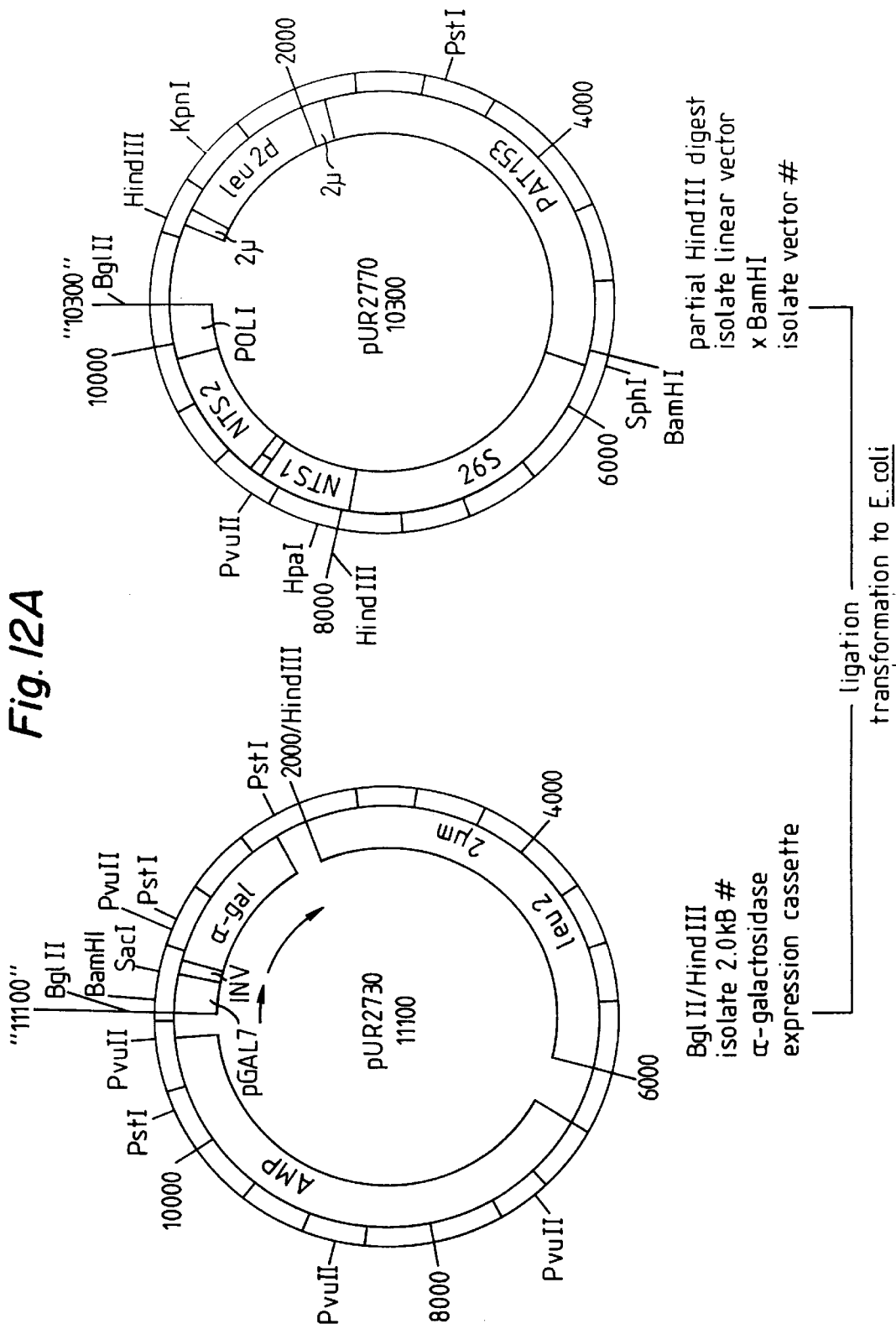
FIG. 12A–12B A schematic drawing of the multicopy integration vector pUR2774 comprising the α-galactosidase expression cassette.
Figure 12B:
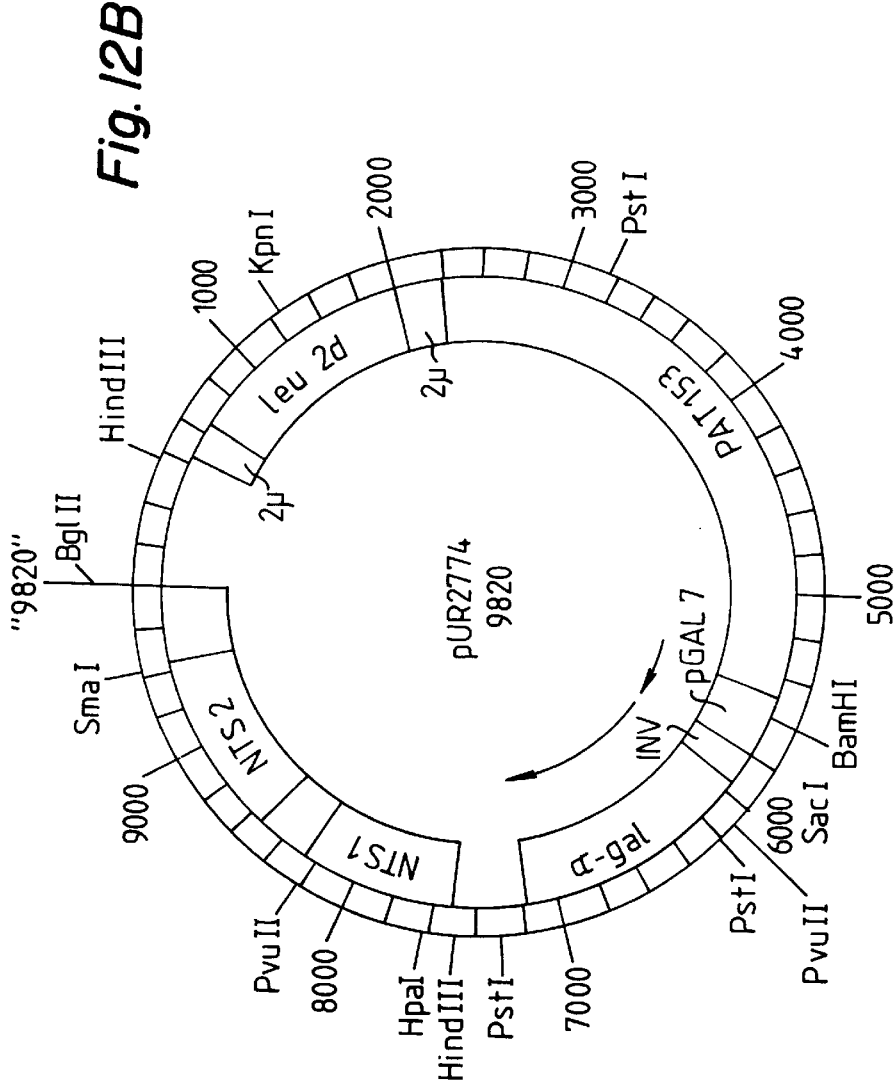
Figure 13A:
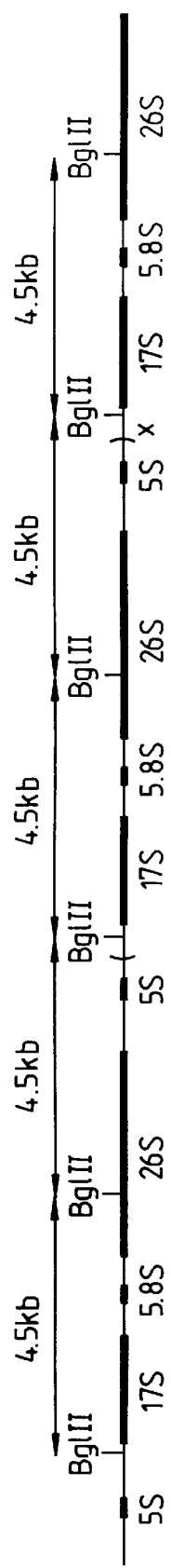
Figure 13B:
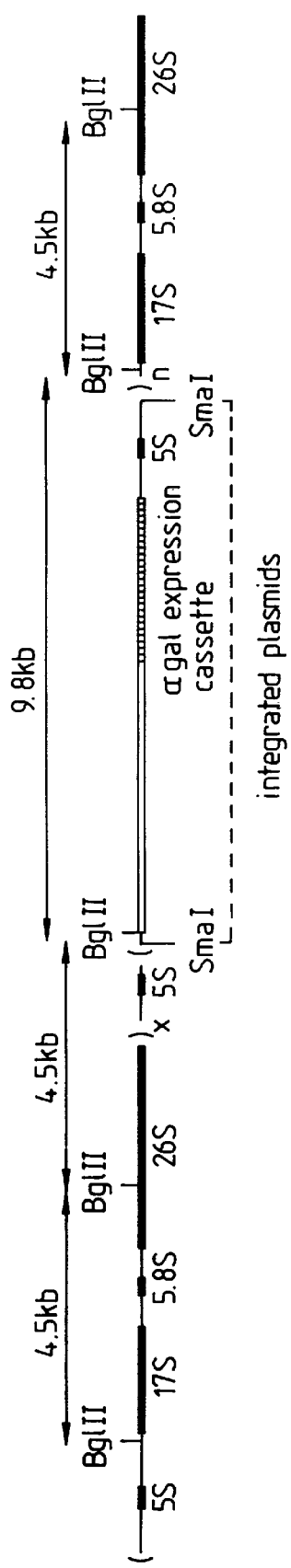
Figure 14:
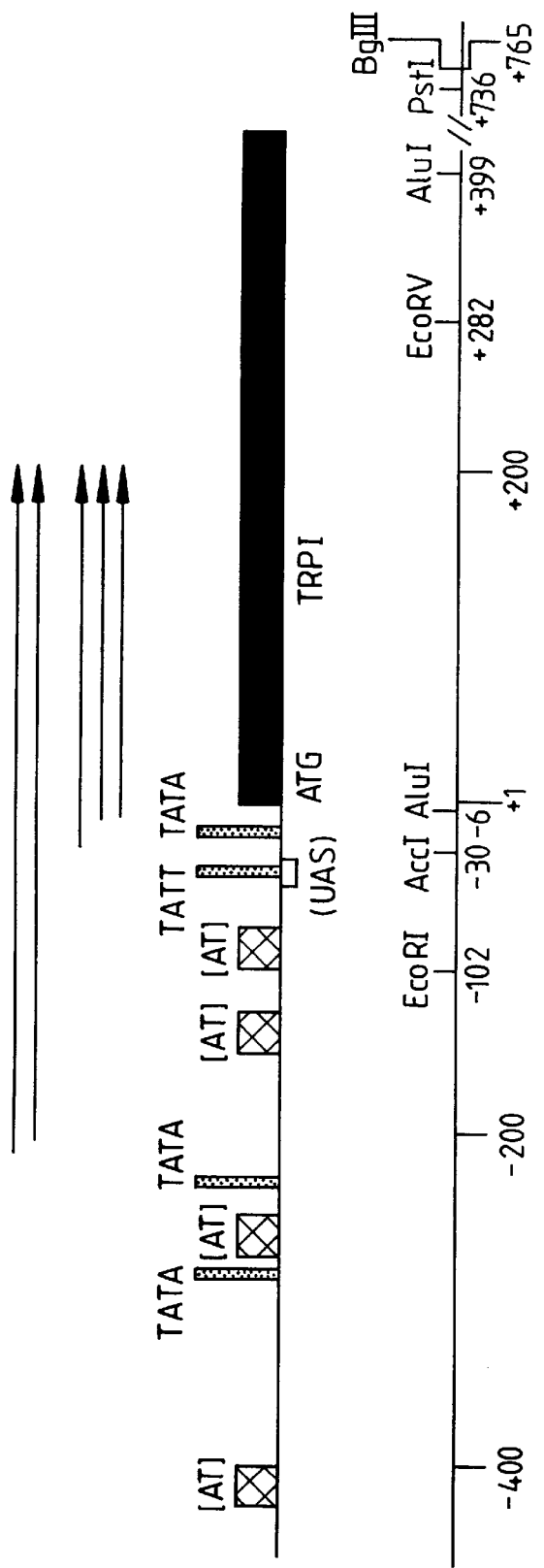
Figure 15A:
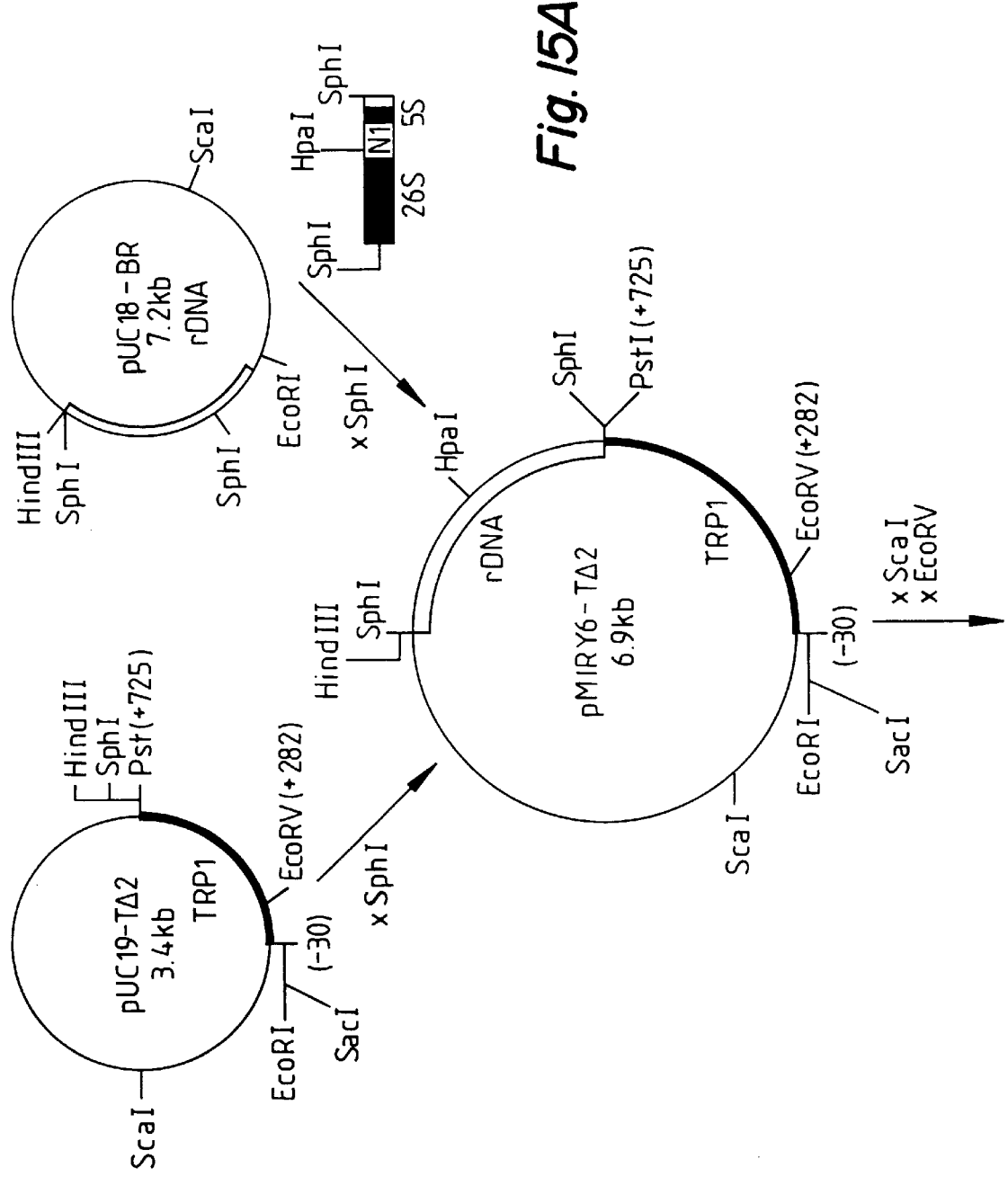
FIG. 15A–B
  A. A schematic drawing of the genetic organization of the ribosomal DNA locus of *S. cerevisiae*.
  B. A schematic drawing of the genetic organization of a multicopy integration of pUR2774 in the ribosomal DNA locus of *S. cerevisiae* (multicopy integrant SU50B).
Figure 15B:
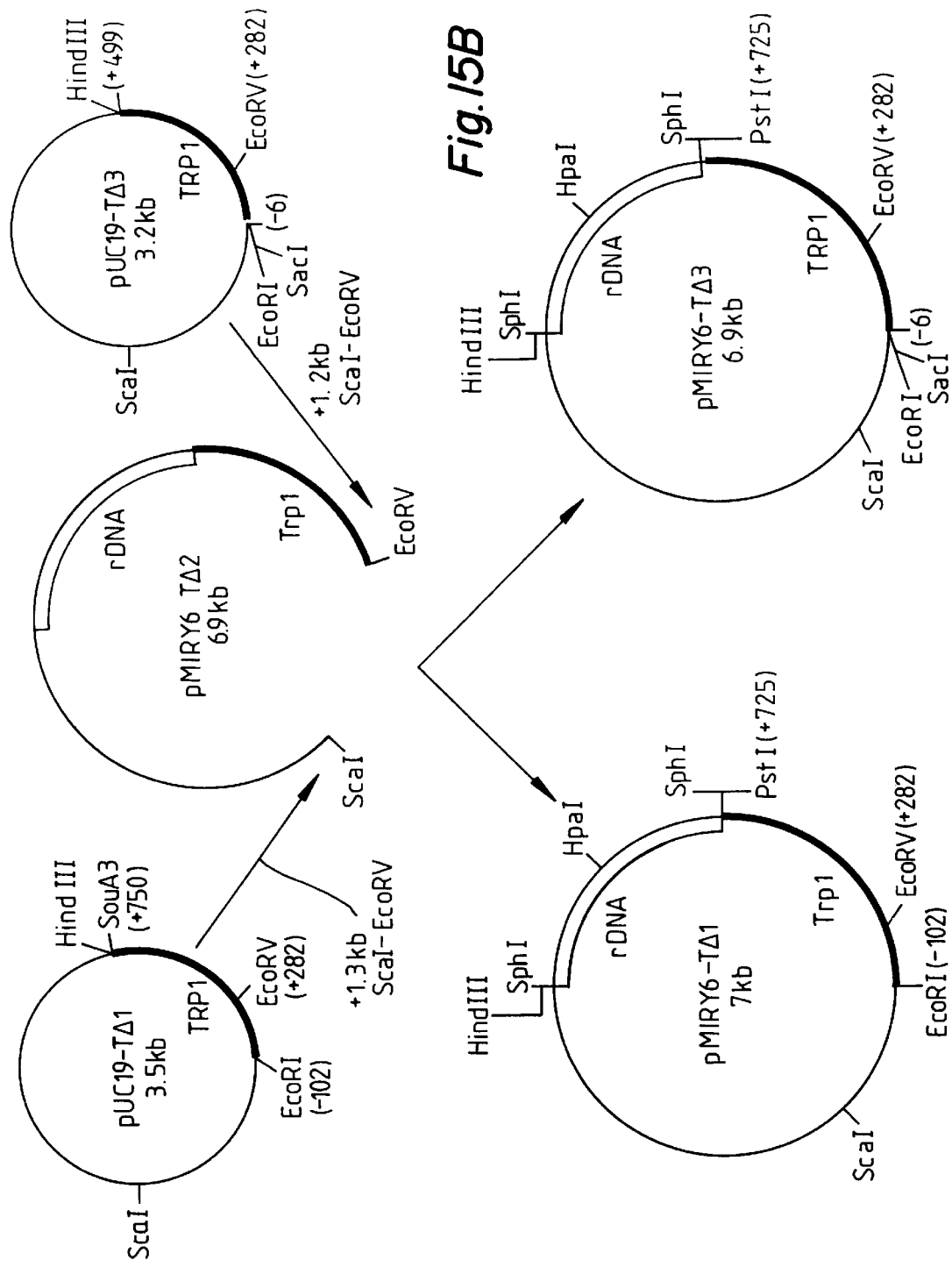
Figure 16:
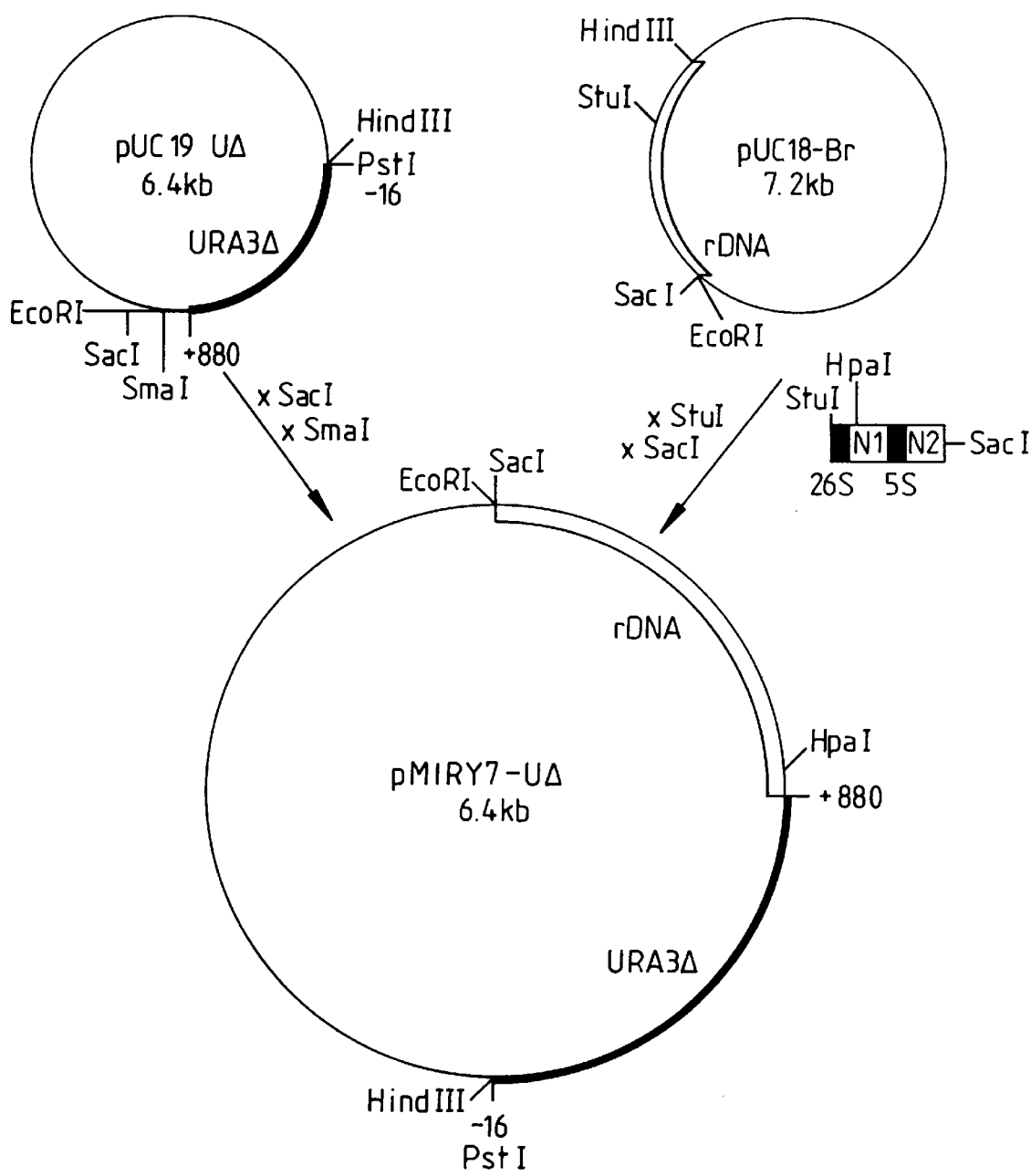
FIG. 16 Ethidium bromide stained agarose gel of undigested and BglII digested total DNA of the multicopy integrants SU50B and SU50C.
Figure 17:
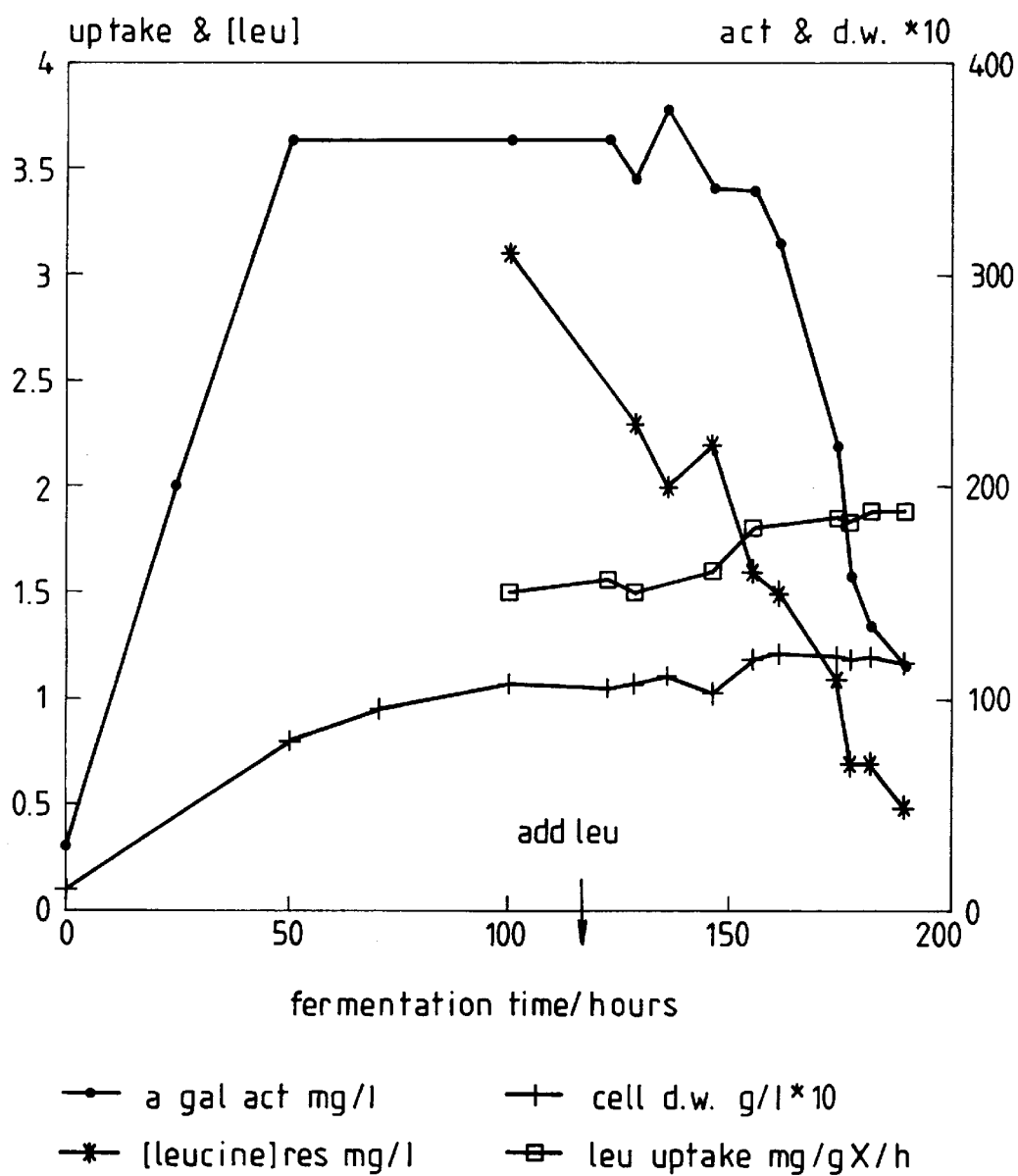
FIG. 17 Southern blot of total DNA of multicopy integrants using the α-galactosidase probe.
  SU50*BglII: parent strain YT6-2-1 L (SU50) total DNA digested with BglII.
  C*BglII: total DNA of multicopy integrant SU50C digested with BglII.
  B*BglII: total DNA of multicopy integrant SU50B digested with BglII.
  C: undigested total DNA of multicopy integrant SU50C.
Figure 18A:
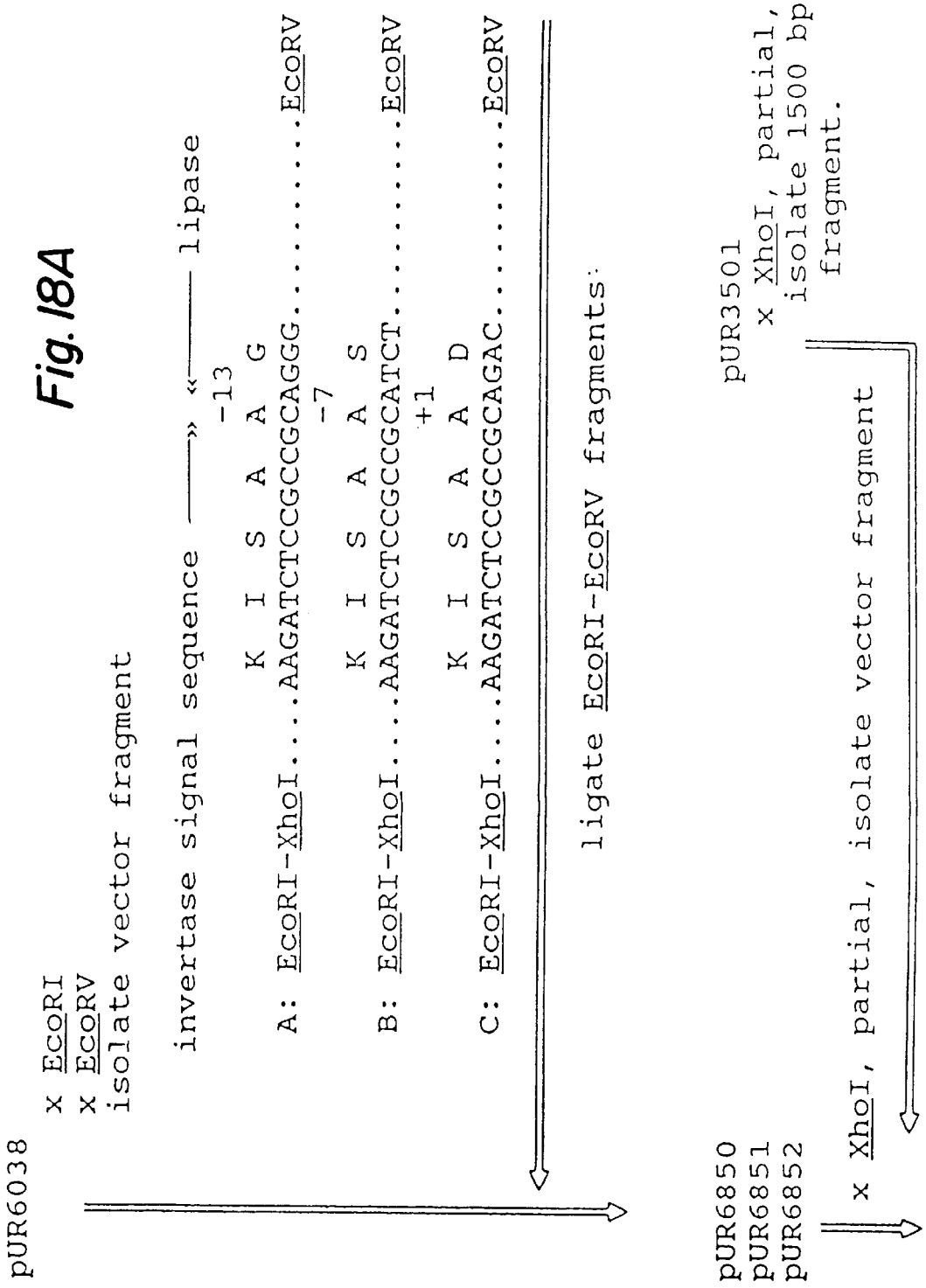
FIG. 18 Southern blot of multicopy integrants using the ribosomal DNA probe.
  SU50*BglII: parent strain YT6-2-1 L (SU50) total DNA digested with BglII.
  C*BglII: total DNA of multicopy integrant SU50C digested with BglII.
  B*BglII: total DNA of multicopy integrant SU50B digested with BglII.
  C: undigested total DNA of multicopy integrant SU50C.
Figure 18B:
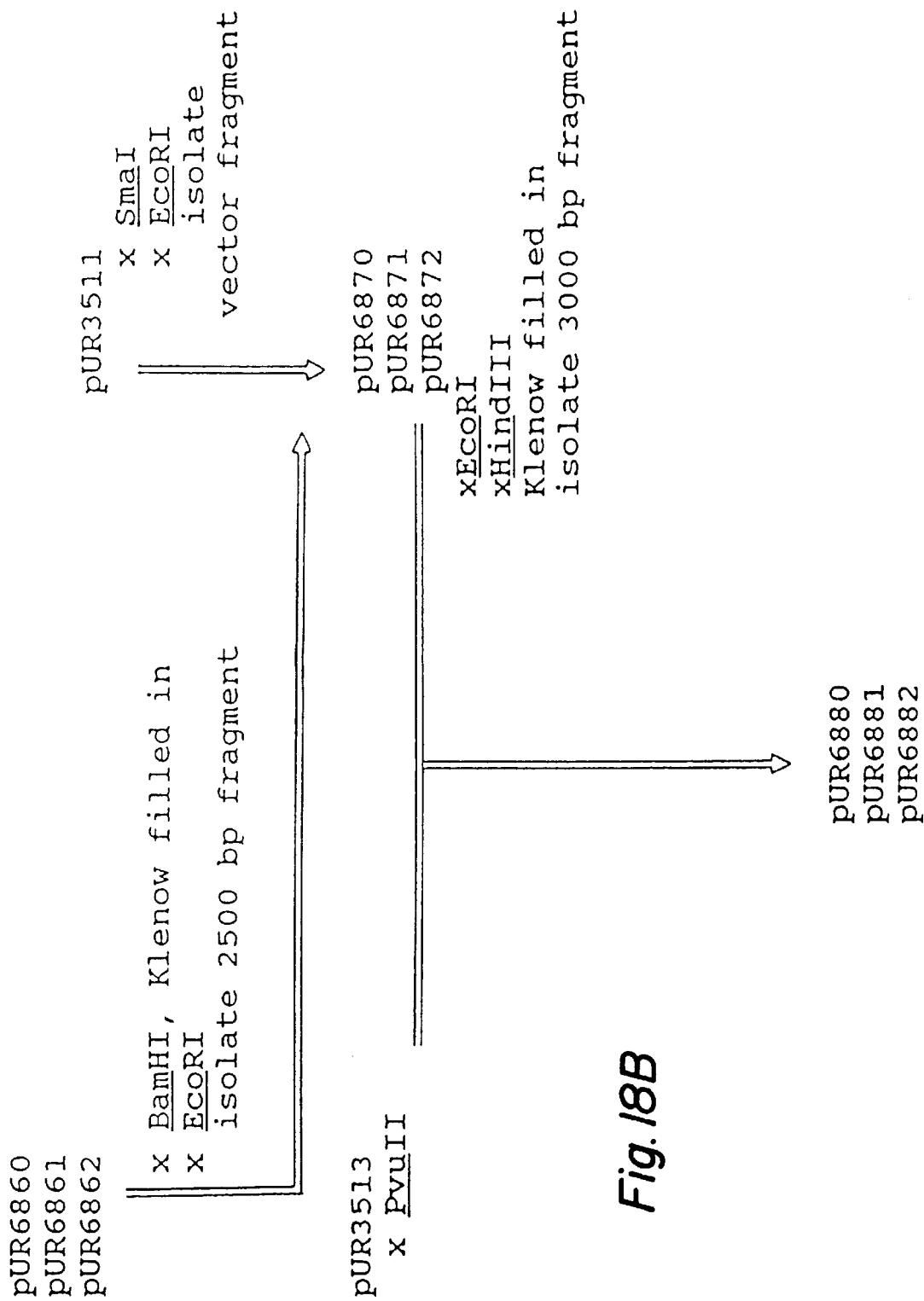
Figure 19:
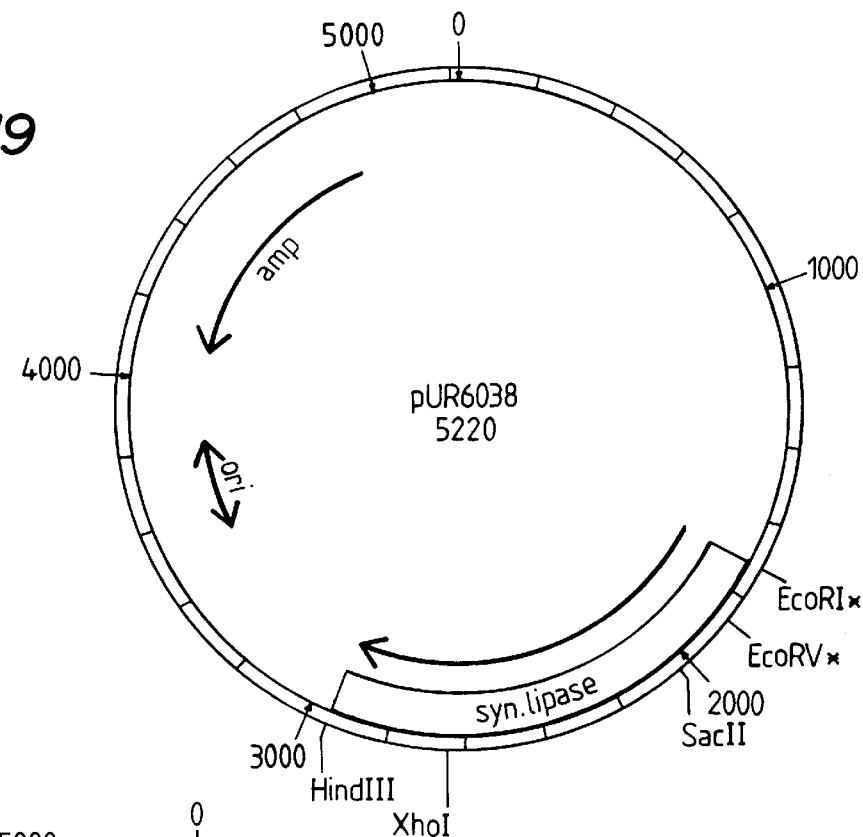
FIG. 19 Structure of the TRP1 gene from (32). [AT]: poly(dA:dT) stretch, (UAS), partial general control upstream activation site. The actual sequence is indicated for the putative TATA elements. The TRP1 coding sequence is indicated by the black bar. The various mRNA species are indicated by the arrows. The scale is in base pairs. The restriction sites used to construct the promoter deletions are indicated.
Figure 20:
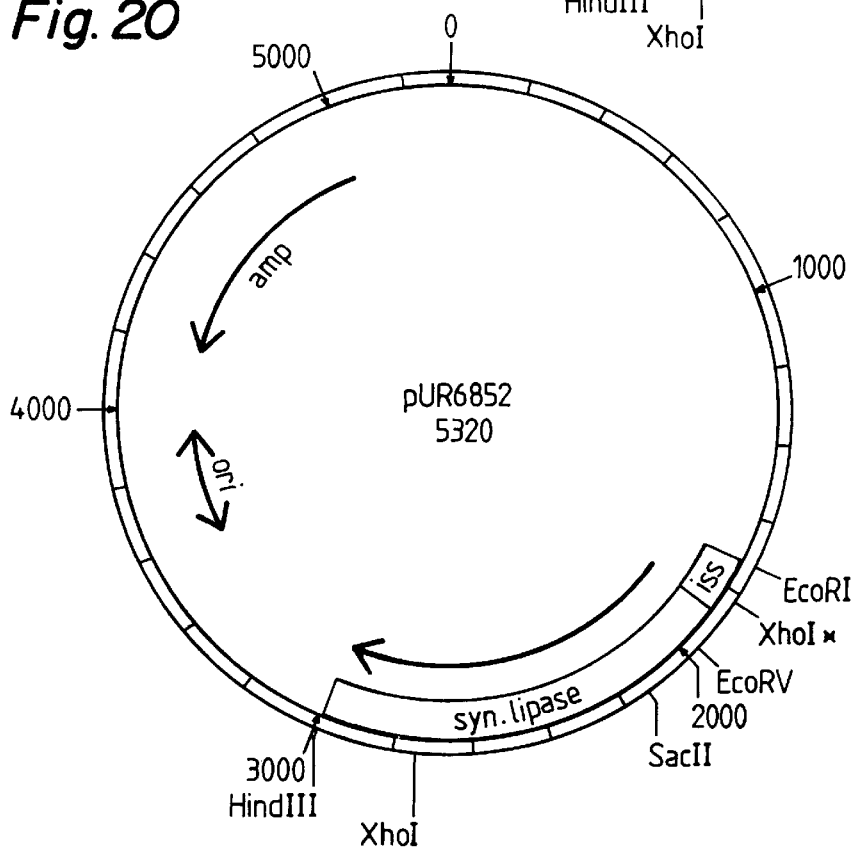
FIG. 20 Construction of plasmids pMIRY6-T±1, pMIRY6-T±2 and pMIRY6-T±3 containing TRP1 alleles with various promoter deletions. The coordinates indicated for several of the restriction sites show their position with respect to the ATG start codon (the A being position +1). For each plasmid the position (−6, −30 or −102) of the 5'-end of the TRP1 gene is indicated. A more detailed map of the rDNA fragment present in the various pMIRY6 plasmids is shown at top right. The non-transcribed rDNA spacer is abbreviated as "N".
Figure 21:
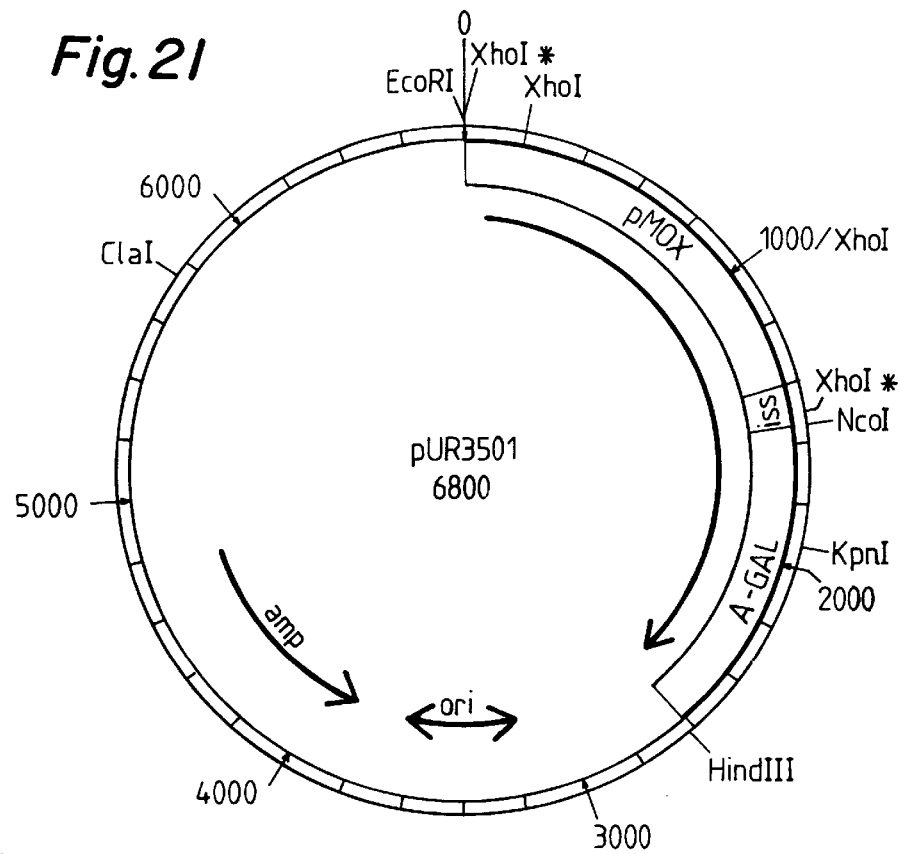
FIG. 21 Plasmid copy number of pMIRY6-TΔ1 (lanes 1 and 2), pMIRY6-TΔ2 (lanes 3 and 4) and pMIRY6-TΔ3 (lanes 5 and 6) transformants. Total DNA was isolated from the transformed cells and digested with EcoRV in the case of pMIRY6-TΔ1 and SacI in the case of pMIRY6-TΔ2 and pMIRY6-TΔ3. The fragments were separated by electrophoresis on an 0.8% gel. The DNA was stained with EtBr. The plasmid and the rDNA bands are indicated.
Figure 22:
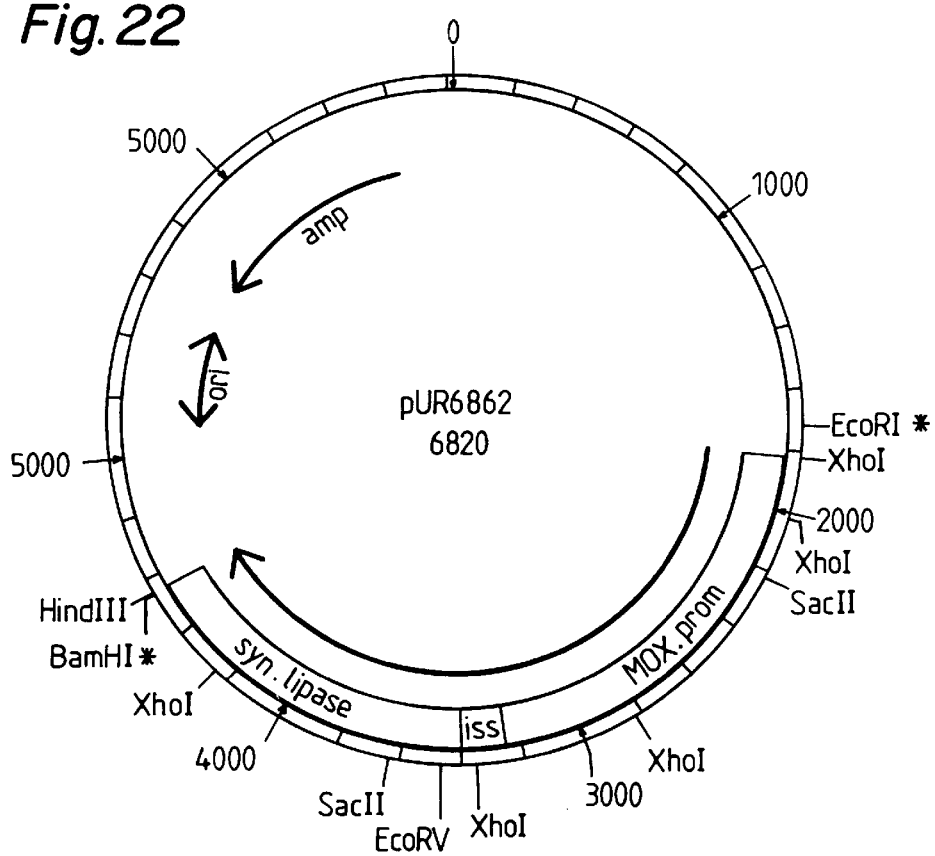
FIG. 22 Construction of pMIRY7-UΔ containing a URA3 gene in which most of the promoter has been deleted. The coordinates indicated for several of the restriction sites refer to their positions with respect to the ATG start codon (the A being position +1). The position of the 5'-end of the URA3± is indicated (Δ16). A more detailed map of the rDNA fragment present in pMIRY7-UΔ is shown at top right. The non-transcribed spacer is abbreviated as "N".
Figure 23:
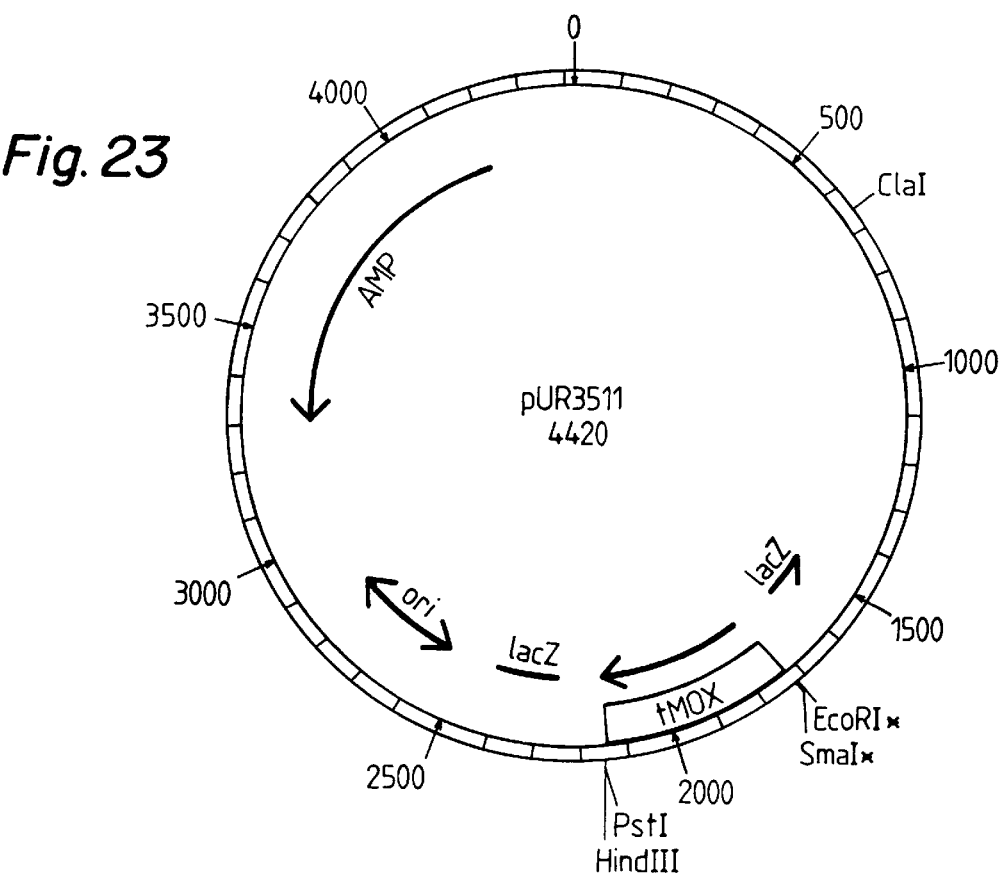
FIG. 23 Plasmid copy number of pMIRY7-UΔ transformants. Total DNA was isolated from the transformed cells and digested with SacI. The fragments were separated by electrophoresis on an 0.8% gel. The 9.1 kb rDNA band and the 6.4 kb plasmid band are indicated.
Figure 24:
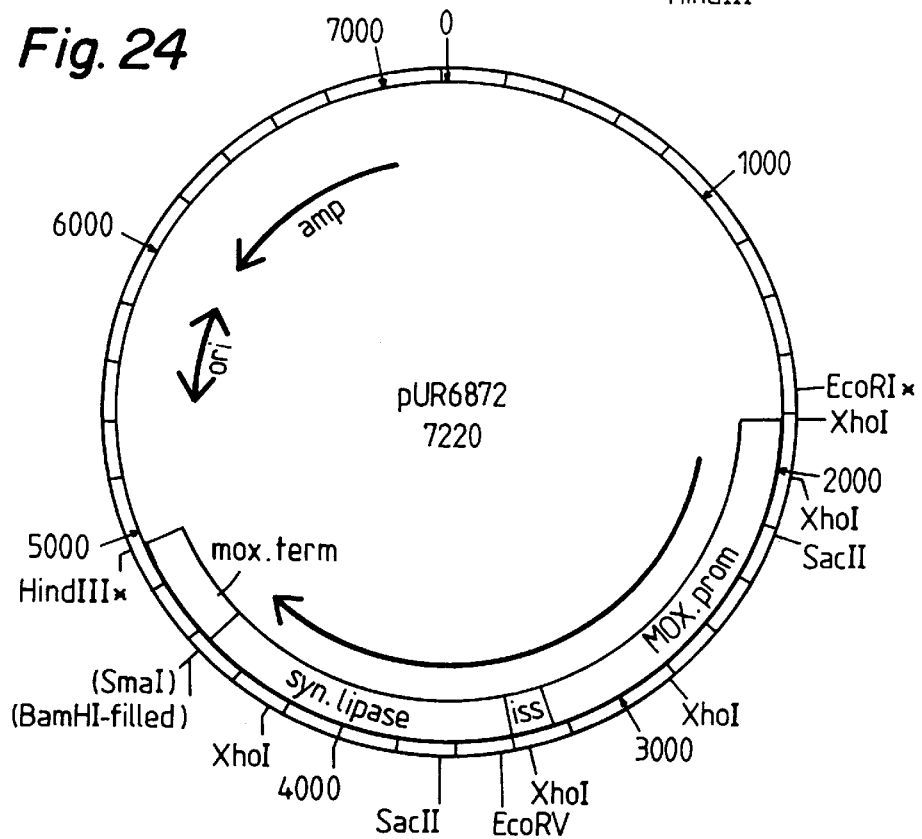
FIG. 24 Stability of multicopy integrant SU50B in continuous culture; for details see text.
Figure 25:
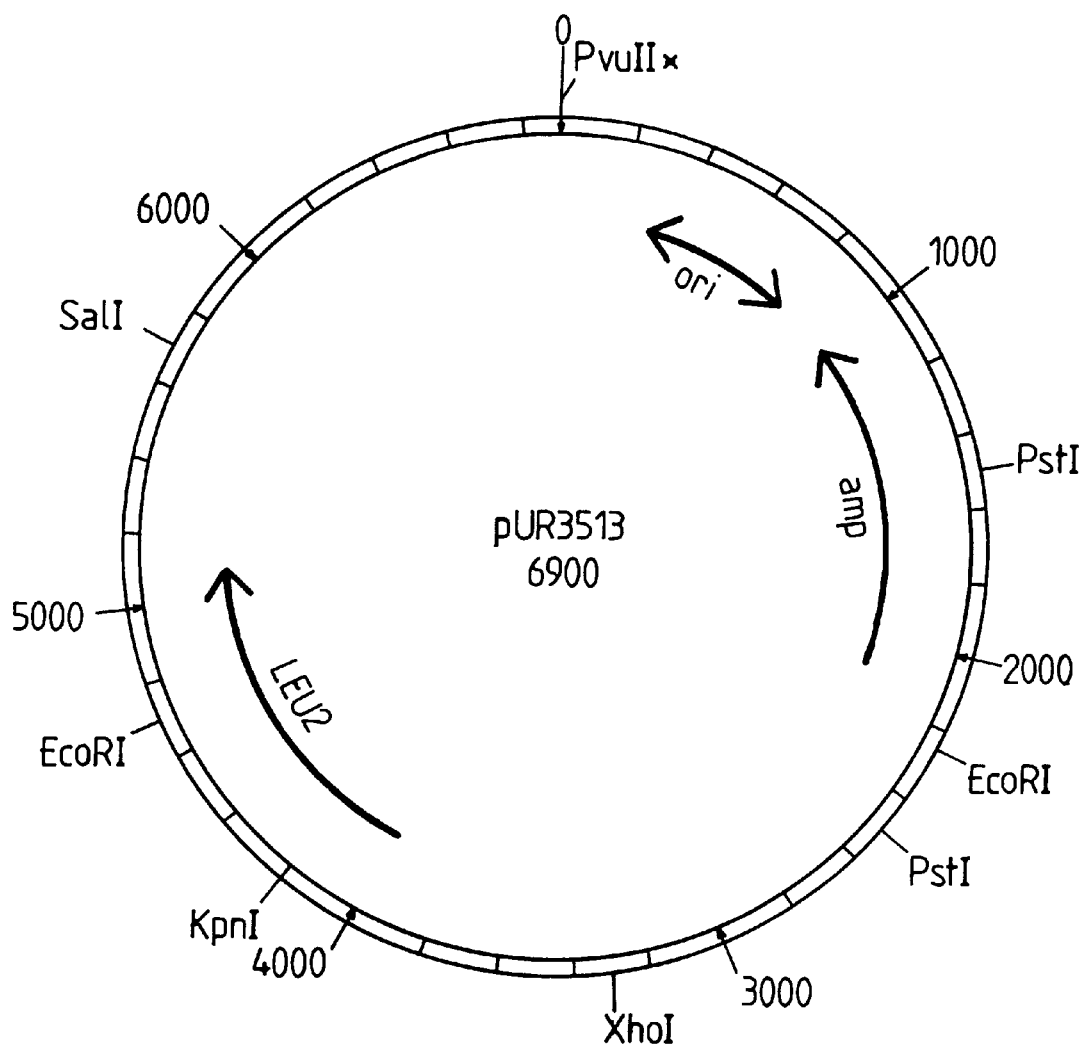
FIG. 25 Southern blot of total DNA digested with BglII of multicopy integrant SU50B isolated at different stages of the continuous culture.
Figure 26:
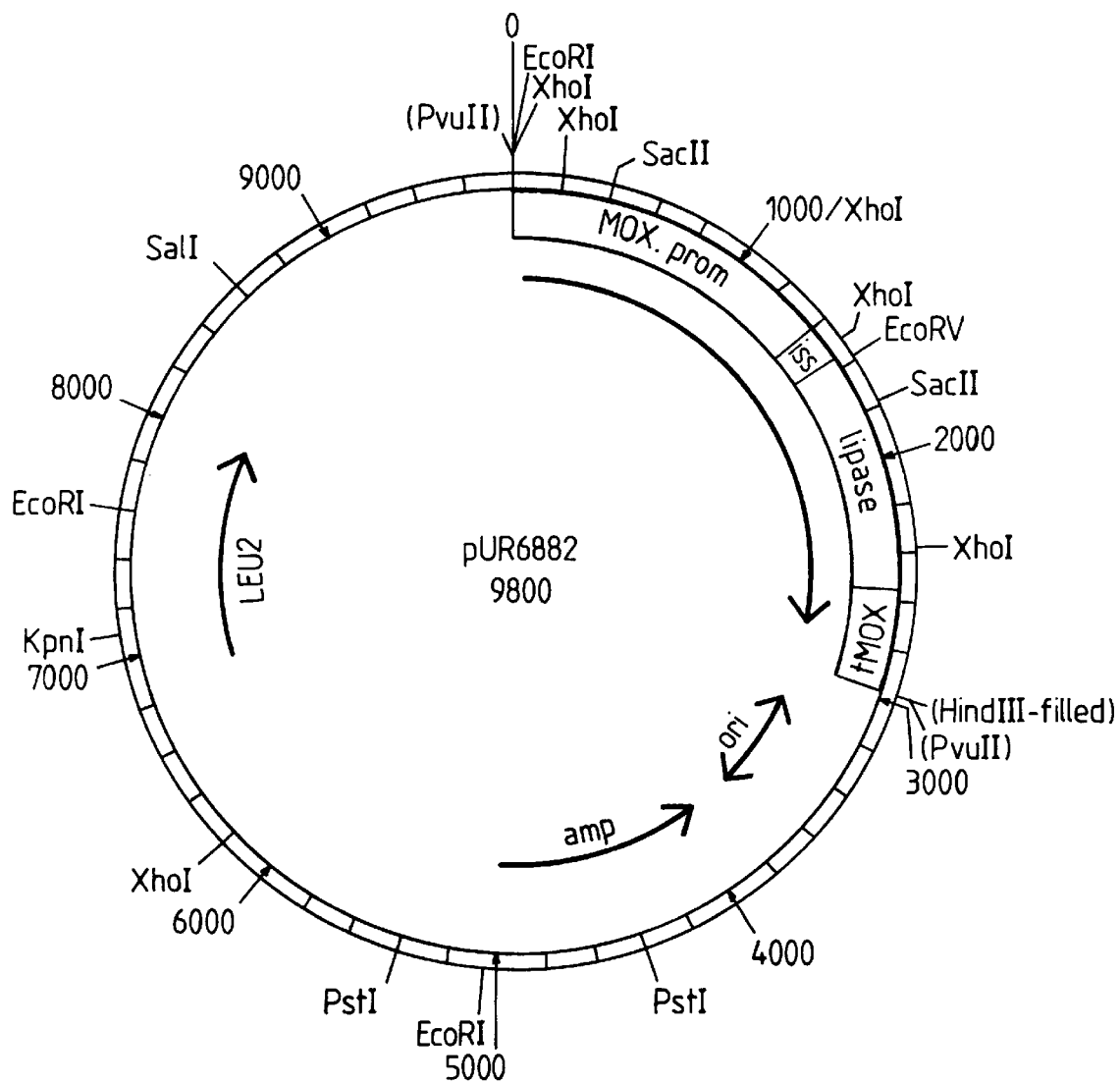

FIG. 26 A schematic drawing of the construction route of the lipase expression vectors for *H. polymorpha* pUR6880, pUR6881 and pUR6882. Each individual stage of the construction route is shown in a separate drawing (FIGS. 27 to 34); for details see text.

Figure 27A:
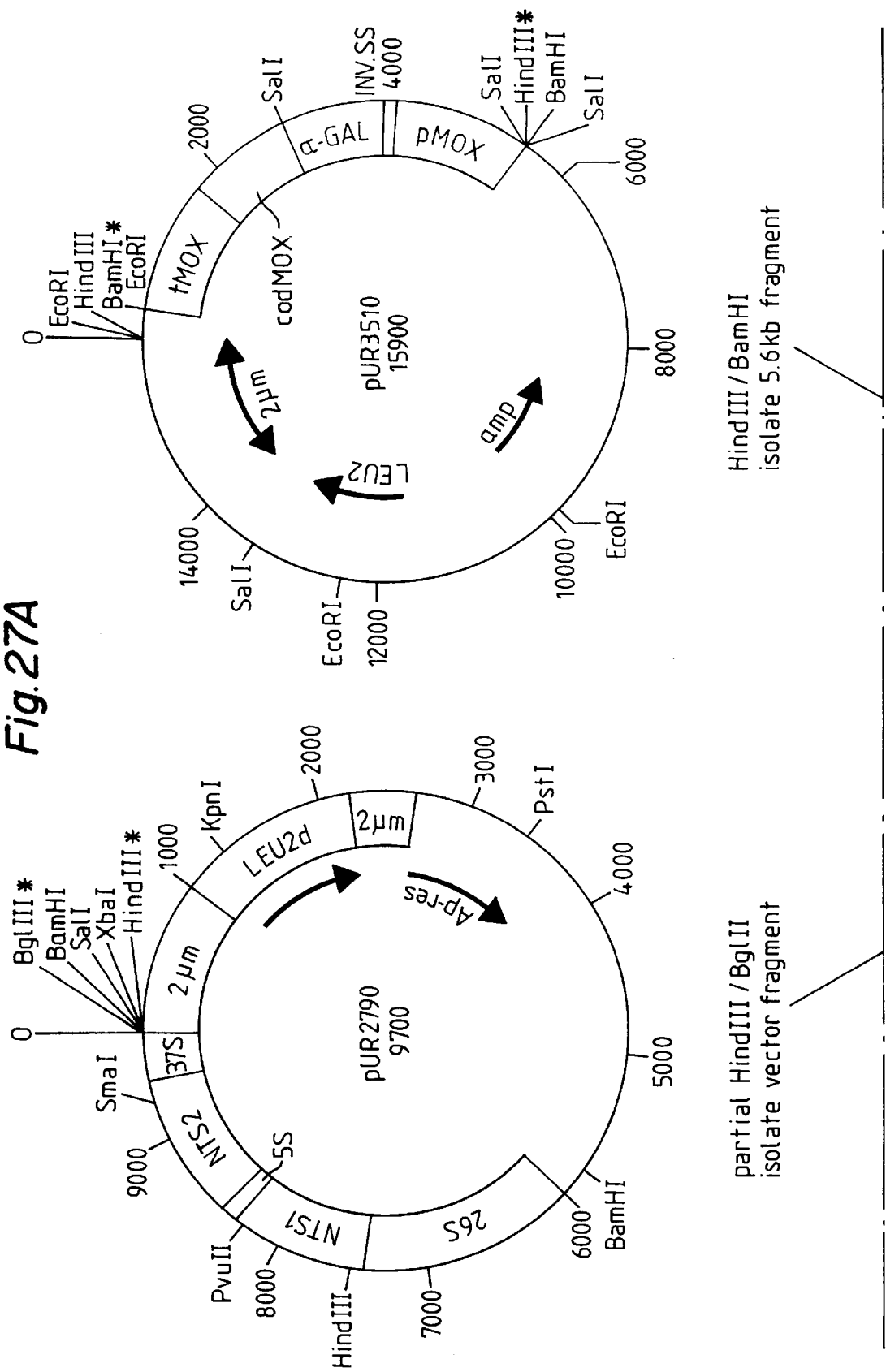
Figure 27B:
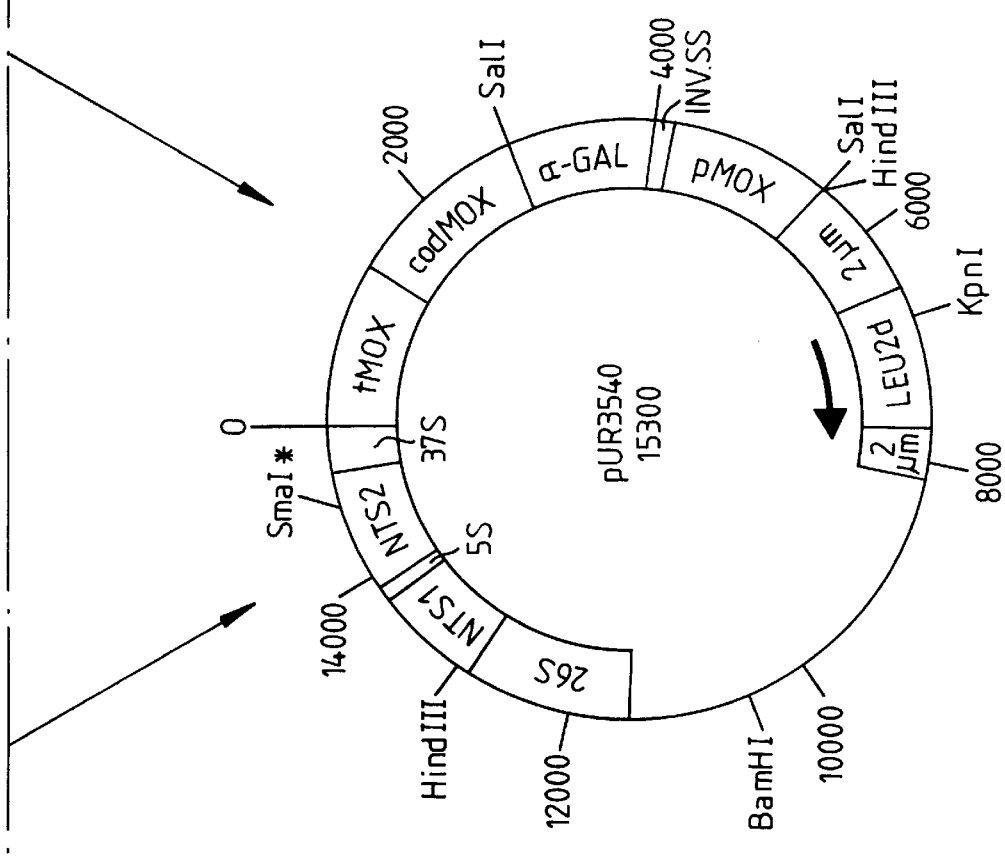
Figure 29:
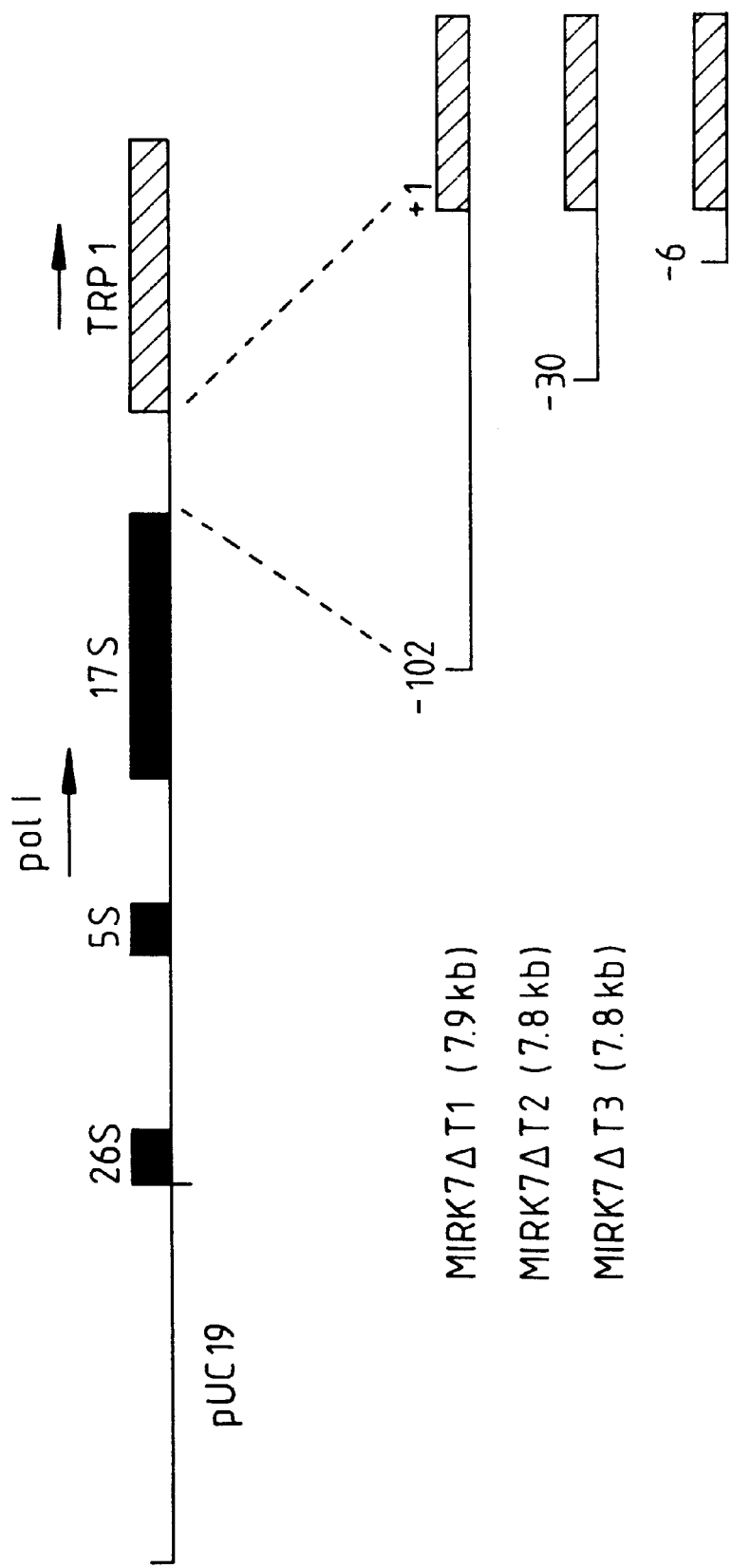

FIG. 27 A schematic drawing of pUR6038.
FIG. 28 A schematic drawing of pUR6852.
FIG. 29 A schematic drawing of pUR3501.
FIG. 30 A schematic drawing of pUR6862.
FIG. 31 A schematic drawing of pUR3511.
FIG. 32 A schematic drawing of pUR6872.
FIG. 33 A schematic drawing of pUR3513.
FIG. 34 A schematic drawing of pUR6882.

FIG. 35 A schematic drawing of the *H. polymorpha* multicopy integration vector pUR3540 comprising the α-galactosidase expression cassette. All used restriction recognition enzyme sites are marked with an asterisk.

FIG. 36 Southern analysis of total DNA digested with HindIII of the *H. polymorpha* multicopy integrant obtained using pUR3540.

lane 1: multicopy integrant.

lane 2: untransformed host strain.

FIG. 37 The cloned ribosomal DNA of *K. lactis* is shown (42). From this vector the indicated BamHI-SacI fragment was subcloned in pTZ19U (46). From the resulting vector the EcoRI fragment was used in the construction of pMIRK7ΔT1, pMIRK7ΔT2 and pMIRK7ΔT3. The EcoRI-PstI fragment was used as a probe in the hybridization experiments.

FIG. 38 A schematic drawing of the multicopy integration vectors pMIRK7ΔT1, pMIRK7ΔT2 and pMIRK7ΔT3.

FIG. 39 Hybridization of digested chromosomal DNA of multicopy integrant after growth under non-selective conditions with ribosomal DNA probe. Lane 1–4: multicopy integrant MIRK7ΔT1; lane 5: parent strain MSK 110, lane 6: linearized multicopy integration vector pMIRK7ΔT1. Chromosomal DNA was isolated at the start of the experiment (lane 1), after 6–7 generations (lane 2), after 30–35 generations (lane 3) and after 60–70 generations (lane 4).

We claim:

1. In a process for preparing a protein by a fungus transformed by multicopy integration of an expression vector in the ribosomal DNA of the fungus, the expression vector including in addition to an expressible structural gene encoding the protein an expressible deficient selection marker gene needed for the production of an ingredient essential for growth of the fungus, the essential ingredient being selected from the group consisting of amino acids, vitamins and nucleotides, said fungus having been modified prior to transformation to inactivate the wild type gene corresponding to said expressible deficient selection marker the improvement wherein fungal cells are maintained with high copy number integrants, and consequent improved production of the protein, by transforming the fungal cells with the expression vector which has approximately the same length as one DNA sequence that codes for a ribosomal DNA unit of the fungus, whereby fungal cells with high copy number integrants are preferentially maintained over fungal cells with low copy number integrants, whereby the production of the protein is improved.

2. The process according to claim 1, in which the length of the expression vector is about 8–10 kb.

3. The process according to claim 2, in which the fungus is *Saccharomyces cerevisiae* and the length of the expression vector is about 9 kb.

* * * * *